United States Patent
Avneri et al.

(10) Patent No.: US 10,987,488 B2
(45) Date of Patent: Apr. 27, 2021

(54) VESSEL CANNULATION DEVICE AND METHOD OF USE

(71) Applicant: TRAUMATEK SOLUTIONS, B.V., Amsterdam (NL)

(72) Inventors: Itzhak Avneri, Tel Aviv-Jaffa (IL); Ben-Ami Avneri, Moshav Udim (IL); Shahar Avneri, Herzliya (IL); Lior Avneri, New York, NY (US)

(73) Assignee: TRAUMATEK SOLUTIONS, B.V., Amsterdam (NL)

( * ) Notice: Subject to any disclaimer, the term of this patent is extended or adjusted under 35 U.S.C. 154(b) by 1344 days.

(21) Appl. No.: 15/191,216

(22) Filed: Jun. 23, 2016

(65) Prior Publication Data

US 2016/0375223 A1 Dec. 29, 2016

Related U.S. Application Data

(60) Provisional application No. 62/311,249, filed on Mar. 21, 2016, provisional application No. 62/183,554, filed on Jun. 23, 2015.

(51) Int. Cl.
*A61B 5/00* (2006.01)
*A61M 25/01* (2006.01)
(Continued)

(52) U.S. Cl.
CPC ..... *A61M 25/0113* (2013.01); *A61B 5/15003* (2013.01); *A61B 5/1535* (2013.01);
(Continued)

(58) Field of Classification Search
CPC .. A61M 25/0113; A61M 25/06; A61M 25/09; A61M 2210/005; A61B 5/15003; A61B 5/150748; A61B 5/150992
See application file for complete search history.

(56) References Cited

U.S. PATENT DOCUMENTS

| 4,427,290 A | 1/1984 | Kaye et al. |
| 4,671,287 A | 6/1987 | Fiddian-Green |

(Continued)

FOREIGN PATENT DOCUMENTS

| EP | 0832663 A2 | 4/1998 |
| JP | 2002-520100 A | 7/2002 |

(Continued)

OTHER PUBLICATIONS

Final Office Action dated Oct. 19, 2017 in corresponding U.S. Appl. No. 15/254,803 (11 pages).

(Continued)

*Primary Examiner* — Max F Hindenburg
(74) *Attorney, Agent, or Firm* — Venable LLP; Michele V. Frank

(57) ABSTRACT

Devices and methods are provided for automatic vascular access. An automatic vessel cannulation device, mechanical or electronic, has a sensor configured to detect a physiologic parameter of a needle tip, and a blunting device advancing member released in response to the sensor. The sensor may measure pressure or any other physiological parameter. A processor is configured to analyze data sent by the sensor and is pre-set to identify parameters unique to arteries, veins, or other body cavities or organs. A method may include comparing a physiologic parameter with pre-determined parameters to deploy a blunting element if the physiologic parameter is within a range of the pre-determined parameters. An expandable sheath may be included. A device can be provided having a motor controlling the cannulation device orientation to scan tissue with the tip of the needle by moving the cannulation device through the ultrasound transducer.

62 Claims, 35 Drawing Sheets

(51) Int. Cl.
    *A61B 5/15*     (2006.01)
    *A61B 5/153*    (2006.01)
    *A61M 5/32*     (2006.01)
    *A61M 5/158*    (2006.01)
    *A61M 25/06*    (2006.01)

(52) U.S. Cl.
    CPC .. *A61B 5/150748* (2013.01); *A61B 5/150992* (2013.01); *A61M 5/326* (2013.01); *A61M 25/0606* (2013.01); *A61M 2005/1588* (2013.01); *A61M 2205/3303* (2013.01)

(56) References Cited

U.S. PATENT DOCUMENTS

| | | |
|---|---|---|
| 4,689,041 A | 8/1987 | Corday et al. |
| 4,721,123 A | 1/1988 | Cosentino et al. |
| 4,917,094 A | 4/1990 | Lynch et al. |
| 5,176,659 A | 1/1993 | Mancini |
| 5,256,150 A | 10/1993 | Quiachon et al. |
| 5,312,361 A | 5/1994 | Zadini et al. |
| 5,318,588 A | 6/1994 | Horzewski et al. |
| 5,320,611 A | 6/1994 | Bonutti et al. |
| 5,335,551 A | 8/1994 | Ohnishi et al. |
| 5,415,177 A | 5/1995 | Zadini et al. |
| 5,480,388 A | 1/1996 | Zadini et al. |
| 5,527,290 A | 6/1996 | Zadini et al. |
| 5,527,291 A | 6/1996 | Zadini et al. |
| 5,579,780 A | 12/1996 | Zadini et al. |
| 5,749,371 A | 5/1998 | Zadini et al. |
| 5,749,835 A | 5/1998 | Glantz |
| 5,944,691 A | 8/1999 | Querns et al. |
| 5,997,508 A | 12/1999 | Lunn et al. |
| 6,115,624 A | 9/2000 | Lewis et al. |
| 6,190,357 B1 | 2/2001 | Ferrari et al. |
| 6,197,001 B1 | 3/2001 | Wilson et al. |
| 6,217,558 B1 | 4/2001 | Zadini et al. |
| 6,245,052 B1 | 6/2001 | Orth et al. |
| 6,263,230 B1 | 7/2001 | Haynor et al. |
| 6,626,869 B1 | 9/2003 | Bint |
| 6,692,462 B2 | 2/2004 | Mackenzie et al. |
| 6,808,520 B1 | 10/2004 | Fourkas et al. |
| 6,827,710 B1 | 12/2004 | Mooney et al. |
| 7,197,354 B2 | 3/2007 | Sobe |
| 7,331,922 B2 | 2/2008 | Mohl |
| 7,343,195 B2 | 3/2008 | Strommer et al. |
| 7,449,011 B2 | 11/2008 | Wenchell et al. |
| 7,753,887 B2 | 7/2010 | Botich et al. |
| 7,766,820 B2 | 8/2010 | Core |
| 7,881,769 B2 | 2/2011 | Sobe |
| 7,927,309 B2 | 4/2011 | Palm |
| 8,313,493 B2 | 11/2012 | Fischer |
| 8,971,994 B2 | 3/2015 | Burnside et al. |
| 9,439,653 B2 | 9/2016 | Avneri et al. |
| 2001/0012950 A1 | 8/2001 | Nishtala et al. |
| 2001/0023334 A1 | 9/2001 | St. Goar et al. |
| 2002/0183781 A1 | 12/2002 | Casey et al. |
| 2003/0073955 A1 | 4/2003 | Otawara |
| 2004/0006305 A1 | 1/2004 | Hebert et al. |
| 2004/0059179 A1 | 3/2004 | Maguire et al. |
| 2005/0075606 A1 | 4/2005 | Botich et al. |
| 2005/0080430 A1 | 4/2005 | Wright et al. |
| 2005/0165328 A1* | 7/2005 | Heske ............... A61B 10/0275 600/566 |
| 2006/0106336 A1 | 5/2006 | Saab |
| 2006/0116633 A1 | 6/2006 | Shachar |
| 2006/0264905 A1 | 11/2006 | Eskridge et al. |
| 2007/0185380 A1 | 8/2007 | Kucklick |
| 2008/0004571 A1 | 1/2008 | Voss |
| 2008/0058836 A1 | 3/2008 | Moll et al. |
| 2008/0132911 A1 | 6/2008 | Sobe |
| 2008/0147002 A1 | 6/2008 | Gertner |
| 2008/0221593 A1 | 9/2008 | Liddicoat et al. |
| 2008/0294251 A1 | 11/2008 | Annest et al. |
| 2009/0156926 A1 | 6/2009 | Messerly et al. |
| 2009/0177183 A1 | 7/2009 | Pinkernell et al. |
| 2009/0240202 A1 | 9/2009 | Drasler et al. |
| 2009/0254166 A1 | 10/2009 | Chou et al. |
| 2009/0287182 A1 | 11/2009 | Bishop et al. |
| 2009/0287223 A1 | 11/2009 | Pua et al. |
| 2010/0030162 A1 | 2/2010 | Cremascoli et al. |
| 2010/0049062 A1 | 2/2010 | Ziv |
| 2010/0094143 A1 | 4/2010 | Mahapatra et al. |
| 2010/0130937 A1 | 5/2010 | Voss |
| 2010/0168674 A1* | 7/2010 | Shaw ................ A61M 39/06 604/164.07 |
| 2010/0198159 A1 | 8/2010 | Voss et al. |
| 2010/0198160 A1 | 8/2010 | Voss |
| 2010/0204613 A1 | 8/2010 | Rollins et al. |
| 2010/0210934 A1 | 8/2010 | Belson |
| 2010/0234873 A1 | 9/2010 | Nagano et al. |
| 2010/0274178 A1 | 10/2010 | LePivert |
| 2011/0034986 A1 | 2/2011 | Chou et al. |
| 2011/0152836 A1 | 6/2011 | Riopelle et al. |
| 2011/0190697 A1 | 8/2011 | Farnan |
| 2011/0295177 A1 | 12/2011 | Mohl |
| 2012/0136343 A1 | 5/2012 | Burnett |
| 2012/0190981 A1* | 7/2012 | Harris ............. A61B 5/150389 600/439 |
| 2013/0281787 A1 | 10/2013 | Avneri et al. |
| 2014/0378867 A1 | 12/2014 | Belson |
| 2015/0065916 A1 | 3/2015 | Maguire et al. |
| 2016/0375223 A1 | 12/2016 | Avneri et al. |

FOREIGN PATENT DOCUMENTS

| | | |
|---|---|---|
| WO | 00/02616 A1 | 1/2000 |
| WO | WO-2008/137956 A2 | 11/2008 |
| WO | WO-2010/036560 A1 | 4/2010 |
| WO | WO-2010/056538 A1 | 5/2010 |
| WO | 2011/022073 A1 | 2/2011 |
| WO | WO-2012/088471 A1 | 6/2012 |
| WO | 2014/006403 A1 | 1/2014 |
| WO | WO-2015/031481 A1 | 3/2015 |

OTHER PUBLICATIONS

Japanese Office Action in Japanese Patent Application No. 2015-501826 dated Jan. 18, 2017 (w/ English translation).
Notification of Transmittal, International Search Report, and Written Opinion for International Application No. PCT/IB2016/001013 (dated Jan. 24, 2017).
Saito, H., et al., "Detection of Needle Puncture to Blood Vessel Using Puncture Force Measurement", Medical and Biological Engineering and Computing, Apr. 2005, vol. 43, Issue 2, pp. 240-244.
VenousPro Product Description, Vasculogic, LLC, 2010, available online at <http://vasculogic.com/venouspro.html>, (last accessed Mar. 17, 2017).
Non-Final Office Action dated Apr. 13, 2017 in corresponding U.S. Appl. No. 15/254,803 (14 pages).
Advisory Action dated Jun. 15, 2017 in corresponding U.S. Appl. No. 13/844,319 (5 pages).
Non-Final Office Action dated Oct. 19, 2015 in corresponding U.S. Appl. No. 13/708,878 (14 pages).
Final Office Action dated Dec. 13, 2016 in corresponding U.S. Appl. No. 13/844,319 (14 pages).
Non-Final Office Action dated Mar. 22, 2016 in corresponding U.S. Appl. No. 13/844,319 (10 pages).
Non-Final Office Action dated Jul. 25, 2017 in corresponding U.S. Appl. No. 13/844,319 (16 pages).
Office Action dated Jun. 30, 2017 in corresponding Chinese Patent Application No. 201380023621.5 with English Translation (4 pages).
Assar, A.N. et al., "Endovascular proximal control of ruptured abdominal aortic aneurysms: the internal aortic clamp," J Cardiovasc Surg (Torino), 2009; 50:381-5.
Avaro, J-P. et al., "Forty-Minute Endovascular Aortic Occlusion Increases Survival in an Experimental Model of Uncontrolled Hemorrhagic Shock Caused by Abdominal Trauma," Journal of Trauma-Injury Infection & Critical Care, 2011; 71:720-726.
Bell-Thomas, S.M. et al., "Emergency use of a transfemoral aortic occlusion catheter to control massive haemorrhage at caesarean hysterectomy," BJOG, 2003;110:1120-2.

(56) References Cited

OTHER PUBLICATIONS

Blackbourne, L. H. et al., "Exsanguination Shock: The Next Frontier in Prevention of Battlefield Mortality," Journal of Trauma-Injury Infection & Critical Care, 2011; 7:S1-S3.

Boctor, E., et al., "Three-dimensional ultrasound-guided robotic needle placement: an experimental evaluation", Int J Med Robot. Jun. 2008; 4(2): 180-191.

Champion H.R., et al., "A profile of combat injury," A. J Trauma, 2003; 54(5 Suppl):S13-9.

Cincinnati Children's Hospital Press Release, "International Collaborative Funds Three Early-Stage Pediatric Medical Device Concepts", Dec. 21, 2012, available online at <http://www.cincinnatichildrens.org/news/release/2012/bgucincinnati-childrens-collaboration-12-21-2012/> (last accessed Jun. 22, 2015).

Cothren C.C. and Moore, E. A.,"Emergency department thoracotomy for the critically injured patient: Objectives, indications, and outcomes," World J Emerg Surg., 2006;1:4.

Edens, J.W. et al., "Longterm outcomes after Combat Casualty Emergency Department Thoracotomy," J Am Coll Surg., 2009; 209(2):188-97.

Extended European Search Report in European Patent Application No. 13764355.7 dated Sep. 28, 2015.

Martinelli, T et al. "Intra-aortic balloon occlusion to salvage patients with life-threatening hemorrhagic shocks from pelvic fractures," J Trauma, 2010; 68(4):942-8.

Notification of Transmittal, International Search Report, and Written Opinion for International Application No. PCT/US2013/032641 (dated Aug. 6, 2013).

Perry, S., Making a robot that can draw blood faster and more safely than a human can, IEEE Spectrum, Jul. 26, 2013, available online at <http://spectrum.ieee.org/robotics/medical-robots/profile-veebot> (last accessed Jun. 22, 2015).

Rabinovici R., et al., "Control of bleeding is essential for a successful treatment of hemorrhagic shock with 7.5 percent sodium chloride solution," Surg Gynecol Obstet. 1991; 173(2):98-106 (Abstract only).

Saito, H., et al., "Detection of needle puncture to blood vessel using puncture force measurement", Medical and Biological Engineering and Computing , 2005, vol. 43, Issue 2, pp. 240-244 (Abstract only).

Tang, X et al. "Use of Aortic Balloon Occlusion to Decrease Blood Loss During Sacral Tumor Resection", The Journal of Bone & Joint Surgery, 2010; 92:1747-1753.

Veebot: Automated Venipuncture Product Description, Veebot LLC, 2014, available online at <http://www.veebot.com/solutions.html> (last accessed Jun. 22, 2015).

VenousPro Product Description, Vasculogic, LLC, 2010, available online at <http://vasculogic.com/venouspro.html>, (last accessed Jun. 22, 2015).

White, J.M. et al., "Endovascular balloon occlusion of the aorta is superior to resuscitative thoracotomy with aortic clamping in a porcine model of hemorrhagic shock," Surgery, 2011; 150:400-9.

Zivanovic, A., et al., "A robotic system for blood sampling", IEEE Trans Inf Technol Biomed., Mar. 2000;4(1):8-14 (Abstract only).

Australian Examination Report No. 2 issued in related Australian Patent Application No. 2013235348 dated Dec. 5, 2017.

Office Action issued in related U.S. Appl. No. 15/254,803 dated Feb. 22, 2018.

International Preliminary Report issued in related International Patent Application No. PCT/US2013/032641 dated Sep. 24, 2014.

Notice of Allowance issued in related U.S. Appl. No. 13/708,878 dated May 9, 2016.

Office Action issued in related U.S. Appl. No. 13/844,319 dated Mar. 29, 2018.

Notice of Allowance issued in related U.S. Appl. No. 13/844,319 dated Jul. 6, 2018.

Notice of Allowance issued in related U.S. Appl. No. 15/254,803 dated Jul. 2, 2018.

Australian Examination Report No. 1 issued in related Australian Patent Application No. 2013235348 dated Dec. 6, 2016.

Australian Examination Report No. 1 issued in related Australian Patent Application No. 2017272200 dated Jan. 15, 2019.

Office Action issued in related Chinese Patent Application No. 201380023621.5 dated Jan. 20, 2016.

Office Action issued in related Chinese Patent Application No. 201380023621.5 dated Nov. 3, 2016.

Notification of Reasons for Refusal issued in related Japanese Patent Application No. 2017-253704 dated Feb. 25, 2019.

Office Action issued in related European Patent Application No. 17203668.3 dated Mar. 6, 2020.

Office Action issued in related Canadian Patent Application No. 2,867,460 dated Sep. 16, 2019.

Office Action issued in related European Patent Application No. 16753962.6 dated Feb. 12, 2020.

Notice of Reasons for Rejection issued in related Japanese Patent Application No. 2017-253704 dated Oct. 18, 2019.

Extended European Search Report issued in related European Patent Application No. 17203668.3 dated Feb. 20, 2018.

Non-Final Office Action in corresponding U.S. Appl. No. 16/153,365, dated Sep. 3, 2020.

Non-Final Office Action in corresponding U.S. Appl. No. 16/153,365, dated Dec. 16, 2019.

\* cited by examiner

VESSEL CANNULATION DEVICE AND METHOD OF USE

CROSS REFERENCE TO RELATED APPLICATIONS

This application claims priority to U.S. Provisional Application No. 62/311,249 (filed Mar. 21, 2016) and 62/183,554 (filed Jun. 23, 2015), both of which are hereby incorporated herein by reference in their entirety.

BACKGROUND

Vascular access is a crucial element of medical therapy in a vast majority of clinical settings and procedures. This is true in both elective and in emergent situations. In a specific type of emergency, hemorrhagic shock, there may further be a need to perform aortic occlusion. Both these clinical needs, vascular access and aortic occlusion, are the subject of the current invention.

Vascular Access

A large part of medical interventions, both elective and emergent, are endovascular procedures. These procedures have become very common and continue to grow in numbers due to both the increase in cardiovascular patient absolute numbers and to the trend of shifting from open surgery to endovascular surgery.

Once vascular access is secured, delivery of treatment is quick and easy, be it the administration of fluids, analgesics, sedative medications, vasopressors, inotropics, percutaneous endovascular trans-catheter treatments or other interventions. Patient monitoring is also aided by central vascular access, as it enables direct arterial or venous pressure measurements and blood sampling.

Vascular Access in Elective Situations

Although extremely common, the ways to establish vascular access remain very basic and are often inadequate. This is especially unfortunate in elective settings, as it is the older and sicker individuals who usually have more "difficult blood vessels", and must frequently endure additional suffering caused by painful repeated attempts at blood vessel cannulation, even when performed by experienced personnel.

Vascular Access in Emergency Situations

In emergency situations, the importance of vascular access is increased, as stabilization of patients often requires administration of fluids or blood and medications. However, the emergency setting also increases the obstacles to successful blood vessel cannulation. Possible impediments include environmental factors such as darkness (night), cold and wet weather, unstable surroundings (wind, waves, bumpy vehicle or aircraft), patient factors such as shock which may cause collapse of veins and an impalpable arterial pulse, burns, or movements due to shivering or convulsions, care provider factors such as stress caused by the need to deliver therapy urgently in a dying patient, additional patients, imminent danger from warfare or natural hazards, or lack of expertise, and finally equipment factors such as the absence of expensive ultrasound guidance. A venous cut down may be performed using simple tools by an experienced physician, but this too takes time and requires certain expertise, making it impractical in many cases.

In performing an endovascular procedure, access into the vasculature must be established and maintained for the duration of the procedure. This is most commonly done by placing an introducer sheath in the blood vessel to enable passage of the interventional instruments in and out without losing the entry point or causing damage to the vessel.

Placement of an endovascular sheath is usually performed using the modified Seldinger technique. This entails puncture of the vessel with a needle, passage of a guidewire through the needle, removal of the needle, incision of the skin, placement of a sheath with a dilator in it over the guidewire, removal of the guidewire and dilator.

The Seldinger technique, although useful, suffers from several drawbacks. First, it requires significant experience in order to be successfully performed, especially when circumstances are suboptimal such as in emergency and trauma situations. As it is mainly used for placement of large bore catheters, which are less common than regular small-medium bore venous catheters, the exposure to it (and hence the procedure practice) is less than that of over the needle venous catheter placement. Second, there are several points during the procedure which may lead to its failure.

One such point is after entry of the needle into the blood vessel, which is evident by the flow of blood out of the needle. At this point, the physician must thread a guidewire into the needle. Holding the needle absolutely still, while bringing the guidewire and threading it with the other hand requires a certain level of coordination, which not all physicians possess. Even the slightest movement of the needle at this stage might cause it to move forward and exit the artery through its posterior wall, or withdraw out of the lumen through the anterior wall of the artery. This will prevent the guidewire from entering the lumen and will require an additional puncture attempt. Additionally, this might cause blood to leak around the vessel causing an internal hematoma, which might compress the vessel and make repeat cannulation more difficult. Worse yet, unintended movement of the needle might place it within one of the arterial walls, and attempted insertion of the guidewire can then damage the arterial wall, possibly leading to large hematomas or other complications.

Another sensitive point in the procedure is after the guidewire insertion and needle removal. The physician must now thread the guidewire edge into the dilator, which has a very small aperture the size of the guidewire, while at the same time compressing the puncture site to prevent hematoma and make sure the guidewire is not pulled out. Exit of the guidewire from the artery at this stage will cause the sheath to be placed into tissues instead of into the artery, which besides tissue damage usually causes the guidewire to bend, necessitating its replacement.

Additional drawbacks of the Seldinger technique are related to the use of a long guidewire, which carries with it an increased risk of contamination of its proximal end, as well as a danger of splashing blood on the physician. Also, during the time between needle entry into the vessel and until the guidewire is inserted into it, either profuse bleeding or entry of air into the circulation might occur, depending on whether pressure within the vessel is higher or lower than ambient pressure.

In contrast to the above, regular small to medium bore venous cannulas are usually placed using the "over-the-needle" technique. With this technique, the cannula, which has an inner diameter ("ID") matched to the outer diameter ("OD") of the needle, is inserted into the artery together with the needle. When blood is observed in a "flash" chamber connected to the needle lumen, the needle is held in place and the cannula is manually advanced and slid over the needle into the vessel. Not only is this technique technically simpler than the Seldinger technique, it is also more commonly used, and there is a greater possibility of exposure to it for training, so the learning curve is significantly shorter and competence in it is easier to maintain.

In the "over-the-needle" method, the cannula must have an ID matched to the OD of the needle, in order for it to enter the vessel with the needle. Therefore, the diameters of cannulas inserted using this technique are limited to the outer diameters of needles that can be used for these purposes, which are usually 21 G-18 G (0.8 mm-1.3 mm). Endovascular procedures often require insertion of instruments having ODs of 8 fr-14 fr (2 mm-4.6 mm) or more.

Since the "over-the-needle" technique is not adequate for placing large bore catheters or sheaths, the Seldinger technique is used in these cases, which as mentioned, include most endovascular interventions.

The WAND, manufactured by Access Scientific of San Diego, Calif., is a device intended to provide a solution for the above drawbacks of the Seldinger technique. This device includes a needle, guidewire, dilator, and sheath in an all-in-one assembly, which is intended for easier and safer over-the-wire sheath insertion. Use of the WAND requires manual advancement of both the guidewire and the sheath by the operator. The WAND mainly addresses safety issues such as needle-stick injury and air embolism, but the technique is still rather complicated and requires significant training.

Expandable sheaths were described in the art in various contexts, mainly for retrieval of large devices such as heart valve delivery systems, aortic balloon catheters etc. usually having self-expanding and balloon expandable components. Such solutions are cumbersome and expensive and are not appropriate for direct over-the-needle vascular access.

Another drawback of existing sheaths related to their having a fixed diameter, is that the arterial puncture site remains dilated to the maximum size for the whole duration of the procedure. The duration of puncture site dilation is one of the factors affecting the chances of its closure. With the current invention, the artery would only be exposed to maximal dilation when the largest instruments are used, while during the rest of the procedure, it will be only slightly dilated. This will increase the successful closure rates and reduce puncture site complication rates.

It is therefore an aspect of the current invention to provide a simple, safe, easy to use, and low cost solution for establishing vascular access.

BRIEF SUMMARY OF THE INVENTION

In one aspect of the invention, improved devices and methods are provided for vascular access, including various mechanical and electronic vessel cannulation devices, some of which comprise both disposable and reusable parts.

In one aspect of the invention, new blunting devices are provided for vessel cannulation needles, as well as improved expandable sheaths for use alone or in combination with the above devices. The blunting devices in accordance with the present invention may be advanced either inside or outside a needle to cover the tip of the needle, thus preventing or reducing the chance of the needle puncturing through the blood vessels.

In one aspect of the invention, a cannulation device is provided, whether mechanical or electronic, that may be capable of (1) advancing a guidewire through a needle, (2) advancing a sheath over a needle, (3) both of the above, together or in succession, (4) deploying other "blunting" elements; and (5) providing an indication to the user, or to an automatic system preforming the cannulation.

An embodiment of the invention is an automatic vessel cannulation device including housing, a lumen, a needle, a sensor, and a blunting device advancing member. The housing may have a distal end with a distal tip and a proximal end. The lumen may pass through the distal end and the proximal end. The needle may be at the distal tip of the housing, wherein the needle having a needle tip. The sensor may be operably coupled to the lumen, wherein the sensor may be configured to detect a physiologic parameter at the needle tip. The blunting device advancing member may be configured to advance a blunting device through the lumen, wherein the blunting device advancing member may be operably coupled to the sensor. The blunting device advancing member may be configured to automatically advance the blunting device when the sensor detects that the physiologic parameter within a pre-determined range. The sensor may be selected from the group consisting of pressure sensors, temperature sensors, conductivity sensors, flow sensors, ultrasound sensors, pH sensors, and optical sensors.

In another embodiment, the vessel cannulation device may further include a trigger mechanism. The trigger mechanism may include a sear and a lever, wherein the trigger mechanism may be configured to release the blunting device advancing member when the sensor detects that the physiologic parameter is within the pre-determined range. The lever may include a hinge located at the distal end of the device, a lever tooth at the proximal end, and a lever base between the hinge and the lever tooth. The sear may be located at the proximal end of the lever and engages the lever tooth. The lever may include a hinge at the proximal end of the device, a lever base at the distal end of the device, and a lever tooth between the hinge and the lever base; wherein the lever operably coupled to and moveable by the sensor. The sear may be located between the proximal end and the distal end of the lever and engages the lever tooth. The distance from the center of the sensor to the hinge is twice the distance from the lever tooth to the hinge.

In some embodiments, the sensor may be a membrane. In some embodiments, the sensor is an electronic sensor. In some embodiments, the sensor may comprise multiple sensors.

In another embodiment, the vessel cannulation device may further include an adjustment mechanism configured to be in contact with the trigger mechanism, wherein the adjustment mechanism adjusts force applied on the lever.

In another embodiment, the vessel cannulation device may further include a CPU. The CPU may be in electrical communication with the sensor and may be configured to execute instructions, wherein when executed, the CPU may be configured to compare the physiologic parameter from the needle tip with predetermined values to determine whether the needle tip has punctured a blood vessel.

In another embodiment, the vessel cannulation device may further include a solenoid in communication with the CPU and connected to the trigger mechanism. The solenoid may activate the trigger mechanism when it is determined that the physiologic parameter from the needle tip matches the predetermined parameter of the blood vessel. The solenoid may be configured to activate outside of a predetermined time window, wherein the predetermined time window for a vein is between 0.05-0.3 seconds, and the predetermined time window for an artery the window is between 0-0.05 seconds.

In another embodiment, the vessel cannulation device may further include an input device for choosing a blood vessel type, wherein the blood vessel type is an artery or a vein. The artery has a predetermined parameter of lower threshold (LTH) of 20 mmHg, upper threshold (UTH) of 300 mmHg, and range of pressure change rate of +/−400 mmHg/sec. The vein has a predetermined parameter of lower threshold (LTH) of 5 mmHg, upper threshold (UTH) of 20 mmHg, and range of pressure change rate of +/−100 mmHg/sec.

In another embodiment, the blunting device advancing member may be coaxial with a large spring. The blunting device and the blunting device advancing member may be covered by a sterile cover within the device.

In another embodiment, the vessel cannulation device may further include a blunting element configured to expand to cover the needle tip when deployed. The blunting element may be stent-like. The blunting element may be selected from the group consisting of an external sheath, an internal sheath, a sandwich sheath, a tip covering sheath, and a tip completing sheath. The internal sheath may be a guidewire with an uncoiled segment or a coiling guidewire. The internal sheath may be deployed by pushing the internal sheath towards the needle tip with a cannulation device. The internal sheath may be configured to be positioned within the needle in its crimped state without substantially blocking the needle lumen.

In another embodiment, the vessel cannulation device may further include a fluid passageway coupling the sensor to the lumen; and wherein the fluid passageway is substantially straight and has an internal diameter of 0.5 mm-2.5 mm, and a length no longer than 4 cm.

In another embodiment, the vessel cannulation device may further include an impact absorbing element for dampening noise and recoil during advancement of the blunting device.

In another embodiment, the vessel cannulation device may further include a cocking mechanism configured to bring the device to a cocked state.

In another embodiment, the vessel cannulation device may further include a cover comprising a safety latch slot and a safety latch.

In another embodiment, the vessel cannulation device may further include a disposable part and of a reusable part.

In another embodiment, the vessel cannulation device may further include a barrier allowing sensing of pressure to be performed while keeping the sensor sterile, and wherein the sensor is reusable.

In another embodiment, the vessel cannulation device may further include a guidance element. The guidance element may be selected from a group consisting of a linear mechanical guide or a rotary mechanical guide. The guidance element may include imaging means. The imaging means may consist of an ultrasound transducer. The ultrasound transducer may be located proximal to the needle tip, and wherein the needle can slide through the transducer. The ultrasound transducer may allow replacement or removal of the needle.

In another embodiment, the vessel cannulation device may further include a mat including: a position sensors, a processor, and an indicator. The processor may be configured to gather ultrasound signals received by the ultrasound transducer simultaneously with the position information from the position sensors. The processor may activate the indicator to signal when the cannulation device is pointed at a blood vessel.

An embodiment of the invention is an automatic system for vessel cannulation including: a mat, a motor, a processor, a vessel cannulation device, and an ultrasound transducer. The mat may have position sensors and a sliding strip. The motor may control a movement of the sliding strip. The processor may be in electronic communication with the mat. The vessel cannulation device as described above, which may be slideably positioned within a housing and pivotally connected to the mat through the sliding strips. The vessel cannulation device includes a needle. The ultrasound transducer may be slideably positioned over the tip of the needle of the vessel cannulation device. The motor may control an orientation of the cannulation device through the sliding strip. The system may scan tissue with the tip of the needle by moving the cannulation device through the ultrasound transducer. The processor may detect a target vessel and advance the vessel cannulation device towards the target vessel until the vessel cannulation device deploys the guidewire within the vessel or until a maximum depth is reached.

An embodiment of the invention is an expandable sheath system including: an expandable outer layer sheath and an inner rigid layer. The expandable outer layer sheath may include longitudinal beams and a step. The inner rigid layer may comprise a bulb and a shoulder which engages with a step of the outer layer sheath. The inner rigid layer sheath may be configured to fit over a needle shaft; and after removal of the needle, the bulb may be collapsed and the inner rigid layer sheath may be removed from the outer layer sheath, while leaving the outer layer sheath in its position within a vessel. The inner rigid layer may be an integral part of the needle.

An embodiment of the invention is an expandable sheath configured to be inserted into a patient's body over a needle. The expandable sheath may comprise rigid longitudinal beams and an expandable elastic layer. The longitudinal beams may be bridged by connections creating a spiral pattern along and around the sheath. The expandable sheath may comprise an external sheath slideably positioned over the expandable outer layer sheath.

The external sheath may include a handle and a support element connecting to the expandable outer layer sheath. The external sheath may be tearable. The expandable sheath may further include a rigid large diameter sheath that is configured to be inserted into the expandable outer layer sheath, to maintain and expand the expandable outer layer sheath.

An embodiment of the invention is an expandable sheath configured to be inserted into a patient's body over a needle, including: a sheath having a single substantially inelastic layer and an inner diameter. In a crimped state, the sheath inner diameter may be in a tight fit with a needle. In the expanded state, the sheath inner diameter may be at least double the sheath inner diameter in the crimped state. The inelastic layer may have multiple micro-corrugations. The inelastic layer may have between 2 and 6 large corrugations folded around the sheath. The expandable sheath may have one corrugation, and wherein this corrugation is folded around the sheath at least once. The expandable sheath may include: the distal end of the inelastic layer comprises a part that is perpendicular to the longitudinal axis of the sheath, and a part that is at an angle relative to the longitudinal axis of the sheath, configured to create a smooth distal taper for the sheath in its crimped state. The expandable sheath may further include a hub configured to overlap with a needle hub.

An embodiment of the invention is a method of using a vessel cannulation system including: calibrating the system by selecting a target vessel type having pre-determined parameters; penetrating a body with a needle to detect a physiologic parameter, wherein the needle is in electronic communication with the system; comparing the physiologic parameter with the pre-determined parameters; and deploying a blunting element into the target vessel if the physiologic parameter is within a range of the pre-determined parameters. The method may further include pushing forward the inner sheath from an inner lumen of the needle towards a distal tip of the needle. The deploying step further comprises activating a solenoid to trigger a trigger mechanism to advance the blunting element. The method may further include placing a mechanical guide on the body with a central marking above an estimated location of the target vessel.

In some embodiments, the blunting element may be configured to be positioned within the needle in its crimped state without substantially blocking the inner lumen, and to cover a distal tip when the blunting element is deployed. The blunting element may be selected from the group consisting of an external sheath, an internal sheath, a sandwich sheath, a tip covering sheath, and a tip completing sheath. The blunting element may be pulled back following deployment to cover the needle tip.

In some embodiments, the mechanical guide may be an ultrasound transducer.

In some embodiments, the calibrating step may comprise choosing a target vessel type, wherein the target vessel type is an artery or a vein. The artery may have a pre-determined parameter of lower threshold (LTH) of 20 mmHg, upper threshold (UTH) of 300 mmHg, and range of pressure change rate of +/−400 mmHg/sec. The vein may have a pre-determined parameter of lower threshold (LTH) of 5 mmHg, upper threshold (UTH) of 20 mmHg, and range of pressure change rate of +/−100 mmHg/sec.

In some embodiments, the penetrating step may include using sensors to detect the physiologic parameter at a needle tip.

In some embodiments, the method may further include inserting a central catheter into the target vessel through the blunting element, wherein the blunting element is an expandable sheath.

In some embodiments, the method may further inserting a peripheral IV catheter into the target vessel through the blunting element, wherein the blunting element is an expandable sheath.

In some embodiments, the method may further drawing blood sampling through the blunting element.

BRIEF DESCRIPTION OF THE DRAWINGS

The foregoing summary, as well as the following detailed description of the invention, will be better understood when read in conjunction with the appended figures. For the purpose of illustrating the invention, the figures demonstrate embodiments of the present invention. It should be understood, however, that the invention is not limited to the precise arrangements, examples, and instrumentalities shown.

FIG. 1A' is a longitudinal cross section of a mechanical cannulation device in accordance with embodiments of the invention, which depicts the guidewire advancement mechanism in a deployed position.

FIG. 2Di is a perspective view of cannulation device 1000.

FIG. 6A is a 3D depiction of a blunting element in accordance with an embodiment of the invention. FIG. 6B is a longitudinal section of a blunting element in a crimped state in the lumen in accordance with an embodiment of the invention. FIG. 6C is a longitudinal section of a blunting element in its deployed state in accordance with an embodiment of the invention. FIG. 6D is an isometric depiction of a blunting element 600 in its deployed state in accordance with an embodiment of the invention.

FIG. 7A is a longitudinal section of a blunting element in its crimped state in accordance with an embodiment of the invention. FIG. 7B is a longitudinal section of a blunting element in its deployed state in accordance with an embodiment of the invention.

FIG. 8A is a 3D depiction of a blunting element in accordance with an embodiment of the invention. FIG. 8B is a longitudinal section of a blunting element in its crimped state in accordance with an embodiment of the invention. FIG. 8C is a longitudinal section of blunting element in its deployed state in accordance with an embodiment of the invention. FIGS. 8D and 8E are 3D drawings showing the same as FIGS. 8B and 8C, respectively.

FIG. 9A is a longitudinal section of a blunting element in its crimped state in accordance with an embodiment of the invention. FIG. 9B is a longitudinal section of a blunting element in its deployed state in accordance with an embodiment of the invention. FIGS. 9C and 9D are 3D drawings showing perspective views of FIGS. 9A and 9B, respectively.

FIG. 10A is a longitudinal section of a blunting element in its crimped state in accordance with an embodiment of the invention. FIG. 10B is a longitudinal section of blunting element 900 in its deployed state in accordance with an embodiment of the invention. FIG. 10C is a 3D drawing of a deployed blunting element without a needle in accordance with an embodiment of the invention. FIG. 10D is a 3D drawing of a deployed blunting element with a needle in accordance with an embodiment of the invention.

FIG. 11A is a longitudinal section of a blunting element in its crimped state in accordance with an embodiment of the invention. FIG. 11B is a longitudinal section of a blunting element in its deployed state in accordance with an embodiment of the invention.

FIG. 13A is a simplified 3D drawing of a cannulation device having a transducer in accordance with an embodiment of the invention. FIG. 13B shows a transducer used as part of a cannulation device in embodiments of the invention. FIGS. 13C and 13D are simplified side views of cannulation devices having a transducer in accordance with embodiments of the invention.

DETAILED DESCRIPTION

The invention relates to devices and methods for the cannulation of body lumens, in particular blood vessels, with the goal of placing intravascular catheters such as Central Venous Catheters (CVCs), Peripherally Inserted Central Catheters (PICVs), midlines, and Peripherally Inserted Venous Catheters (PIVCs). The invention also relates to devices and methods for temporary vessel cannulation without placing an indwelling catheter, with the goal of blood sampling, cardiovascular monitoring, or administration of drugs or fluids. Various body lumens and/or cavities and/or various indications for use involving blood, cardiovascular, drugs or fluids are contemplated.

Mechanical Vessel Cannulation Device

Figure 1A:
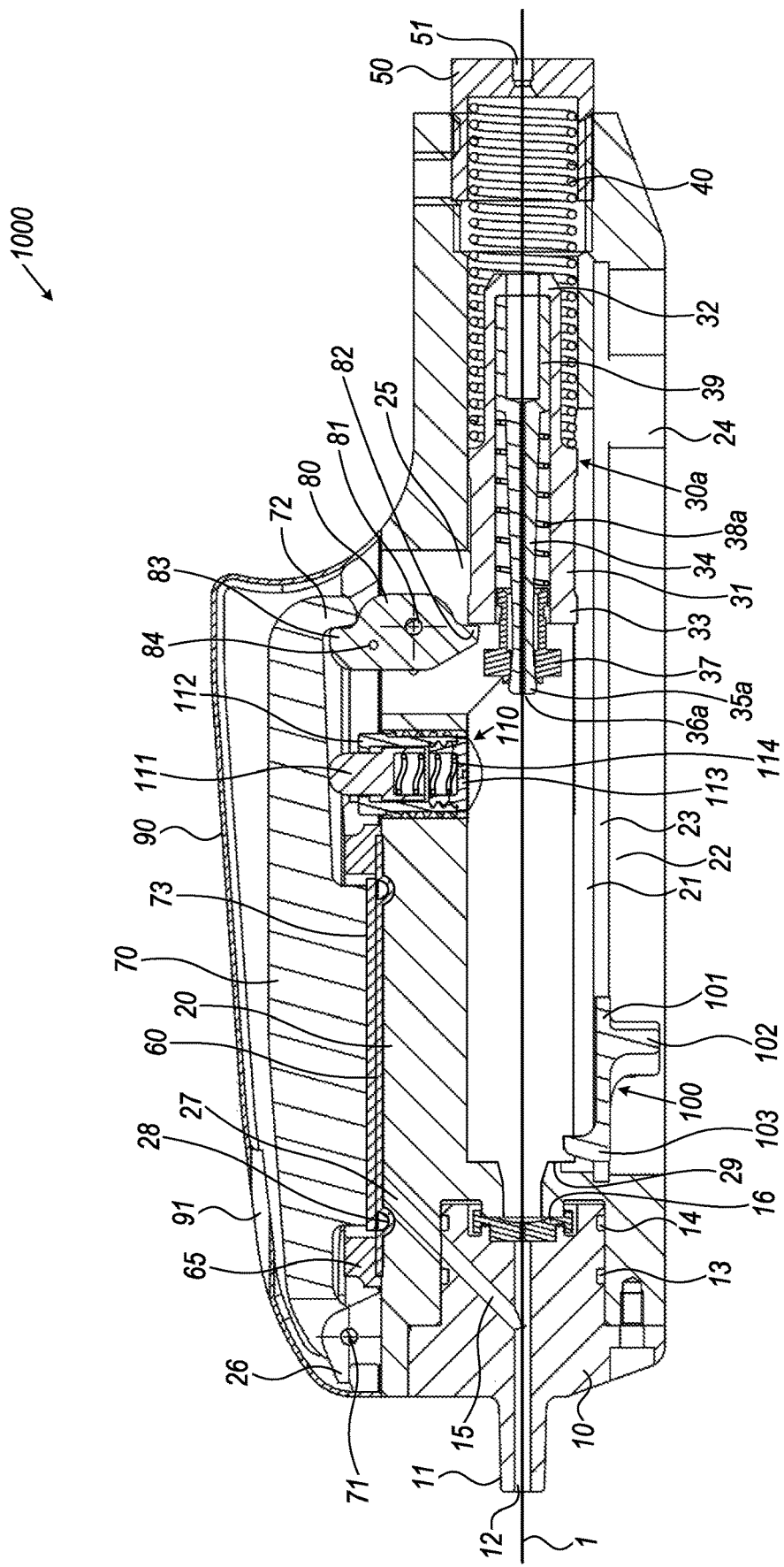
FIG. 1A is a longitudinal cross section of a mechanical cannulation device in accordance with embodiments of the invention, which depicts the guidewire advancement mechanism in a cocked position.
Figure 1A:
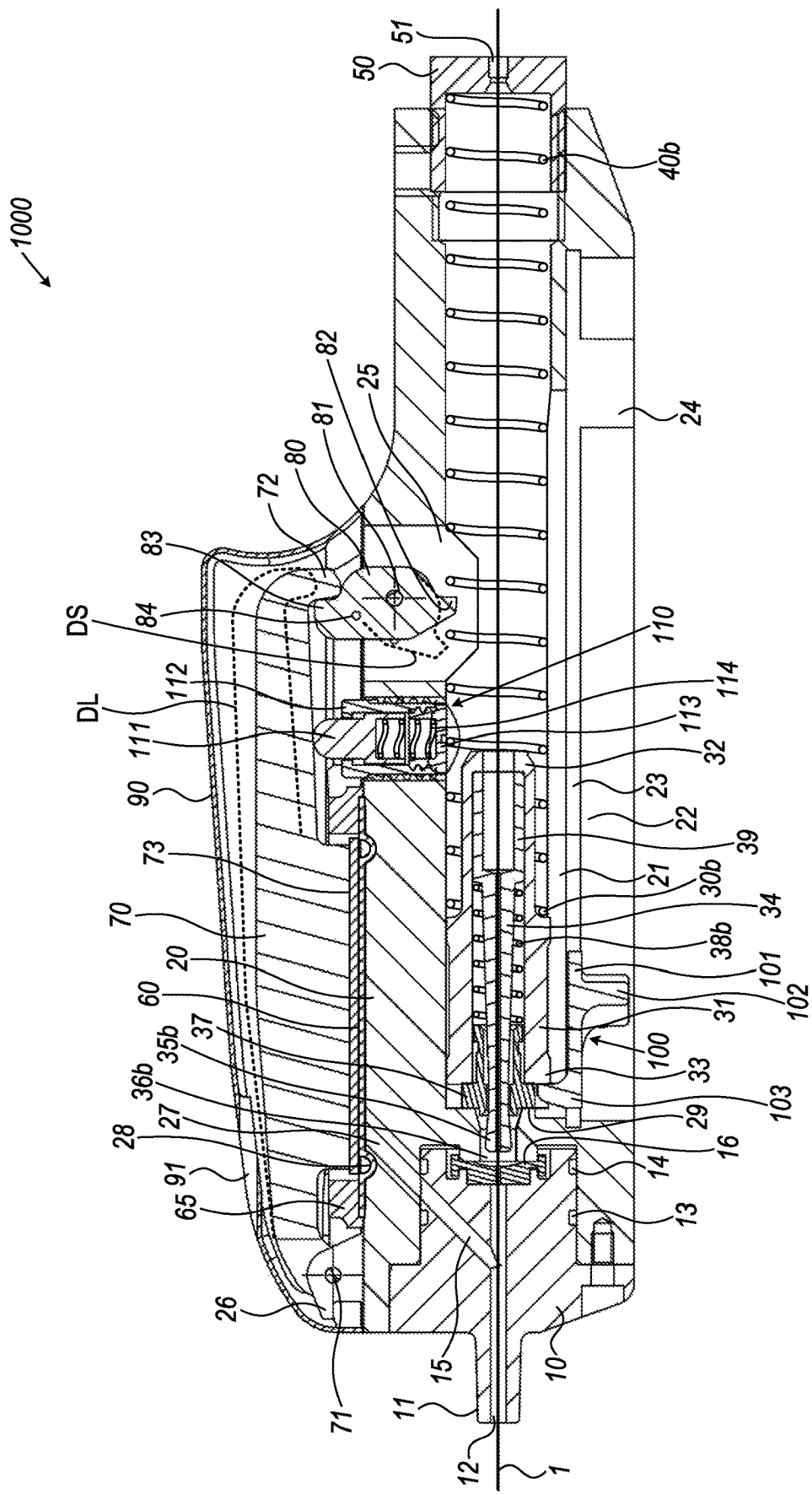
Figure 1B:
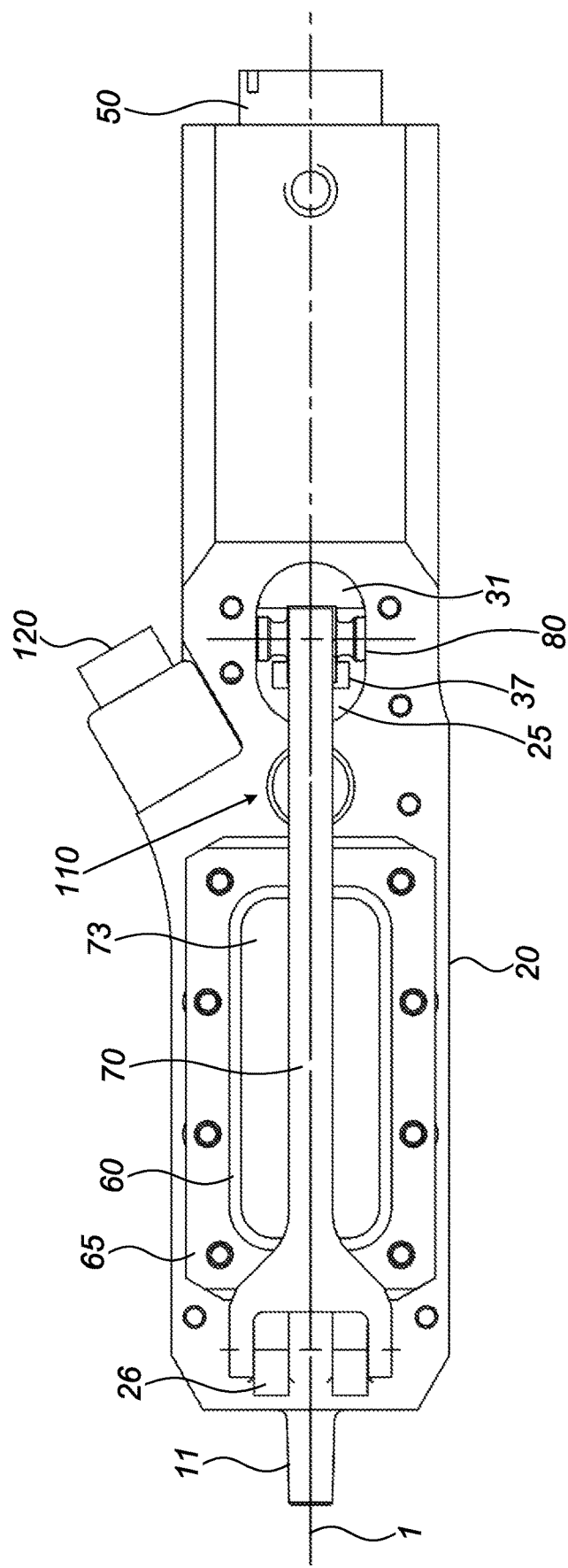
FIG. 1B is a top view of a mechanical cannulation device in accordance with embodiments of the invention.

FIG. 1A is a longitudinal cross section of the mechanical cannulation device 1000 of the invention, which depicts the guidewire advancement mechanism in a cocked position. FIG. 1A' is a longitudinal cross section of a mechanical cannulation device in accordance with embodiments of the invention, which depicts the guidewire advancement mechanism in a deployed position. FIG. 1B is a top view of FIG. 1A. In these figures, distal refers to the left side, and proximal refers to the right side.

More particularly, FIG. 1A is a longitudinal section of device 1000 along its midline, which passes along the line marked 1 in the top view shown in FIG. 1B. FIG. 1A shows device 1000 which may include from left to right the following main parts: needle adapter 10, seal 16, body 20, guidewire advancement mechanism 30a (shown in cocked position), large spring 40, and backplate 50. Each of the main parts has a central lumen and guidewire 1 may be slideably positioned within the central lumen of all the above parts.

Device 1000 may further include membrane 60, lever 70, sear 80, cover 90, cocking handle 100, and adjustment element 110. Each main part of device 1000 is further described below.

Needle adapter 10 may include luer adapter 11, lumen 12, o-ring slots 13 and 14, distal fluid passageway 15, and seal 16, which may optionally be an integral part of needle adapter 10. O-rings may be placed in o-ring slots 13 and 14 to prevent pressure within fluid passageways from escaping around needle adapter 10.

Body 20 may include slider slot 21, cocking handle slot 22, handle groove 23, insertion groove 24, opening 25, protrusion 26, proximal fluid passageway 27, membrane groove 28, and stopper 29. Distal fluid passageway 15 and proximal fluid passageway 27 may be connected and may be in fluid communication with lumen 12 such that when fluid enters lumen 12 at the distal end, fluid may travel to distal fluid passageway 15 and to proximal fluid passageway 27.

Guidewire advancement mechanism 30 (shown as 30a in the cocked position in FIG. 1A and 30b in the deployed position in FIG. 1A') may include slider 31, which may have slider proximal end 32 and slider distal end 33, gripper 34, which may have gripper distal end 39, gripper distal end 35, and gripper lumen 36, ring 37, and small spring 38. Gripper 34 may comprise a tubular structure, longitudinally divided into two or more parts. Gripper distal end 35 may comprise the distal ends of these longitudinal parts, which may be made with a tendency to expand radially. Small spring (or "gripper spring") 38 may typically be a compression spring having a force of 1-2 N at its free state. In an embodiment, the gripper spring 38 may include a free length of approximately 20 mm, a solid length of 9.5 mm, 8 active coils out of 20 total, 0.45 mm diameter ss 312 wire, and a coil outer diameter of ~4.5 mm. Ring 37 may be slideably disposed within slider 31, and over gripper 34, such that when positioned over gripper distal end 35, it may prevent radial expansion of gripper distal end 35, thus decreasing the diameter of gripper lumen 36 (marked 36a), and gripping wire 1. Conversely, when ring 37 is pushed proximally relative to slider 31, distal end 35 of gripper 34 may radially expand, enlarging the diameter of gripper lumen 36 (marked 36b), and releasing guidewire 1.

As shown in FIG. 1A, when in its cocked (proximal) position, guidewire advancement mechanism 30a may comprise compressed gripper lumen 36a, gripping guidewire 1 so that it can be advanced by the device 1000. More particularly, in the cocked position, with a guidewire loaded within gripper lumen 36a, ring 37 may be pushed by small spring 38a toward distal end 35a of gripper 34 such that 37 protrudes distally beyond slider distal end 33, and compresses the longitudinal part which includes gripper end 35a.

Large spring 40 is positioned between guidewire advancement mechanism 30 and backplate 50, such that in the cocked position large spring 40a is compressed and exerts forward pushing force on guidewire advancement mechanism 30 relative to backplate 50. In the deployed position, large spring 40 exerts a smaller force on guidewire advancement mechanism 30b, but such a force that is sufficient to compress small spring 38b and cause release of guidewire 1 from gripper 34. Large spring (or "slider spring") 40 may be a compression spring having a force of ~10 N at its solid length and ~3 N at the deployed state, which may typically be at a length of ~78 mm. Typical specifications may further include a free length of approximately 98 mm, a solid length of ~33 mm, 34 active coils, 0.8 mm diameter ss 312 wire, and a coil outer diameter of ~9.7 mm.

Backplate 50 has a through hole 51 for passage of guidewire 1.

Membrane 60 may be a thin membrane having an oblong fold which fits into membrane groove 28 of body 20. Membrane 60 may be held in place by frame 65 which presses membrane 60 onto body 20. Proximal fluid passageway 27 may be in direct contact with membrane 60 such that when fluid enters proximal fluid passage way, membrane 60 may sense the change of pressure. Membrane 60 may be a diaphragm.

Lever 70 is an elongate member with a lever hinge 71 running through protrusion 26 of body 20, a lever tooth 72, and a lever base 73. Lever base 73 fits inside membrane frame 65, and sits flat on membrane 60 while deflated. If pressurized fluid enters between membrane 60 and body 20 via fluid passageways 15 and 27, membrane 60 can inflate and rise, and lever 70 can rotate around lever hinge 71, such that lever tooth 72 moves upwards. The exact angle of the contact surface of lever tooth 72 with sear 80, relative to the line perpendicular to the long axis of slot 21, can be very important. This angle, combined with other parameters which include the position of hinge 71, position of upper sear tooth 83, position of lever tooth 72, govern the size and direction of a moment which tends to turn lever arm 70 around hinge 71. To keep this moment at a clockwise direction, the resultant reaction force of sear 80 through lever 70 may be directed above hinge 71. The distance between the vector of this force and the hinge multiplied by the vector size, is the rotating moment. The desirable rotating moment is governed by the location of the membrane relative to hinge 71, the size of membrane 60, and the desired triggering fluid pressure. Adjustment mechanism 110 also effects, and preferably adjusts, the desired rotating moment. In some embodiments, the resultant rotating moment from the sear reaction on lever tooth 72 can be between 1250 and 7500 gf-mm (gram force millimeter).

Sear 80 has a hinge 81 running through body 20, and around which it can rotate. Sear 80 also has lower sear tooth 82, upper sear tooth 83, and sear hole 84. Sear 80 is positioned inside opening 25 of body 20, such that lower sear tooth 82 protrudes into slot 21 when sear is upright as in FIG. 1A, and no part of sear 80 protrudes into slot 21 when it is sufficiently rotated to either side (approximately 30-90 degrees).

A spiral spring (not shown) may be placed with its coils around sear hinge 81, one leg in sear hole 84, and the other leg in a hole in body 20, such that sear 80 can be slightly rotated around sear hinge 81, but tends to flexibly return to the same angle relative to body 20. This allows moving guidewire advancement mechanism 30 along slot 21 from the deployed (distal) position to the cocked (proximal) position without sear 80 obstructing its passage.

Cover 90 can be a thin walled shell covering the upper part of device 1000, including lever 70, membrane 60, sear 80, and adjustment mechanism 110. Cover 90 may prevent a user from inadvertently touching the sensitive parts of device 1000 and interfering with device operation. It may also provide convenient grips for holding the device. Cover 90 may optionally include cover slot 91. A safety latch (not shown) in the form of a rigid, semi-rigid, or flexible thin rod may be placed through cover slot 91, to press lever 70 clockwise, and enable cocking of device 1000 as explained below.

Cocking handle 100 may comprise plate 101, handle 102, and hook 103. Plate 101 may fit into handle groove 23, but may be slightly wider than cocking handle slot 22, and therefore needs to be inserted into handle groove 23 via insertion groove 24. Cocking handle 100 may be placed with hook 103 distal to guidewire advancement mechanism 30, so that when cocking handle 100 may be moved proximally, hook 103 may pull guidewire advancement mechanism 30 proximally.

Optional adjustment element 110 may include knob 111, casing 112, cap 113, and knob spring 114. Knob 111 and knob spring 114 may enclose within casing 112 and cap 113, such that knob 111 may push upwards by knob spring 114. Casing 112 may have an external thread with body 20, and an internal thread with cap 113. Adjustment element 110 may be placed in an opening in body 20 such that knob 111 may apply upwards force on lever 70, reducing the force required for release of guidewire advancement mechanism 30, thereby reducing the blood pressure threshold at which device 1000 may deploy. The force applied by adjustment mechanism 110 may be adjusted by changing knob spring 114, by screwing cap 113 tighter or weaker, or by screwing casing 112 upward or downward relative to body 20.

Adjustment element 110 may have an end force of 50-300 grams, preferably 100-200 grams, and a travel of 1-5 mm, preferably 2-4 mm.

Access to adjustment element 110 may be from either the bottom part of device 1000, for example by inserting a screwdriver through slot 22 and turning cap 113, or by removing cover 90, and rotating casing 112, which may be accessed from either side of lever 70. These actions may be performed as part of the precalibration process described below.

A needle (not shown) may be coupled to the luer adapter 11 of needle adapter 10 at the distal end of device 1000. The needle may be fluidly coupled to the distal fluid passageway 15 and/or may include a lumen for passing guidewire 1 and fluid. Device 1000 may also be adapted to receive bodily fluid through the needle into the anterior lumen.

An internal or external sheath (not shown) or other blunting elements may also be coupled to the needle. Sheaths and blunting elements are further discussed below.

FIG. 1A' shows device 1000 in its deployed state. More particularly FIG. 1A' is a longitudinal section of device 1000 along its midline, which passes along the line marked 1 in the top view shown in FIG. 1B. Shown in FIG. 1A' are the same elements shown in FIG. 1A with the following differences: advancement mechanism 30 is shown in its distal, deployed state, 30b, and large spring 40 is shown in its deployed state, 40b.

At the moment of deployment, membrane 60 may extend upwards and push lever base 73 and lever 70 upwards, so that lever tooth 72 may move beyond the edge of sear tooth 83, and allow sear 80 to rotate clockwise, allowing advancement mechanism 30 to be pushed distally by large spring 40 and advance guidewire 1. The extent to which lever 70 may move upwards during deployment is marked by dashed line DL, and the extent to which sear 80 may rotate is marked by dashed line DS.

As shown in FIG. 1A', when guidewire advancement mechanism 30b is in its deployed (distal) position, large spring 40b may push ring 37 against stopper 29 of body 20, so that ring 37 may be pressed into slider 31, and distal end 35b of gripper 34 may protrude distally beyond ring 37, such that its longitudinal parts may expand radially and enlarge the diameter of gripper lumen 36a, thus releasing guidewire 1 to slide undisturbed within gripper lumen 36b.

Moving now to FIG. 1B, which is a top view of device 1000 with cover 90 removed, the following parts are seen, from left to right: guidewire 1, luer adapter 11, body 20, protrusion 26, lever 70, membrane 60, membrane frame 65, lever base 73, adjustment mechanism 110, optional fluid port, opening 25, ring 37, sear 80, slider 31, and backplate 50. Fluid port 120 may be a port in fluid communication with the area between membrane 60 and body 20, and which may consist of a unidirectional valve, and may include a luer connector or any other connector. This port may be used to fill fluid in the fluid passageways, either immediately prior to use, or as part of device assembly and preparation during manufacturing. Also, this port may be useful for cleaning the device after use.

In operation, device 1000 may be precalibrated, it may be cocked before use, and then used to access a blood vessel.

Figure 1C:
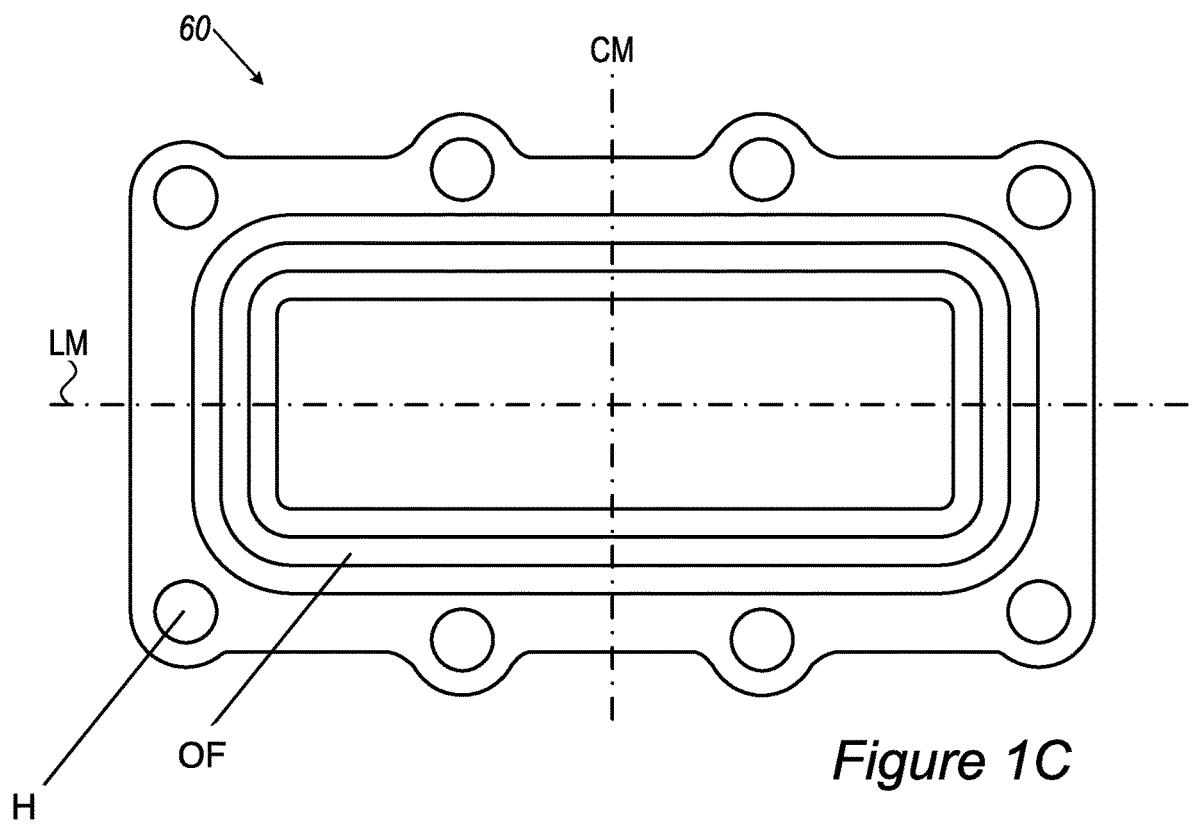
FIG. 1C is a top view of membrane 60 of a mechanical cannulation device in accordance with embodiments of the invention.

FIG. 1C is a top view of an embodiment of membrane 60 of device 1000. More particularly, FIG. 1C shows membrane 60, which may be substantially oblong, although it may have other, preferably elongate shapes, such as elliptical. Such shapes are compatible with the general elongate structure of device 1000. Membrane 60 may typically comprise oblong fold OF, which may be designed to fit within membrane groove 28 of body 20. Membrane 60 may typically extend around oblong fold OF, to enable it to tightly and sealably be attached to body 20 by frame 65, preventing leakage around its edges. Typically, membrane 60 may further comprise multiple holes H which may allow tightening frame 65 to body 20, using screws, pins, pegs, or other components as known in the art. Longitudinal midline LM and cross-section midline CM are further show in FIG. 1C.

Figure 1D:
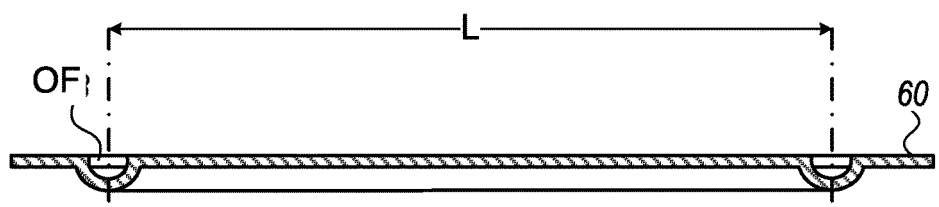
FIG. 1D is a longitudinal mid-section of a membrane of a mechanical cannulation device in accordance with embodiments of the invention.

FIG. 1D is a longitudinal section view of membrane 60 of device 1000. More particularly, FIG. 1D is a longitudinal section along line LM shown in FIG. 1C. Oblong fold OF is shown, defining an effective membrane length L.

Figure 1E:
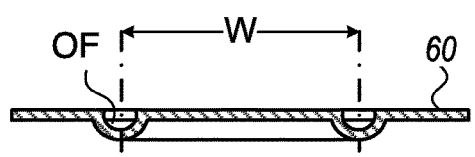
FIG. 1E is a cross section of a membrane of a mechanical cannulation device in accordance with embodiments of the invention.

FIG. 1E is a longitudinal section view of membrane 60 of device 1000. More particularly, FIG. 1E is a cross section along line CM shown in FIG. 1C. Oblong fold OF is shown, defining an effective membrane width W.

Membrane 60 may typically be made of a thin layer of elastic material such as silicone, polyurethane, latex, etc. Membrane 60 may typically have a durometer of 5 to 30 shore A, preferably 10 to 20 shore A. The thickness of membrane 60 may typically range between 0.05 mm and 0.5 mm, preferably 0.2 to 0.4 mm.

Effective membrane length L and effective membrane width W define the effective membrane surface area, which define the force it may apply over lever base 73. Oblong fold OF of membrane 60 may allow membrane 60 to rise without being elastically stretched. This may be beneficial as it may reduce the pressure required for triggering the trigger mechanism of device 1000. If membrane 60 did not have OF, pressure would initially need to work against the elasticity of membrane 60, stretch it, and only then would it act upon lever base 73.

Precalibration

The needle and guidewire to be used with device 1000 are assembled on the device. A needle is placed with its hub over luer adapter 11, and guidewire 1 is loaded through lumen 12, guidewire advancement mechanism 30, and hole 51, and the device is in a cocked position. Increasing fluid pressures may be intermittently applied to device 1000 through the needle, and the pressure at which deployment occurs instantaneously is noted as the threshold pressure. Adjustment mechanism 110 may be adjusted as described above to increase or decrease the threshold pressure.

Cocking Action

During cocking action, a safety latch as described above may preferably be placed in cover slot 91 to hold lever 70 in the proper position. Guidewire 1 may be loaded through a needle (not shown), lumen 12, guidewire advancement mechanism 30, and hole 51, and may be positioned such that its distal tip protrudes approximately 2-5 cm distal to the distal tip of the needle. Cocking handle 100 may be moved proximally by the user, such as by placing a user's thumb in front of handle 102 and pulling it proximally to a marking on body 20, or all the way until large spring 40 may become completely compressed. At that point, guidewire advancement mechanism 30a may be proximal to sear 80, and cocking handle 100 may be returned forward to its distal location. One or more additional spring may be added to perform this return movement by releasing the handle. As guidewire advancement mechanism 30 is pushed distally by large spring 40, slider distal end 33 may engage lower sear tooth 82, and may attempt to rotate sear 80 clockwise. Since a safety latch may be placed inside cover slot 91, lever 70 may be held in a position such that lever tooth 72 engages with upper sear tooth 83. Thus, guidewire advancement mechanism 30 may remain in its cocked position, and device 1000 may become ready for use. The safety latch may then be removed from the cover slot 91.

Vascular Access

An over the needle sheath in accordance with the present invention may optionally be placed over the needle of device 1000, preferably prior to cocking the device.

The target vessel and puncture area may be chosen, optionally using imaging, and the skin may be prepped as customary. The safety latch may be removed prior to skin puncture.

The user may then puncture the skin and attempt to puncture the target vessel. Once a vessel with intravascular pressure above a precalibrated threshold pressure is punctured, pressure may be transmitted to membrane 60 which may rise and push lever 70 upward away from the advancement mechanism and automatically triggering release of guidewire advancement mechanism 30 by allowing sear 80 to rotate sufficiently clockwise, thus advancing guidewire 1 into the vessel, and preventing the needle from exiting through the back side of the vessel. The user can then further advance guidewire 1 into the vessel, slide the over the needle sheath into the vessel, and remove device 1000 and guidewire. As further provide below, the needle sheath may be an external sheath over the needle or an internal sheath within the needle. In some embodiments, the needle sheath may be an expandable sheath to aid the placement of central catheter.

Additional features of the current invention are described below.

Fluid Passageways

For optimal function of device 1000, fluid passageways 15 and 27 should be as short and straight as possible, without bends, and with a diameter that is small enough to keep total volume small, but large enough so as not to increase resistance to fluid pressure transmission. For example, in some embodiments, the fluid passageways 15 and 27 may have a capacity for 5 cubic millimeters to 25 cubic millimeters total fluid, or from 5 to 20 cubic millimeters, or from 5-10 cubic millimeters. In some embodiments, the fluid passageways diameter may be 0.5 mm-2.5 mm, preferably 0.75 mm-2 mm, and their length may be less than 4 cm, preferably less than 2.0 cm. Prefilling the fluid passageway with a biological acceptable fluid, such as saline, may further improve function of the device.

Trigger Mechanism

The trigger mechanism includes lever 70 and sear 80. In order to keep response times low, these parts should have low inertia. Additionally, in order to achieve high accuracy, parts should be rigid and have low friction, and be built to tight tolerances. Possible materials for these parts may include, among others, aluminum, stainless steel, titanium, and PEEK. Polishing of the contact areas between lever 70 and sear 80 may further decrease friction and reduce triggering force and pressure threshold.

Adjustment Mechanism

The adjustment mechanism adds a rotating moment to the lever, changing the moment balance in such a way that either reduces or increases the required force from the membrane to trip the trigger mechanism.

The adjustment mechanism may include adjustment element 110 and be used as described above in the precalibration section. The adjustment mechanism may alternatively comprise other elements that may apply forces to the lever or sear from other directions, for example from cover 90 downwards. Regardless of the exact mechanism of adjustment mechanism, it may comprise a scale, which may allow recording of adjustments and comparison between devices.

In some embodiments, adjustments of the adjustment mechanism may be performed during manufacturing. Preferably, tolerances of the system are such that once a specific model of device is manufactured and precalibrated, all similar devices may be adjusted to the same settings, and will all function similarly. Alternatively, each device may be precalibrated individually during manufacturing.

Advancement Mechanism

Advancement mechanism 30 described above, may allow for guidewire 1 to be gripped by gripper 34 at all times, until the end of the deployment stroke. Once fully deployed, the guidewire may be released and can be moved freely by the user. The advantage of such an advancement mechanism is that advancement of the wire is controlled, i.e., it is known that the wire may advance at least the distance of the stroke of the advancement mechanism, 2-10 cm, preferably 3-6 cm. In addition, at the end of motion, the guidewire may be moved without friction with the device, so the user can both assess that it is within a vessel, and decide to insert it further or pull it back if required.

Conversely, other advancement mechanisms described in the art may release the guidewire at an earlier point during advancement, which may decrease control over the insertion distance.

Noise/Recoil Dampening

In an embodiment, at least the distal end of ring 37 is made of, or is covered by, a soft material such as silicone. This may dampen the impact that may occur between ring 37 and stopper 29 of body 20 when device 1000 deploys and guidewire advancement mechanism 30 moves to its distal position (30*b*). In another embodiment, such soft material may be positioned on stopper 29, instead of, or in addition to, over ring 37. Such impact absorbing elements may optionally further have a shape improving their impact absorbing properties such as a c-shaped cross section or accordion-like longitudinal section.

Alternatively or additionally, the impact-absorbing element may be made of an aerated material such as sponge, and may have an elongate shape, for example a cylindrical shape.

In yet another embodiment, the impact absorbing element and seal 16 may be connected to each other or made as one part.

Lowering the mass of guidewire advancement mechanism 30 is an additional measure for decreasing recoil and noise during deployment.

Cocking Mechanism

The above described cocking mechanism has the advantage of simplicity in both mechanism and in the cocking action performed by the user. In addition, no parts that move during deployment are exposed, so that the user may not inadvertently interfere with movement of the advancement mechanism.

Preferred components for this mechanism include sear 80 (protruding into slot 21 only in the cocked position), its springy recoil to an angle where sear tooth 82 protrudes into the slot 21, preferably ~45 degrees in the direction from distal superior to proximal inferior (the angle between sear teeth longitudinal axis to slot 21 longitudinal axis), downward (clockwise) force over lever 70 (in some embodiments exerted by the above described safety latch, but can be exerted by different safety latches), and the cocking handle.

More particularly, a spiral spring for ensuring the sear tooth angle that was described above, having coils around sear hinge 81, one leg in sear hole 84, and the other leg in a hole in body 20, such that sear 80 can be slightly rotated around sear hinge 81, but tends to flexibly return to the same angle relative to body 20. This spiral spring may typically be a torsion spring with two legs, having a torque force of ~4.2 Nmm at its free state. Typical specifications may further include 2.5 coils, 0.4 mm diameter ss 312 wire, and a coil outer diameter of ~5.4 mm.

Cover

Described above, cover 90 can be made of various materials such as ABS, polycarbonate, other plastics, stainless steel, aluminum, or other metals, or any other appropriate material, or combination of these. Beneficially, it may be transparent to allow viewing of mechanism movement. It may be connected to body 20 using glue, screws, a snap design or combination thereof.

The current design incorporates a safety latch or inserted pin into the cover 90 in cover slot 91. Said safety latch preventing inadvertent actuation of the trigger mechanism.

Disposable/Reusable

In many situations, it may be beneficial that the parts of the device in contact with the patient's blood are disposable, while those not in contact with blood remain reusable.

Four preferred embodiments of a mechanical vessel cannulation device consisting of a combination of reusable and disposable parts are shown in FIGS. 2A-2D.

Figure 2A:
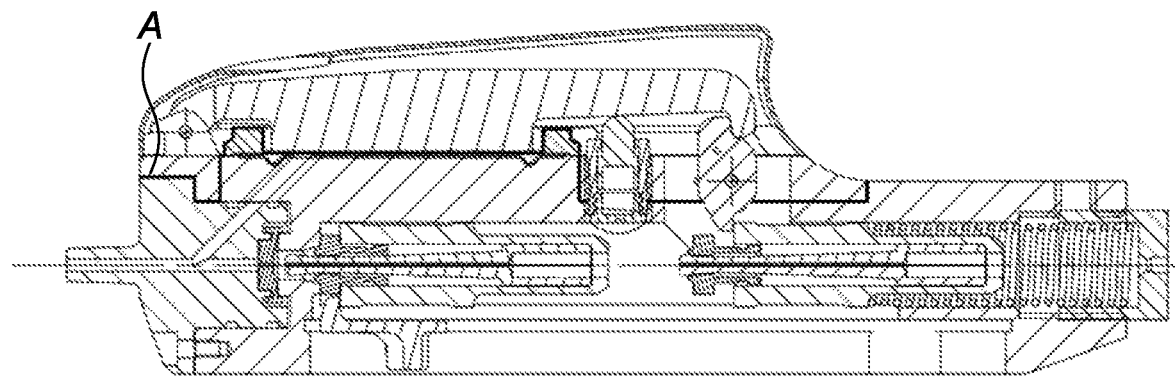
FIG. 2A is a longitudinal cross section of a mechanical cannulation device in accordance with one embodiment of the invention.

FIG. 2A is a longitudinal cross section of device 1000 wherein lever 70, sear 80, and adjustment mechanism 110 are reusable, and all other main components are disposable. Line A is a possible separation line dividing device 1000 into a reusable section (above line A), and a disposable section (below line A). The two parts may be slideably positioned over each other, and locked together using a latch, a snap element, or other means as known in the art. In this embodiment, lever 70 and sear 80 that require high precision may be manufactured using expensive materials and processes. However, large spring 40 and advancement mechanism 30 are still disposable, which adds to the disposable cost.

Figure 2B:
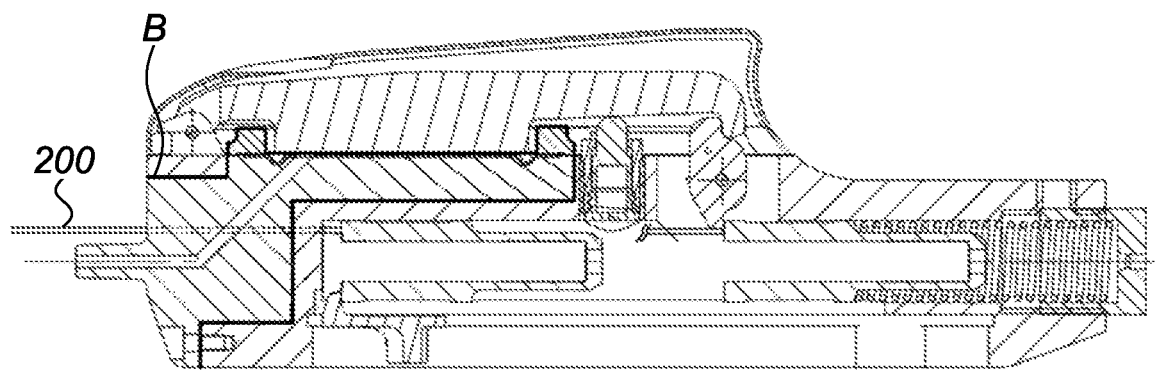
FIG. 2B is a longitudinal cross section of a mechanical cannulation device in accordance with another embodiment of the invention.

FIG. 2B is a longitudinal cross section of device 1000 wherein lever 70, sear 80, adjustment mechanism 110, large spring 40, advancement mechanism 30, and body 20 are reusable, and all other main components are disposable. Line B is a possible separation line dividing device 1000 into a reusable section (to the right of line B), and a disposable section (to the left of line B). In this embodiment, a guidewire is not used; instead, an external sheath may be used to blunt the needle. It may be pushed forward by push element 200, which is part of the disposable section, and may be advanced by advancement mechanism 30. In this embodiment a valve is not required as no element is pushed through the needle.

Figure 2C:
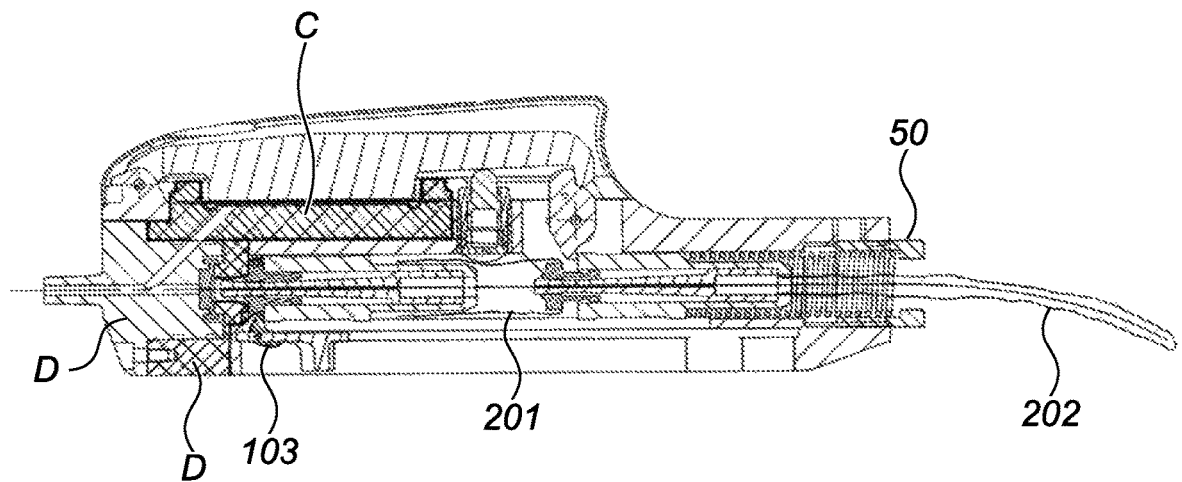
FIG. 2C is a longitudinal cross section of a mechanical cannulation device in accordance with an alternate embodiment of the invention.

FIG. 2C is a longitudinal cross section of device 1000 wherein lever 70, sear 80, adjustment mechanism 110, large spring 40, slider 31, and body 20 are reusable, and all other main components are disposable. Part C includes membrane 60, membrane frame 65, and that part of body 20 supporting membrane 60 and including proximal fluid passageways 27. Part C may be slid in from the side and locked to body 20. Part D comprises needle adapter 10, seal 16, and stopper 29. Parts of advancement mechanism 30, including ring 37, gripper 34, and small spring 38, together with guidewire 1 and part D are plugged into device 1000 from its front (distal) side. A nylon sheath 201 connects stopper 29 with ring 37, and another nylon sheath 202 covers guidewire 1 from the proximal end of gripper 34 to the proximal end of guidewire 1, to keep guidewire 1 sterile at all times. In this embodiment, opening 51 of backplate 50 is made larger to accommodate passage of sheath 202 and guidewire 1. In case slider 31 is made disposable such that all advancement mechanism 30 is disposable, hook 103 of cocking handle 100 is able to fold to one side, enabling insertion of advancement mechanism 30, and still enabling pulling it back for cocking device 1000.

Figure 2D:
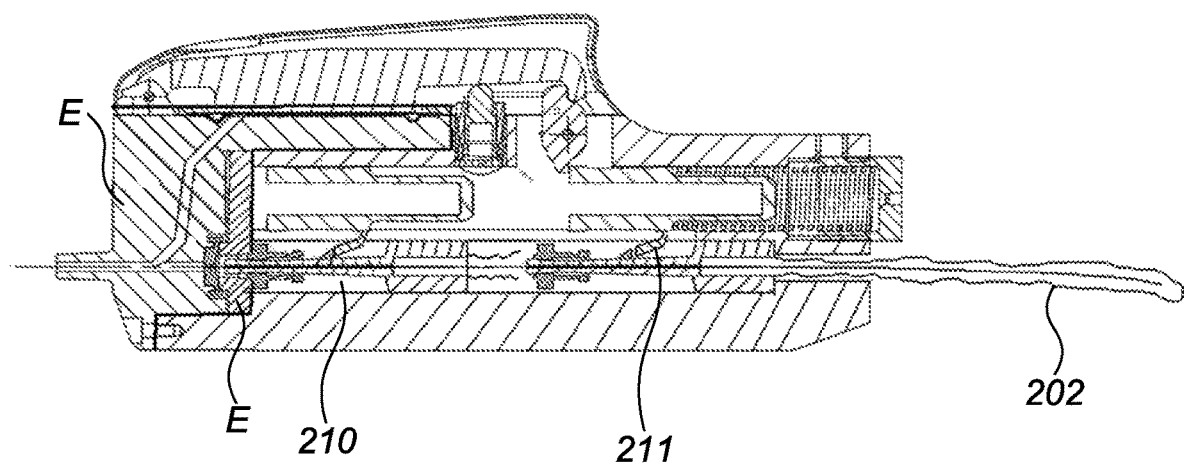
FIG. 2D is a longitudinal cross section of a mechanical cannulation device in accordance with yet another alternate embodiment of the invention.
Figure 2D:
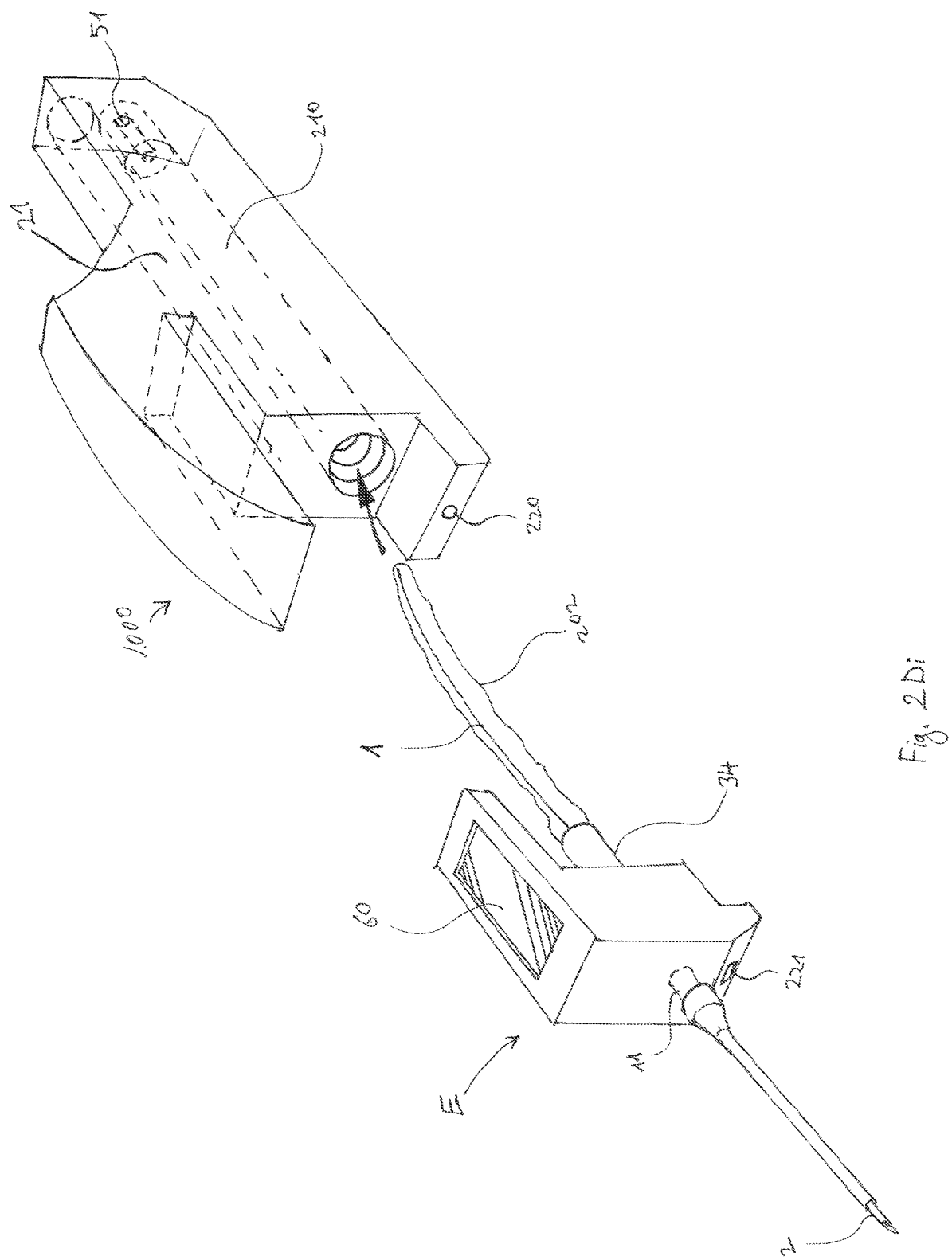

FIG. 2D is a longitudinal cross section of device 1000 wherein lever 70, sear 80, adjustment mechanism 110, large spring 40, slider 31, and body 20 are reusable, and all other main components are disposable. This embodiment has two separate slots for advancement. Slot 21, wherein slides slider 31 pushed by large spring 40, and a separate slot 210, wherein slides gripper 34, pushed by arm 211 extending from slider 31. An embodiment of a device 1000 comprising disposable and reusable components as described in FIG. 2D, is shown in FIG. 2Di.

More particularly, FIG. 2Di is a perspective view of cannulation device 1000 having a disposable component E comprising membrane 60, membrane frame 65, and that part of body 20 supporting membrane 60, proximal fluid passageways 27, needle adapter 10, seal 16, and stopper 29. Needle 2 is seen connected to luer adapter 11 and extending distally from it. Guidewire 1 is seen protruding proximally from gripper 34, and covered by sterile cover 202. A socket 220 is located in the front of body 220. Whereas in other embodiments socket 220 may comprise a thread enabling connection of needle adapter 10 to body 20 using a screw, in some embodiments such as the one in FIG. 2Di, a spring loaded pin 221 in the disposable part E may be used to temporarily connect part E to body 20. Alternatively other easily removable connecting means as known in the art may be used such as various forms of buttons and fasteners.

Part E includes membrane 60, membrane frame 65, and that part of body 20 supporting membrane 60, proximal fluid passageways 27, needle adapter 10, seal 16, and stopper 29. Parts of advancement mechanism 30, including ring 37, gripper 34, and small spring 38, together with guidewire 1 and part E are plugged into device 1000 from its front (distal) end. Nylon sheath 202 covers guidewire 1 from the proximal end of gripper 34 to the proximal end of guidewire 1, to keep guidewire 1 sterile at all times. In use, part E complete with the needle and guidewire is plugged into device 1000 from its front end as shown by the arrow in FIG. 2Di, such that guidewire 1 covered by sterile cover 202 protrudes out of hole 51 at the back end of the device.

A similar combination of disposable and reusable parts may be used for some electronic variations of the device 1000 which are described below.

By separating slider 31 from gripper 34 such that large spring 40 is not coaxial with the needle and guidewire 1, it is possible to make almost all of the advancement mechanism including large spring 40 reusable, thus lowering the cost of the disposable parts, while keeping the blunting element (in this case a guidewire, but possibly a different intravascular element) sterile.

In FIG. 2D slot 21 is depicted above slot 210, but these can be one next to the other or in any other configuration.

A cocking handle is not shown in FIG. 2D, but it can be placed for example on the side of slot 21.

Aft Hinge Design

Figure 2E:
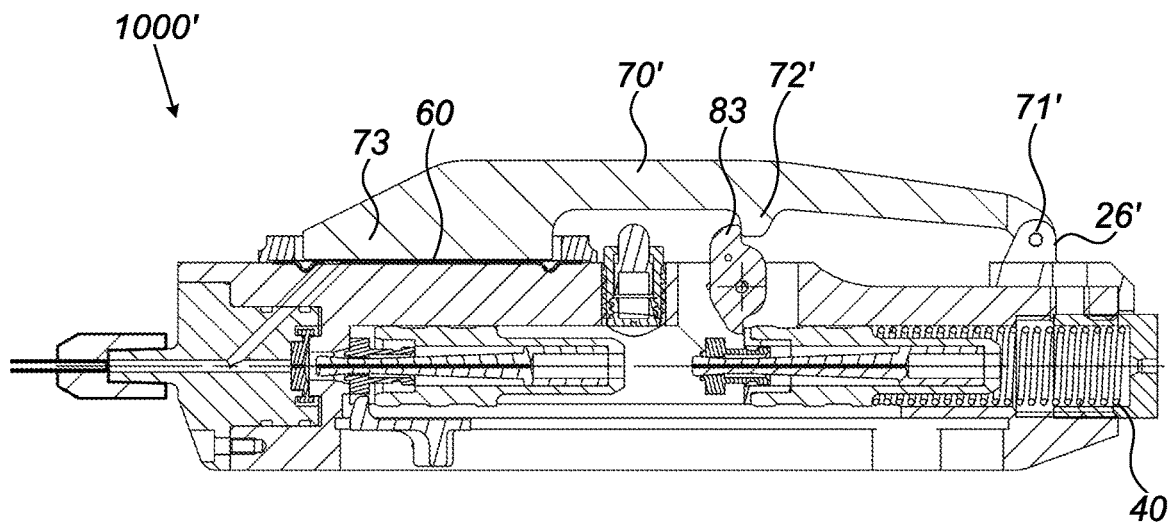
FIG. 2E is a longitudinal cross section of a mechanical cannulation device in accordance with yet another alternate embodiment of the invention.
Figure 2F:
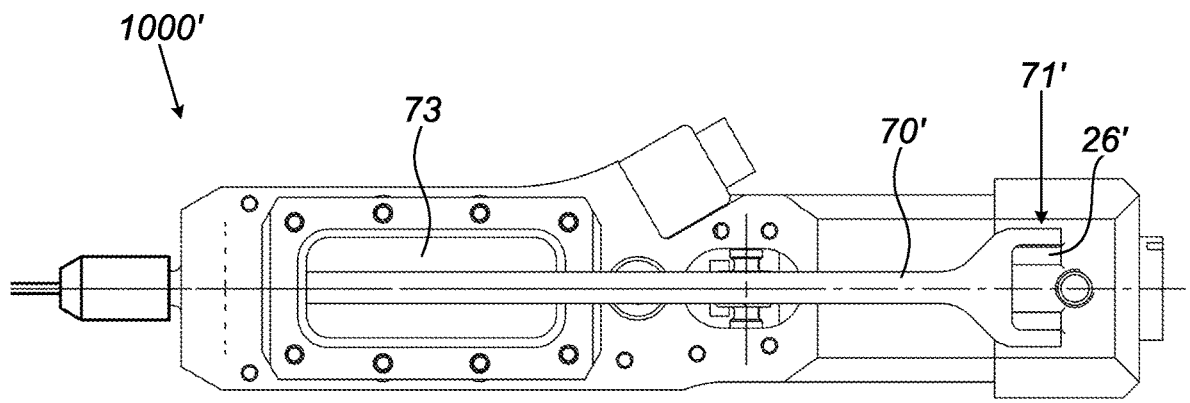
FIG. 2F is a top view of the device in FIG. 2E in accordance with an alternate embodiment of the invention.

In another embodiment shown in FIGS. 2E and 2F, the direction of the lever is reversed, so that the membrane force has a significantly greater torque than does the friction force between the lever and sear teeth, leading to a more predictable activation pattern.

More particularly, FIG. 2E is a longitudinal cross section of device 1000', which is identical in most details to device 1000 as shown in FIG. 1A, with the following differences: lever 70' has hinge 71' which runs through protrusion 26', located at the rear (proximal) part of device 1000', so that lever tooth 72' is between hinge 71' and lever base 73.

FIG. 2F is a top view of device 1000', showing the same elements.

In this embodiment, the force exerted by membrane 60 on lever base 73 has a longer arm from hinge 71' than does the friction force between lever tooth 72' and sear tooth 83, whereas in the embodiment shown in FIG. 1, the situation is the opposite. Therefore, in the current embodiment, the moment of force created by membrane 60 for lifting lever 70' is much larger than that of the opposing friction forces at lever tooth 72'. In other words, in this embodiment the membrane 60 is given an advantage over friction forces.

In this embodiment, changes in friction force between the lever and sear teeth have a minor effect on the force required for release of the trigger mechanism, and consequently on threshold pressure. Such changes in friction force may occur often due to various reasons such as variations in ambient temperature or humidity, in material properties, or in the forces applied by spring 40 and the spiral spring on sear 80. Thus, the current embodiment provides means for increasing the accuracy of deployment threshold.

This embodiment differs from previous embodiments in that because the hinge 71' is located further away from membrane 60 than hinge 71, even if the distance to which lever tooth 72' must move to activate the trigger mechanism is the same as lever tooth 72' in device 1000, the volume of fluid that must enter membrane 60 in order to produce this movement could be slightly larger, and might cause a different trigger response time.

The design can be modified by shortening the length of overlap between lever tooth 72' and sear tooth 83. This would decrease the required distance of movement and consequently the volume of fluid that must enter the membrane.

In an embodiment, the distance between the center of membrane 60 (or lever base 73) to hinge 71' is approximately double the distance between lever tooth 72' to hinge 71'. The ratio between these distances may be 1.2 to 4, preferably 1.5 to 3.

Electronic Vessel Cannulation Device

In another embodiment of the present invention, a vessel cannulation device utilizing electronic sensing and triggering is provided.

Figure 3A:
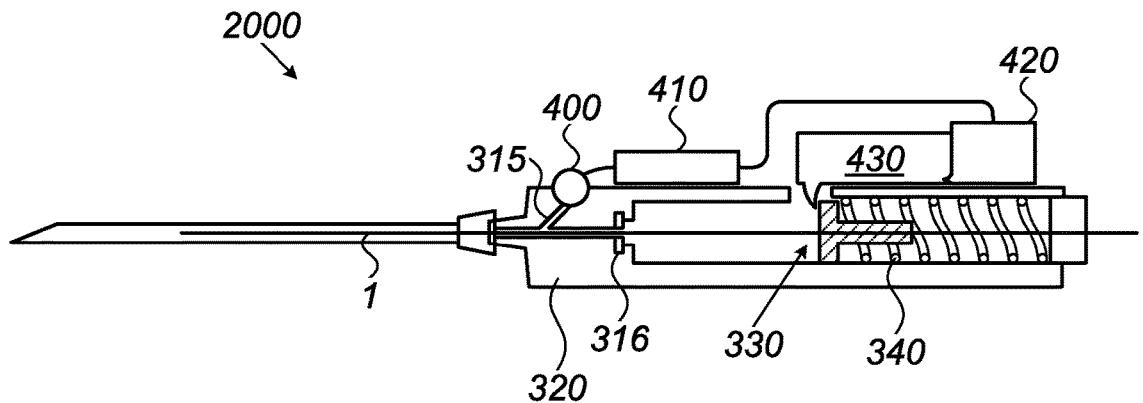
FIG. 3A is a schematic longitudinal section of an electronic vessel cannulation device in accordance with embodiments of the invention.

FIG. 3A is a schematic longitudinal section of electronic vessel cannulation device 2000 that can include or be utilized in conjunction with a processor, such as a computer. The structure of this device is generally similar to the mechanical device described above. Body 320 contains large spring 340, which pushes advancement mechanism 330 distally to advance guidewire 1, passing through valve 316 and needle. Fluid passageway 315 may lead from the lumen of the needle adapter to an electronic sensor 400, which may be a pressure sensor. The sensor may transmit its output to a CPU 410 which controls solenoid 420 (or other type of actuator), which is operably connected to trigger mechanism 430.

Figure 3B:
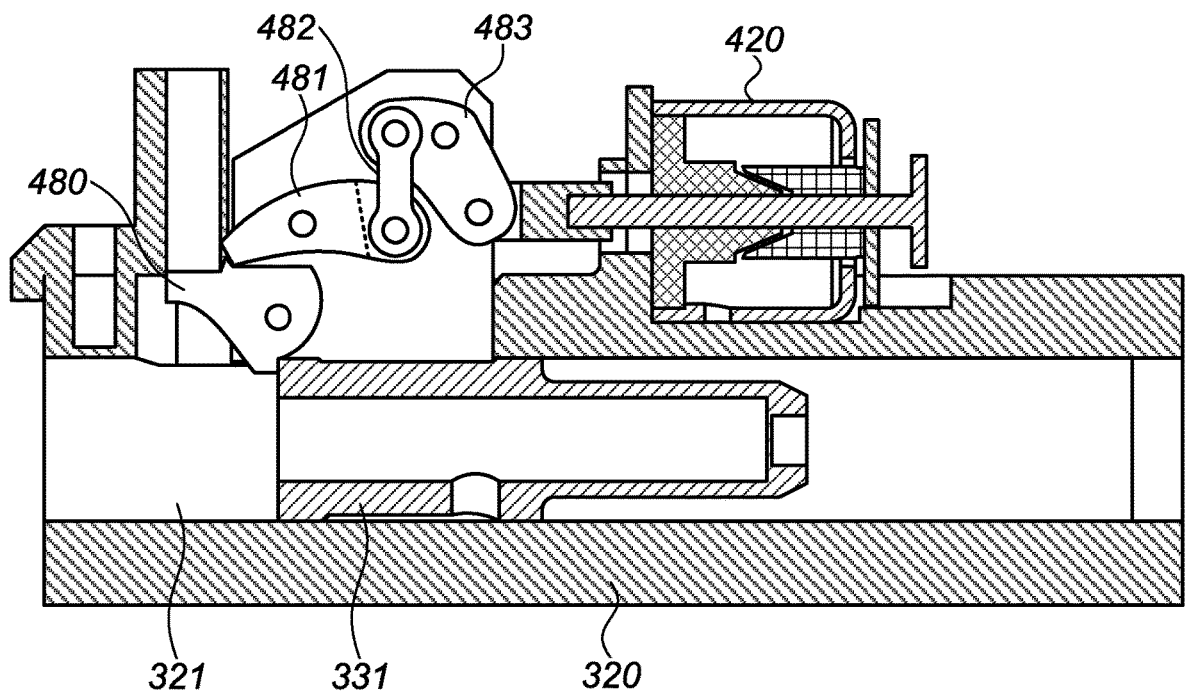
FIG. 3B is a schematic longitudinal section of a trigger mechanism in accordance with embodiments of the invention.

FIG. 3B is a schematic longitudinal section of an exemplary trigger mechanism 430 of device 2000. Slider 331 is seen within slot 321. Solenoid 420 is located outside the slot, and is connected such that it can pull lever 483 which may move levers 482, 481, and sear 480. Sear 480 has a tooth protruding into slot 321, which may engage with slider 331 in its cocked position, preventing its forward movement. Sear 480 and the levers are structured such that all the force of large spring 340 may transfer to the hinge of lever 481 without any torque around it, and therefore very little force is required to be exerted by solenoid 420 to release this trigger.

When device 2000 is used to puncture a vessel, sensor 400 may measure pressure or any other physiological parameter of blood or other fluid or gas at the needle tip or entering the needle. CPU 410 may be configured to execute computer-readable instructions to cause the device to analyze data sent by sensor 400. As further detailed below, device 2000 may be configured to be pre-set to identify parameters unique to arteries, veins, or other body cavities or organs, for example a specific pressure threshold or range. If predetermined criteria are met, CPU 410, when executed, may be configured to activate solenoid 420, which pulls lever 483, which eventually leads to clockwise rotation of sear 480, and release of slider 331, with advancement of advancement mechanism 330 and guidewire 1 or other blunting element.

Figure 4:
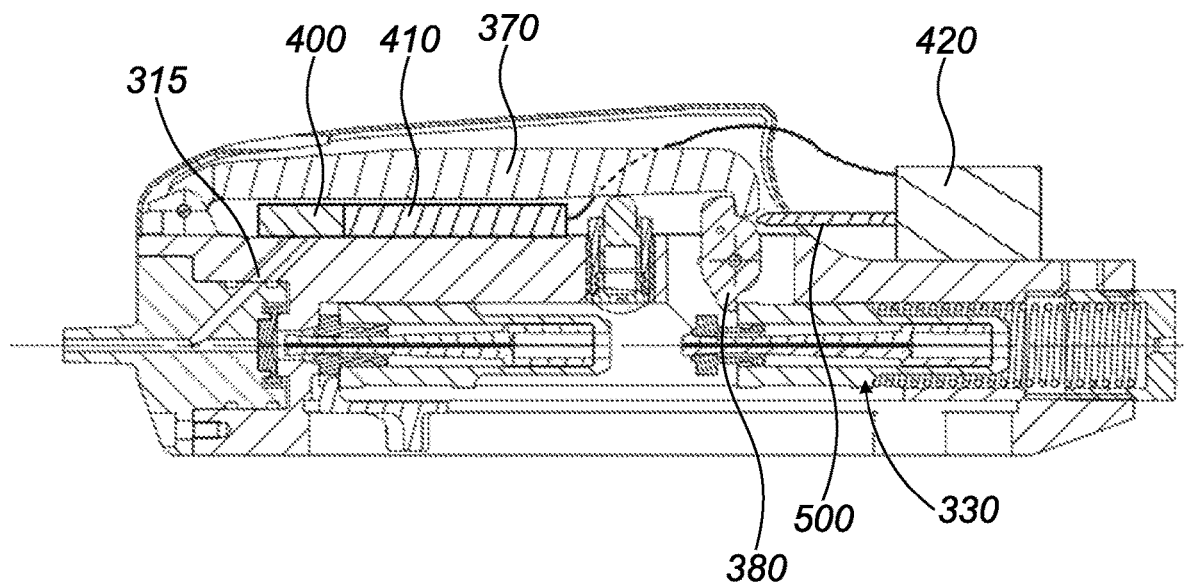
FIG. 4 is a schematic longitudinal section of an electronic vessel cannulation device in accordance with embodiments of the invention.

In another embodiment shown in FIG. 4, the same trigger mechanism described above for the mechanical cannulation device may be used, while sensing and activation of the trigger mechanism are electronic.

FIG. 4 is a longitudinal section of device 2000 similar in structure to the one shown in FIG. 1A. In some embodiments, membrane 60 and frame 65 may be replaced with sensor 400, which is connected to proximal fluid passageways 315. Sensor 400 may also be connected to CPU 410, which may also be connected to solenoid 420.

In the current embodiment, solenoid 420 is connected to a rod 500 with a wedge shaped tip, which is positioned at the meeting point of sear 380 and lever 370.

In operation, when fluid enters fluid passageways 315, CPU 410 activates solenoid 420, and rod 500 is pushed distally (i.e. left in this figure), and disengages lever 370 from sear 380, causing sear 380 to turn clockwise and releases advancement mechanism 330.

Electronic Advancement Mechanisms

In the above embodiments, advancement of the blunting element may be done mechanically. However, in some embodiments this may be achieved by electronic means. For example, a linear motor, large solenoid, or any other electronically activated device capable of linear motion could be used to advance advancement mechanism 330. Alternatively, rotary motors could roll the wire or advancement mechanism forward.

Sensor

Sensors used in the embodiments of the invention may be pressure sensors, temperature sensors, conductivity sensors, flow sensors, ultrasound sensors, pH sensors, optical sensors, or any other sensors as known in the art.

In some embodiments, at least a pressure sensor may be used. Sampling rate and communication speed between the sensor and CPU are of utmost importance, as a low sampling rate, or delayed communications might lead to delayed device responses, which could cause deployment outside of the vessel or other malfunctions.

As the relevant time scale of pressure changes in this application are several milliseconds, a sampling rate of 10 KSPS (Kilo samples per second) may be sufficient for most embodiments described herein, while for embodiments requiring more advanced signal analysis, a higher sampling rate is preferred.

The delay between the time of sampling to receipt of data by the CPU should be kept to a minimum, as response time to the pressure change should be short to avoid deployment outside of the vessel or other malfunctions.

A differential pressure sensor is preferred, as only the relative pressure between the internal pressure of the vessel and the ambient pressure is relevant to the measurement. A +/−400 mbar (300 mmHG) differential pressure measurement is sufficient, as the pressure inside the vessel will always be within this range.

A suitable sensor for this application may for example be the Honeywell Amplified Basic Pressure sensor #X210907, with a differential pressure +/−400 mbar (300 mmHG) and 0.42 ms response time.

The sensor may be located as close to the target tissue as possible, that is, at the needle tip if possible, at the needle hub, or on the device as close as possible to the needle hub. Placing the sensor on the device has the advantage of using standard needles, thus reducing disposable costs.

In some embodiments, a combination of several sensors may be used. This may enable using a combination of physiological parameters at the needle tip to more accurately identify a specific body cavity, and initiate action.

Flow Chart

Figure 5A:
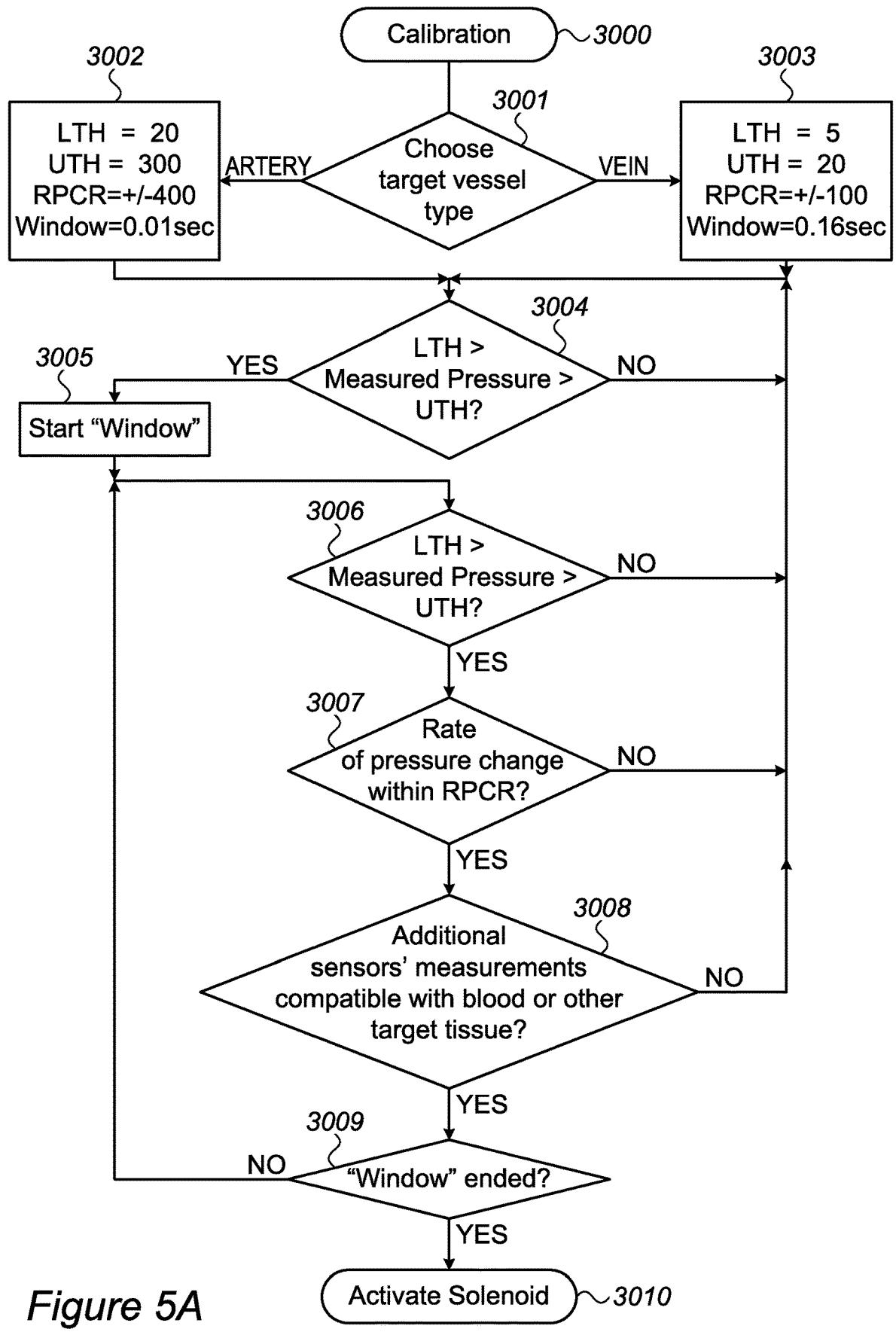
FIG. 5A is an exemplary flowchart that may be implemented using the devices of the invention in accordance with certain embodiments of the invention.

FIG. 5A is a flow chart of a process which may be implemented by the device of embodiments of the invention.

Step 3000:

The process may begin with calibration of the sensor to ambient pressure and temperature, which is performed prior to skin puncture. This is not always necessary, and depends on the specifications of the sensor used.

Step 3001:

The user may then optionally select whether the target vessel is an artery or a vein. This can be performed by any input device for example using a simple button on the device, or any input device described below. Optionally, the device has a user interface allowing choice of the target vessel type, and optionally input of additional information such as patient personal or clinical data. Alternatively, in some embodiments each device is either arterial or venous, i.e. it is preset to suit a specific vessel type.

Steps 3002 and 3003:

Selection of the vessel type defines parameters analyzed by the device. These may include a pressure range, for which a Lower Threshold (LTH), and an Upper Threshold (UTH) are defined. Additional parameters may for example include a Range of Pressure Change Rate (RPCR).

Settings for an artery may be:
LTH 20 mmHg
UTH 300 mmHg
RPCR +/−400 mmHg/sec
Window 0.01 sec
Settings for a vein may be:
LTH 5 mmHg
UTH 20 mmHg
RPCR +/−100 mmHg/sec
Window 0.16 sec These ranges are given as an example mainly used in trauma scenarios, and may be defined differently. Ranges may also be defined according to the patient's clinical condition. For example, in a patient with right heart failure, the range of central venous pressures may be higher and overlap with arterial pressures. In such a case the range for a venous cannulation may for example be 5-40 mmHg, and additional measures such as rate of pressure change and possibly other physiological parameters may need to be taken into account.

Optionally a user will input the patient's characteristics including age, gender, habitus, clinical situation, and possibly the purpose of intervention, and the device may suggest an appropriate pressure range, or may choose the pressure range automatically.

Step 3004:

The CPU may be configured to process a received pressure measurement from the sensor, an average of measurements, or several measurements and in some embodiments may perform a running average, or other calculation to remove noise from the data. The CPU may be configured to compare the current pressure value to the predefined range. If not within that range, the CPU may be configured to repeat this step 3004 until a vessel with this pressure range is penetrated, which allows moving to the next step.

Step 3005:

A timer, such as a clock, may be used to start measuring time from penetration of the vessel. This time measurement may serve as a time window during which the solenoid is not activated, and measurements continue, in order to confirm that the right type of vessel was penetrated. This is mainly because when an artery is punctured, pressure in the sensor transitions between ambient to the arterial pressure, passing through the venous pressure range.

For example, if a pressure reading of 8 mmHg was received, this may be from a vein, but could also just be a transitional pressure while the sensor goes from ~0 mmHg to say ~100 mmHg. If an artery was penetrated, sensor pressure may equilibrate with the arterial pressure very soon, so that if pressure remains in the venous range after the time window has ended, this serves as an indication that a vein was punctured.

In some embodiments, ranges for the time window for a vein may be 0.05-0.3 seconds, preferably 0.08-0.2 seconds. In some embodiments, ranges for the time window for an artery may be shorter, e.g., 0-0.2 seconds, 0-0.1 seconds, or 0-0.05 seconds.

Step 3006:

The CPU may be configured to inquire the same question as in step 3004. If the pressure value is outside the range, this means the needle has exited the vessel, and the process may return to step 3004.

If the pressure value is within the range, this means the needle is probably still in the vessel, and the process may continue to step 3007.

Step 3007:

The CPU may be configured to analyze the pressure change rate between successive measurements and/or over a certain time period.

The range of pressure change rate mentioned in step 3002 for a vein (+/−100 mmHg) may vary with system design, and may be between +/−50 mmHg/sec to +/−150 mmHg/sec, preferably between +/−80 mmHg/sec to +/−120 mmHg/sec.

The range of pressure change rate mentioned in step 3002 for an artery (+/−400 mmHg) may vary with system design, and may be between +/−350 mmHg/sec to +/−450 mmHg/sec, preferably between +/−380 mmHg/sec to +/−420 mmHg/sec.

These ranges may also vary with clinical condition, and may optionally be calibrated according to pulse rate, arterial pressure, patient characteristics, and clinical status.

If the current pressure change rate is outside the predefined range, this probably means that despite the current pressure reading being within the predefined pressure range, the needle has either exited the vessel, or entered the wrong vessel type (artery instead of vein) and the process may return to step 3004.

If the current pressure change rate is within the predefined range, this means the needle is probably still in the vessel, and the process may continue to step 3008.

Step 3008:

Optionally, the CPU may configure to compare various additional physiologic parameter values, measured by sensors as previously mentioned, to predefined ranges. If these parameters are found to be outside the predefined ranges (in some embodiments, these would be compatible with intravascular conditions), the process may return to step 3004. If within range, the process may continue to step 3009.

This step may optionally consist of multiple such stages, using multiple inputs, for example verifying intravascular conditions by measuring impedance, pH, temperature, reflectance, and any other parameter enabling distinguishing between blood and extravascular tissues, or identifying any other target tissue or fluid.

In some embodiments only if all parameters are within predetermined ranges, will the process continue to step 3009. Alternatively in other embodiments, each parameter may receive a "grade" (e.g. 10 for within range, and decreasing as distance from range increases), and an average or other function of these grades serves as the basis for the process's decision making. In yet other embodiments, each parameter may be further assigned a weight according to its accuracy, signal to noise ratio, or importance, and a weighted average may be calculated.

Such use of multiple physiologic parameters, or multiple inputs, for verifying correct vessel penetration, may increase sensitivity and specificity of the device.

Step 3009:

The CPU may be configured to check whether the time window has expired. If it has, this means that all measured parameters remained within their predefined ranges for a sufficient period of time, which in very high likelihood means that the needle has penetrated, and is still in the lumen of the correct type of vessel.

If the time window has not yet expired, the process may return to step 3006, and may continue monitoring the parameters as described above.

If the time window has expired, or in other words if the time falls outside a predetermined time window, the process may continue to step 3010 to activate the solenoid.

In some embodiments, the pressure versus time graph curve contour may be analyzed to determine whether a needle is in the correct cavity. Parameters of the pressure curve that may be analyzed, may include for example the complete shape of the pressure-time graph, degree and rate of pressure change since assumed penetration into the vessel, the pressure change gradient, area under the pressure curve, etc.

In some embodiments, the pressure curve may be monitored for a very short period and it can be predicted how the curve should look before and after the monitoring period. Further, the shape of the measured pressure curve can be compared to the predicted shape, thus identifying pressure changes that are a result of entering/exiting a vessel, and not natural pressure changes within the vessel.

In some embodiments, simultaneous ECG monitoring, which may be performed through the needle, or through external electrodes, is correlated with the pressure curve, to identify "real" pressure changes within a vessel vs those resulting from entering/exiting a vessel.

In an embodiment, a bank of measurements may be used from past patients, to compare with the measured pressure curve.

In an embodiment, rapid measurements at the very start of an initial pressure rise may be used, to extrapolate whether the final pressure would reach a venous or an arterial level. Because this is done extremely rapidly, preferably within less than 50 milliseconds, the assumption is that in this case the needle would not have time to exit the vessel before the solenoid is activated and the blunting device is deployed.

In an embodiment, all or any combination of the above methods may be used, or shifts between them according to various stages of the procedure.

Figure 5B:
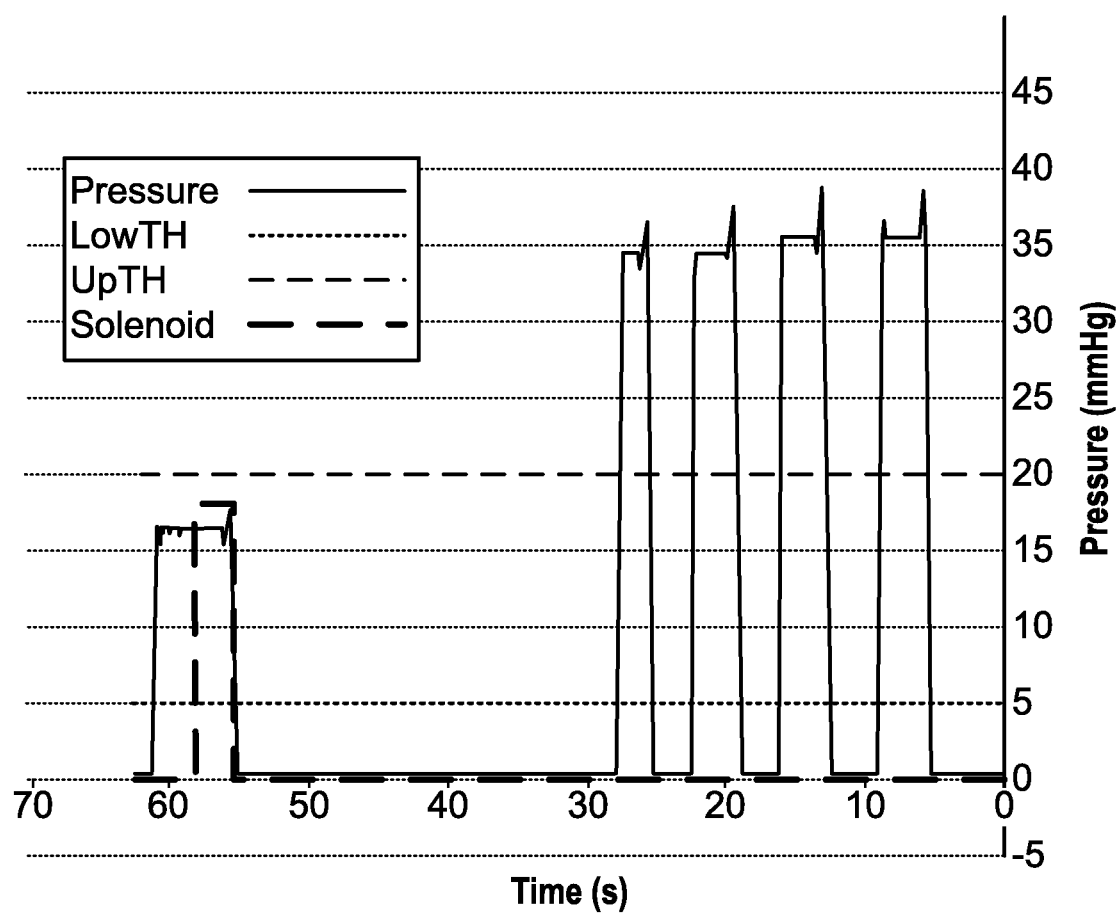
FIG. 5B is a graph produced using a device in accordance with embodiments of the invention.

FIG. 5B is a graph produced using a prototype device similar in structure to the one described in FIG. 4, and the process similar to that described in FIG. 5A. Pressure measurements from the device's sensor were constantly recorded on a laptop computer. In the graph, pressure (Y axis, mmHg) is plotted against time (X axis, seconds), from right to left. LTH and UTH are plotted as straight lines, and solenoid activity is plotted as well, with a value of 0 representing its "OFF" state, and 18 representing its "ON" state.

In this experiment, the device was used to puncture silicone tubes containing water in known pressure. LTH was set to 5 mmHg, UTH to 20 mmHg. The time window was set to 100 milliseconds, and the duration of solenoid activation was set to 3 seconds.

During the first four punctures, at times ~5 sec, ~13 sec, 19 sec, and 25 sec, the pressure was ~36 mmHg, simulating arterial pressure in a hypotensive patient. During the fifth puncture, at time ~56 sec, the pressure was ~17 mmHg, simulating venous pressure. Nothing was changed in the device between the punctures.

As seen in the graph, the solenoid was not activated in any of the first four punctures into the "artery" tube, despite the measured pressure briefly passing within the predetermined venous range, both while increasing, and while decreasing. However, in the fifth puncture, this time into the "vein" tube, the solenoid was activated immediately upon end of the time window, because the measured pressure remained within the LTH-UTH range.

Figure 5C:
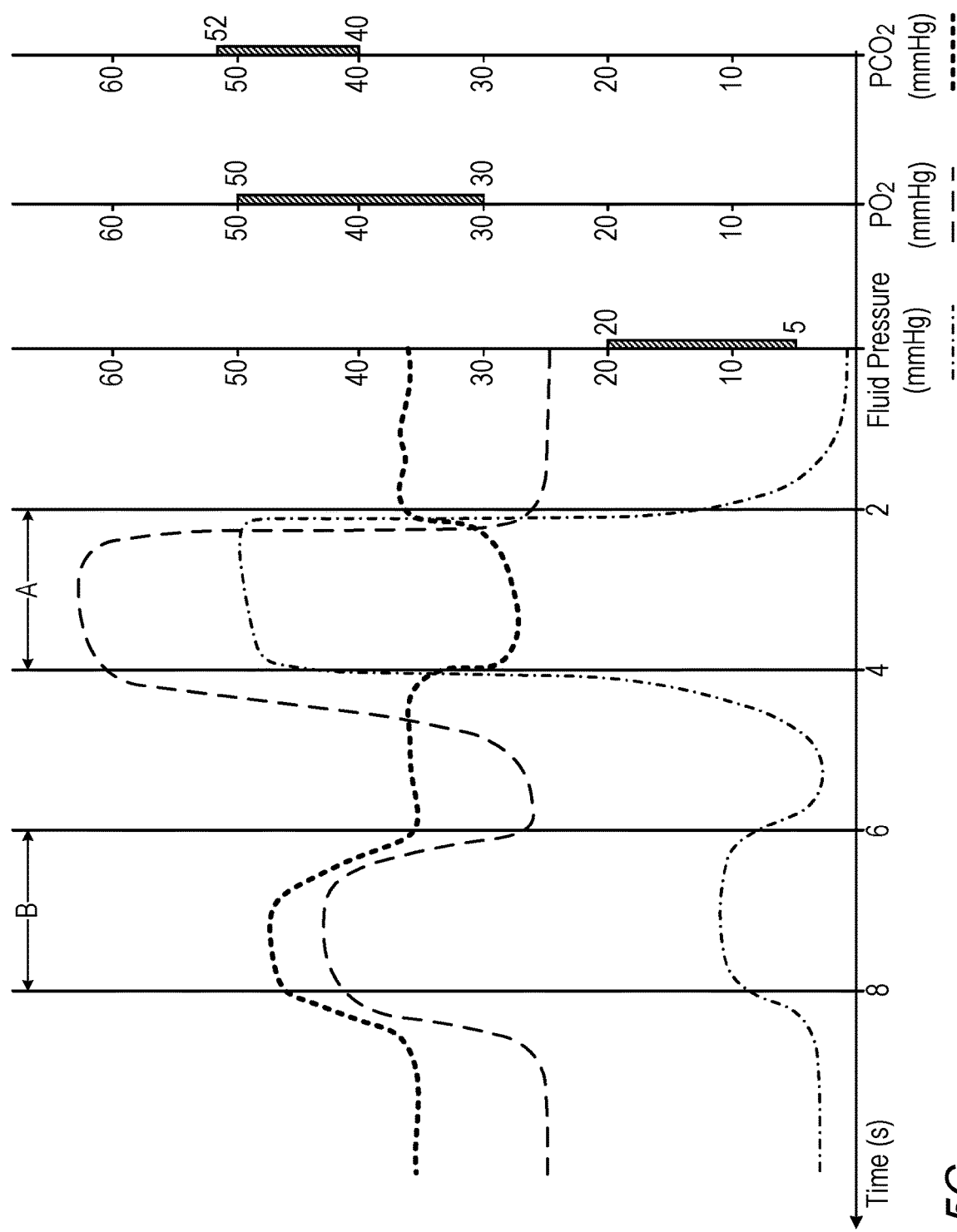
FIG. 5C is a theoretical graph depicting possible multiple physiologic parameter measurement values during puncture through a patient's tissues and blood vessels, which may be used in accordance with embodiments of the invention.

FIG. 5C is a theoretical graph depicting the concept of using multiple physiological parameters as inputs for the process described in FIG. 5A, and specifically in step 3008, in order to provide an example of how the system may function.

More particularly, FIG. 5C is a graph showing possible real time measurements of fluid pressure, PO2 (oxygen tension), and PCO2 (Carbon Dioxide tension) at the tip of a needle during puncture of body tissue and blood vessels. The horizontal axis represents time, and the vertical axis represents the values of the measured parameters (fluid pressure, PO2, PCO2). Additional or other physiological parameters not shown in this graph may be used, including but not limited to pH, temperature, flow, glucose content, optical reflectance, etc.

Scales on the right side of the graph show possible typical ranges of each parameter for venous blood. These may be 5-20 mmHg for fluid pressure, 30-50 mmHg for PO2, 40-54 mmHg for PCO2. These venous ranges are marked by wide bars, to the right of each of the scales. Typical arterial ranges for these parameters may be approximately above 20 mmHg for fluid pressure, 75-10 mmHg for PO2, 25 to 45 mmHg for PCO2.

In the graph, the continuous line represents fluid pressure, the dashed line represents PO2, and the dotted line represents PCO2. Depicted are two events, A and B, in which parameters change significantly due to puncture of a body lumen or vessel.

Event A represents possible measurements during arterial puncture: fluid pressure may rapidly rise to well above 20 mmHg, PO2 may rise from a level of ~25 mmHg in muscle or other tissue to 75-100 mmHg, and PCO2 may decrease from 30-40 mmHg up to 25 mmHg. Altogether, these values, especially when compared to the values measured in tissue before the rapid change at the time of vessel puncture, indicate that the punctured vessel may be an artery. If the chosen vessel type was a vein, the system's CPU may analyze these data and refrain from deploying the blunting element in this vessel. Comparing the values measured during event A to the venous ranges (wide bars to the right of the scales) shows that all parameters are outside the venous ranges. Following exit of the needle tip from the vessel, values return to their levels in surrounding tissue.

Event B represents possible measurements during venous puncture: fluid pressure may (less rapidly than before) rise to well 5-20 mmHg, PO2 may rise from a level of ~25 mmHg in muscle or other tissue to 30-50 mmHg (significantly less than arterial), and PCO2 may rise from 30-40 mmHg 40-52 mmHg. Altogether, these values, especially when compared to the values measured in tissue before the rapid change at the time of vessel puncture, indicate that the punctured vessel may be a vein. If the chosen vessel type was a vein, the system's CPU may analyze these data, recognize the parameters are within the venous ranges (compare values to the wide bars at the right of each scale), and deploy the blunting element in this vessel. Otherwise, following exit of the needle tip from the vessel, values return to their levels in surrounding tissue.

Figure 5D:
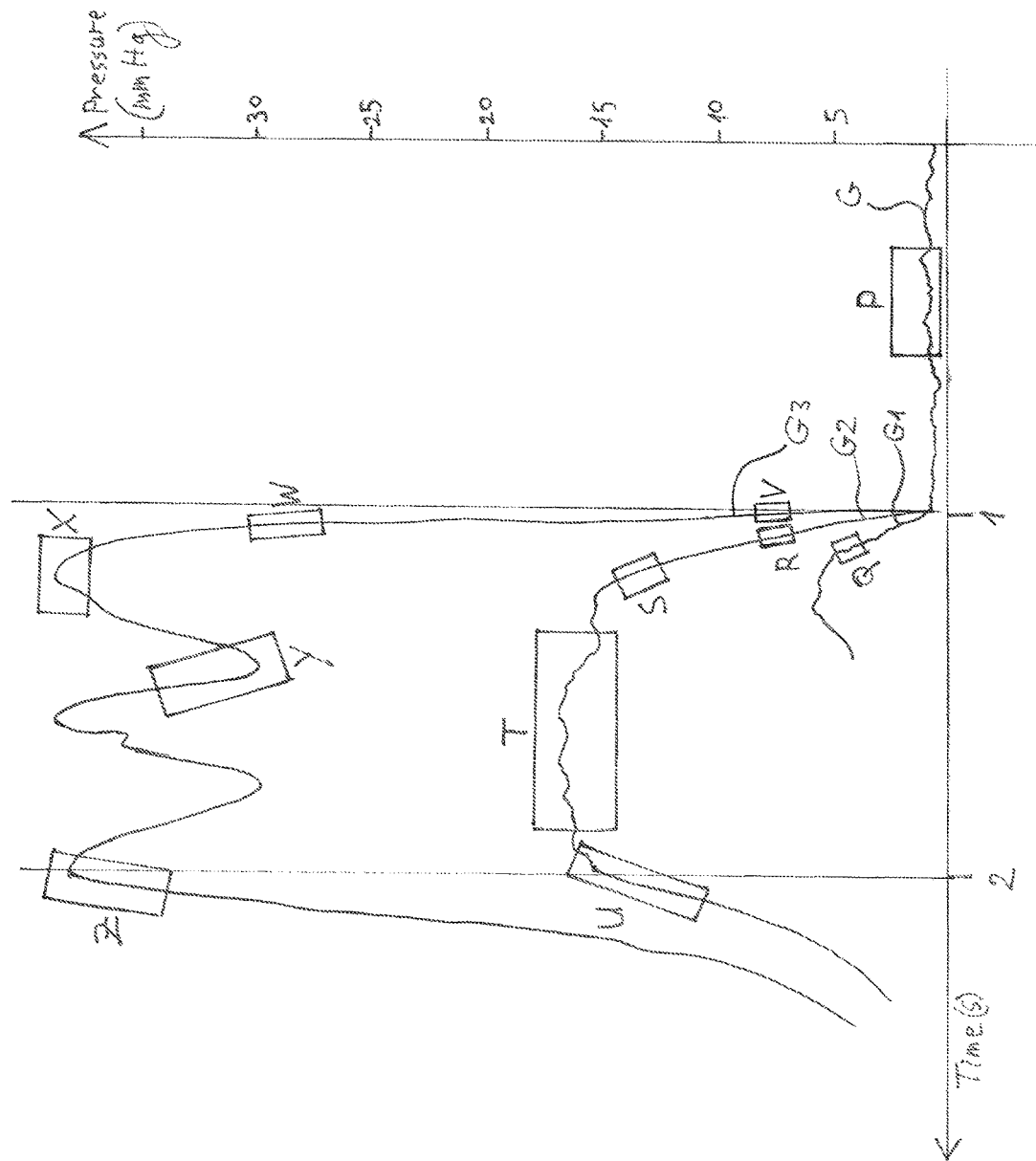
FIG. 5D is a simplified theoretical graph depicting various possible pressure measurement contours.

FIG. 5D is a simplified theoretical graph depicting various possible pressure measurement contours, for describing examples of pressure curves which may be measured at the needle tip of a device 2000, and their contour analysis as may be performed by the process described in FIG. 5B. The described curves and analyses are examples, and are not meant to cover all possible uses of the data within the scope of the current disclosure.

More particularly, FIG. 5D is a simplified, schematic, theoretical graph of fluid pressure (in mmHg) at the needle tip, plotted against time (in seconds). During the first second of measurement, a graph G is shown, depicting pressure which may be measured in tissues such as skin or subcutaneous tissue, before puncture of a blood vessel. A segment of the pressure curve marked P is shown.

At time 1 second, a theoretical puncture into a vessel occurs. Three possible graphs are shown from this point: G1—"artifact"—including segment Q, G2—"venous puncture"—including segments R, S, T, U, and G3—"arterial puncture"—including segments V, W, X, Y, Z. Of course only one such graph may be measured by one device at its needle tip at a single time, however the three are brought herein together in order to exemplify various possible pressure contours.

Segment P shows pressure slightly fluctuating around 1 mmHg. This may be typical of measurements within body tissue that is not under pressure, i.e. for example skin or subcutaneous tissue, fat, and muscles of the limbs, without external pressure or edema. Typically pressure in these tissues may be close to zero, however slight fluctuations as shown in segment P may be common and may result from "noise" caused by movements of the patient or device, changes in device position and height, electromagnetic interference etc. Various methods of analysis as known in the art may be used to minimize this "noise" including running averages etc.

At second 1 there is an abrupt change in the pressure curve. G1 is an example of such change, which may be caused not by puncture of a vessel, but for example by extreme movement of the patient. Such an artifact may be recognized when analyzing the graph, for example by identifying the rate of change, which may not be as abrupt, and the contour may not be as smooth, as in the case of true vessel puncture. Typically, such a change may be short standing, and may not reach high pressure levels.

G2 and G3 are graphs describing typical pressure measurements upon puncture of a vein or an artery, respectively. When puncturing a vein, pressure would typically rise abruptly, however not as abruptly as in the case of arterial puncture, so the rate of change, as seen by the slope of the graph in segment R (venous), is lower than that in segment V (arterial). Typically this rate of change in pressure may be sufficient to distinguish between venous and arterial puncture, as described in the process of FIG. 5B. Pressure buildup within the needle, fluid passageways, and sensor may take time, typically several tens of milliseconds, depending on the vessel pressure, and therefore the pressure graph rises along that period of time. Arterial pressure may typically be sufficient to reach measured pressure levels above the upper threshold for veins (which may typically be chosen as above 20 mmHg), within 100-200 milliseconds from the time of puncture. After that time, if pressure is still within the venous range, the punctured vessel may be identified as venous. This is exemplified by segment T which may be a typical pressure measurement in a central vein, around 15-16 mmHg. This pressure may be relatively high for most patients, however the important point is the fluctuations in pressure shown in segment T. Such fluctuations are typical of venous pressure, and may be caused by reasons as described previously for segment P, and in addition, by the patient's respiratory activity, and/or cardiac activity. Such fluctuations typically have a known rhythm, and can therefore be identified, and may typically not be mistaken for changes in the position of the needle (i.e. will typically not be assumed to be caused by the needle exiting the vessel or entering an artery).

Even before the pressure graph reaches the venous "stable state" (segment T), segment S shows a significant decrease in the rate of pressure rise, which can be identified by the process of FIG. 5B, especially when compared to segment R, and considering the time lapse between the two segments. In other words, a decrease in the slope of the curve within a short time, and without a significant rise in absolute pressure, enables predicting the final pressure level, by extrapolation.

In contrast, segment W in graph G3 (arterial) still shows a very steep slope, i.e. pressure continues to rise quickly. The maximal pressure shown in this sample graph as seen in segment X, is very low for an arterial pressure (~40 mmHg), but may be consistent with a patient in shock, which is an indication for use of the devices of the current disclosure. Of note, segment X includes the peak arterial pressure and may show an abrupt fall in pressure after the peak, which is typical of an arterial pressure contour. There are various other known features of the arterial pressure graph, depending on where the pressure is measured, such as the dicrotic notch. However the important point for the current embodiment is that such abrupt changes as shown in segments X and Y of G3 wherein the slope changes from very positive to very negative or the opposite, are typical of arterial pressure and enable distinguishing between vessel types. Importantly, these typical contours may enable identifying the vessel type within a very short time, e.g. within less than 100 ms, which may advantageously occur before passing of several heart beats of the patient, and before the respective pulsatile blood pressure contour is recorded. That is to say, waiting the required time until pulsatile pressure can be identified, may be too long for optimal function of the cannulation device, and therefore rapid identification (within 50-200 ms) of the vessel type by a short segment of the contour is beneficial.

At second 2, a theoretical measurement of pressure at a time of exit of the needle tip from the vessel lumen is depicted. Both G2 and G3 show an abrupt fall in measured pressure as seen in segments U and Z respectively. However, due to the large difference in pressure between the lumen and surrounding in the arterial case, and the smaller difference in the venous case, the slope of pressure decrease is much steeper for the artery as seen in segment Z versus the vein as seen in segment U. This steeper slope may enable the system to distinguish between exit of the needle tip from an artery as opposed to the typical pressure fall during diastole (as seen for example at the end of segment X).

Some or all of the above may be used within the software for analysis of the pressure curve contour for identifying the location of a needle tip—in tissue, in an artery, or in a vein. Similar considerations and calculations may be applied to multiple other physiologic parameters which may be measured by embodiments of the current disclosure.

Reusable and Disposable Combinations

Various embodiments of reusable and disposable combinations of the electronic device are described below. These are generally similar to those described for the mechanical device in FIGS. 2A-2D. Of note, in each of the following electronic sensor embodiments, the sensor may either be disposable or reusable. If the sensor is reusable, there may be a separation between it and biological fluid, that on the one hand allows pressure transmission, and on the other hand prevents sensor contamination by patients' body fluids. Such a separation may for example consist of a gel plug, a thin polymeric membrane, or other appropriate partition.

In an embodiment, the solenoid and trigger mechanism are reusable and the rest (body, large spring, slider, seal, and passageways) are disposable. As mentioned above, the sensor may be either disposable or reusable (analogous to FIG. 2A).

In another embodiment, in a device that advances only an external sheath (no guidewire), where there is no seal and possibility of blood entry into mechanism. Therefore, only the needle, the adapter and/or the sensor are disposable (analogous to FIG. 2B).

In another embodiment, the guidewire may be coaxial with the large spring, but the inner part of the advancement mechanism may be replaceable. Therefore, only the guidewire, the gripper, the needle adapter, the needle, and/or the sensor may be disposable (analogous to FIG. 2C).

In yet another embodiment, the guidewire is not coaxial with the large spring. Therefore, only the guidewire, the gripper, the needle adapter, the needle, and/or the sensor may be disposable (analogous to FIG. 2D).

Blunting Elements

In some embodiments of the present invention, the cannulation devices of the present invention may include blunting elements, which may comprise one or more guidewires, or other elements advanced through the needle and/or a sheath advanced over the needle. In some embodiments, the blunting element may be operable to cover the tip of a needle. In some embodiment, the blunting element may be positioned close to the needle tip prior to vessel puncturing, such that the blunting element may be quickly deployed into the vessel to cover the needle tip and prevent injuries to the vessel wall.

An advantage of using a sheath over the needle as the blunting element of the cannulation device, is that a non-hollow needle can be used. Such a non-hollow needle may have a relatively small diameter. In addition, a needle that has a sensor at its tip may be used (usually this will be a non-hollow needle, or hollow but with a small inner diameter). The sensor may be a pressure sensor or a different type of sensor (flow, impedance, etc.). The sensor may be in electronic communication with the vessel cannulation device and operable to transmit pressure information to the processor for automatic deployment of the blunting element.

FIGS. 6-11 show various "blunting" elements in accordance with embodiments of the invention.

Figure 6A:
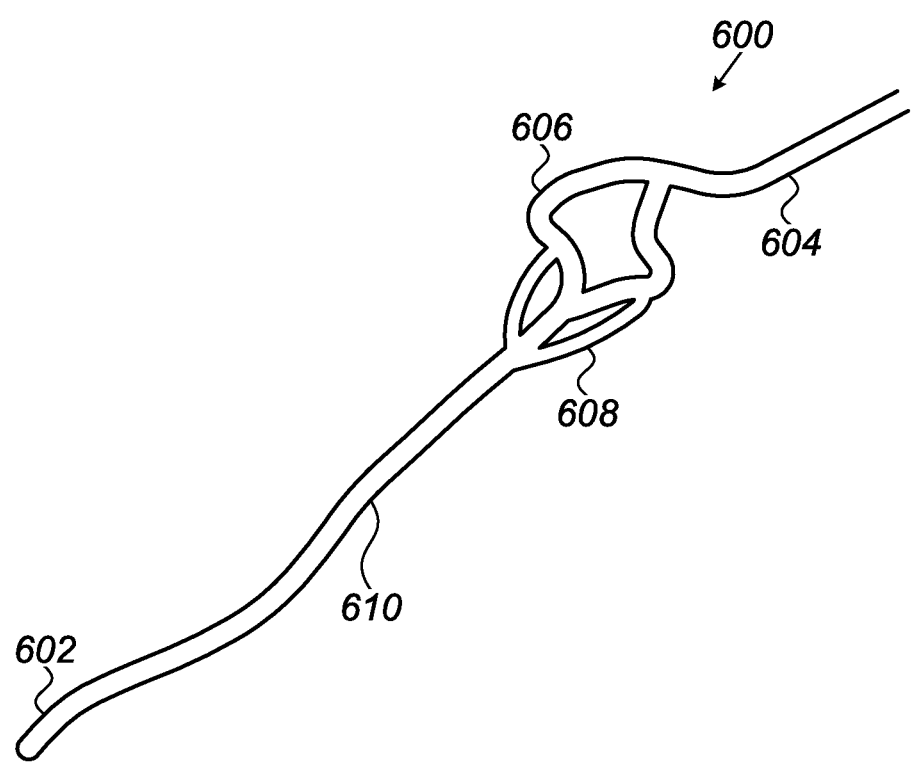
FIGS. 6A-6D show a stent like "tip covering" blunting element in accordance with an embodiment of the invention.

FIGS. 6A-6D depict an embodiment of a stent like "tip covering" internal blunting element 600. More particularly, FIG. 6A is a 3D depiction of blunting element 600 having proximal part 604 which may be a guidewire or similar to a guidewire, diverging area 606 which may be an area configured to project forward and outward, then inward, downward, and backward, converging area 608, which may be configured to project forward and inwards, distal area 610, gradually becoming softer, and distal tip 602.

Figure 6B:
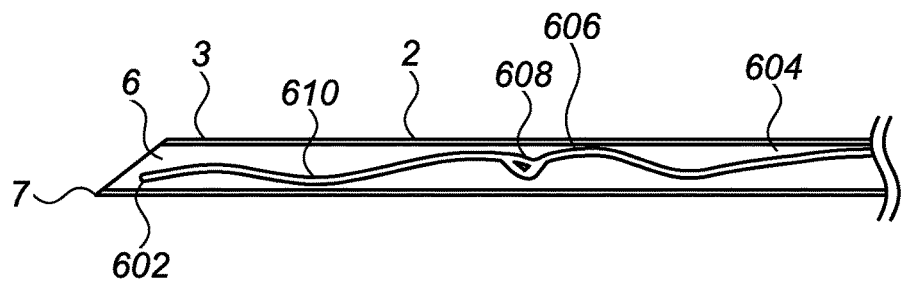

FIG. 6B is a longitudinal section of blunting element 600 in its crimped state, inside lumen 6 of needle 2. Needle 2 has distal end 3, lumen 6, and bevel point 7. Blunting element 600 is seen slideably positioned within lumen 6 of needle 2, with its distal tip 602 positioned near distal end 3 of needle 2, not protruding out of lumen 6. Of note, areas 606 and 608 of blunting element 600 are flexible and therefore assume a relatively straightened configuration within lumen 6.

Figure 6C:
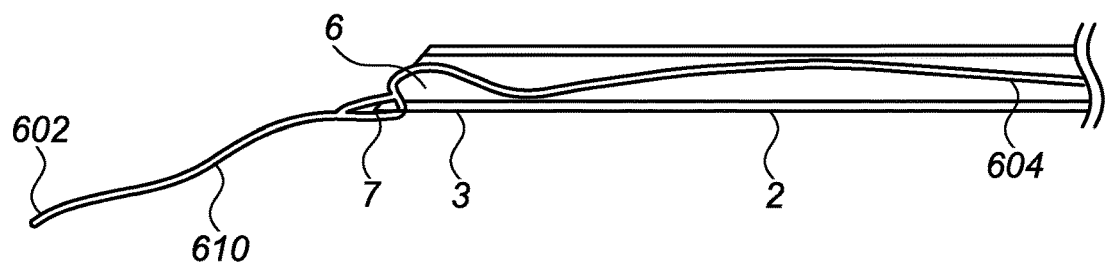

FIG. 6C is a longitudinal section of blunting element 600 in its deployed state. Blunting element 600 is seen partially protruding out of lumen 6 of needle 2. Area 606 of blunting element 600 may extend forward and outward out of lumen 6, then backwards inwards and downwards along and around the outer surface of distal end 3 of needle 2, continued by areas 608 which extend forward and inward, converging into area 610, which may be a guidewire or similar.

Figure 6D:
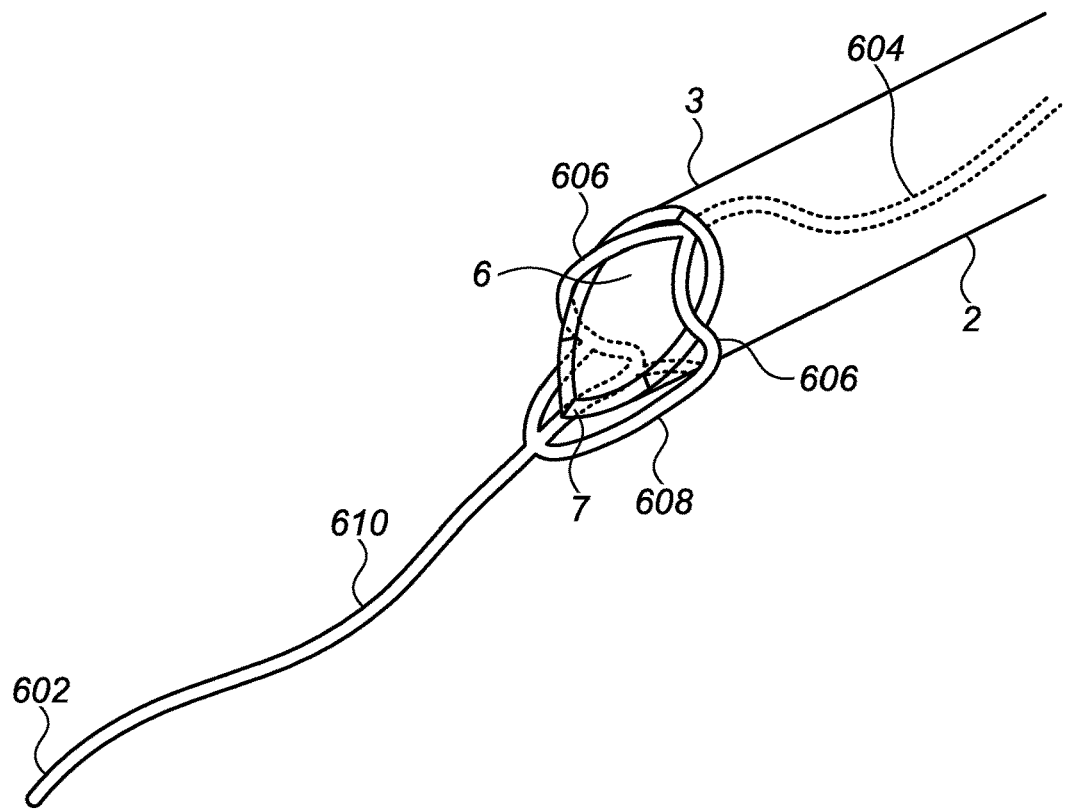

FIG. 6D is an isometric depiction of blunting element 600 in its deployed state, showing the same features as in FIG. 6C.

In operation, blunting element 600 may be advanced by any of the vessel cannulation devices of the invention, other cannulation devices, or manually, immediately following puncture of the target lumen. The blunting element 600 may be advanced to an exact position, such that areas 606 and 608 cover the inferior aspect of bevel point 7, thus preventing it from inadvertently puncturing through the vessel wall and exiting the vessel lumen.

In some embodiments, additional struts or wires connect any of proximal part 604 and diverging area 606 with converging area 608 and distal area 610, thus covering also the superior aspect of bevel point 7.

In an embodiment, blunting element 600 may be made of a cable or braid, and areas 606 and 608 consist of a segment of the cable, which may be unwound or uncoiled, and its strands diverge outwards. Other embodiments of blunting element 600 are possible. The blunting element 600 has an extendable segment (areas 606 and 608) configured to cover bevel point 7 in its deployed state, and which in its crimped state, does not substantially obstruct needle lumen 6.

In an embodiment, vessel cannulation device 1000 or 2000 may advance blunting element 600 or any of the following blunting elements (to be described below) to a specific position, then may pull it slightly backwards (proximally), to make sure areas 606 and 608 cover bevel point 7.

Figure 7A:
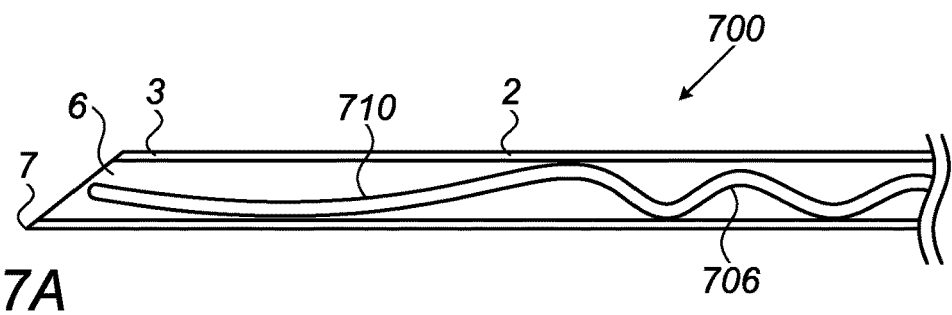
FIGS. 7A and 7B show a coiling "tip covering" blunting element in accordance with an embodiment of the invention.
Figure 7B:
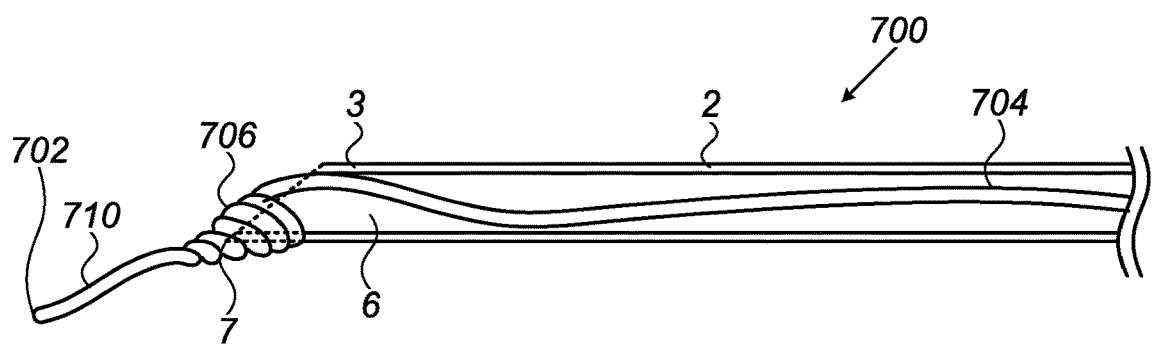

FIGS. 7A and 7B depict an embodiment of a coiling "tip covering" blunting element 700. More particularly, FIG. 7A shows a longitudinal section of blunting element 700 in its crimped state, inside lumen 6 of needle 2. Blunting element 700 is seen slideably positioned within lumen 6 of needle 2, with its distal tip 702 positioned near distal end 3 of needle 2, not protruding out of lumen 6. Area 706 of blunting element 700 may be flexible and therefore assume a relatively straightened configuration within lumen 6.

FIG. 7B shows a longitudinal section of blunting element 700 in its deployed state. Blunting element 700 is seen partially protruding out of lumen 6 of needle 2. Area 706 of blunting element 700 may extend out of lumen 6, coiling around distal end 3 of needle 2, thus covering bevel point 7, and continues as distal part 710, which is a soft relatively guidewire.

In some embodiments, blunting element 700 may be made of a guidewire, which has been pretreated by heat treatment, mechanical treatment, or other method, to confer a coiling tendency to area 706.

FIGS. 8A-8E depict an embodiment of a "tip completing" blunting element 800, shaped as a longitudinally cut tube segment with a shape that fits with and complements the needle bevel into a blunt end.

Figure 8A:
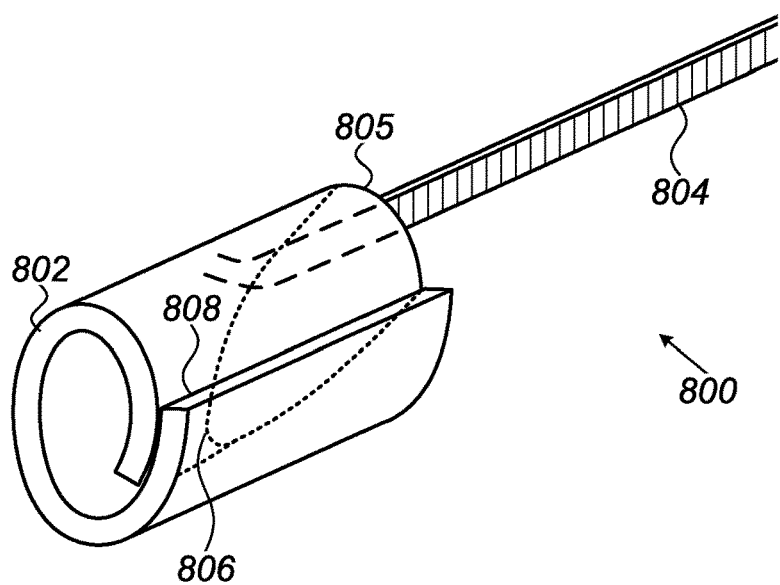
FIGS. 8A-8E show a "tip completing" blunting element in accordance with an embodiment of the invention.

More particularly, FIG. 8A shows a 3D depiction of blunting element 800 showing distal tip 802, slit 808, inferior fit 806, superior fit 805, and proximal part 804, which may be a guidewire or strip or other long element, extending proximally from the proximal end of the slit tube, and enabling pushing blunting element 800 distally.

Figure 8B:
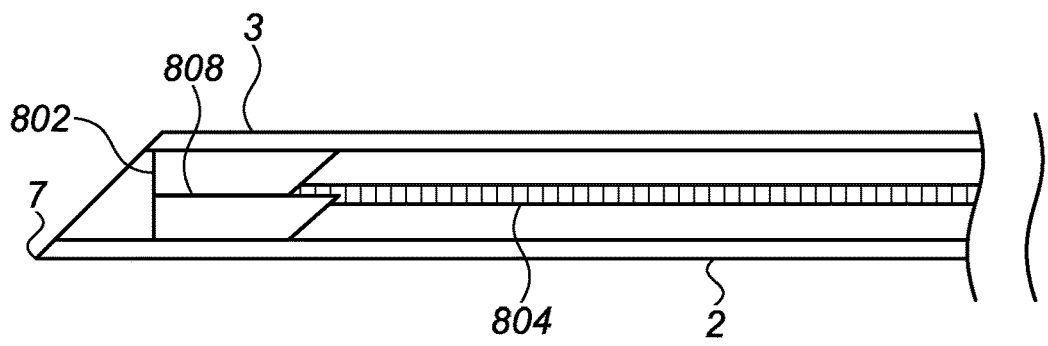

FIG. 8B shows a longitudinal section of blunting element 800 in its crimped state, inside lumen 6 of needle 2. Blunting element 800 is seen slideably positioned within lumen 6 of needle 2, with its distal tip 802 positioned near distal end 3 of needle 2, not protruding out of lumen 6. The blunting element 800, which is longitudinally slit at slit 808, may coil upon itself such that its ends overlap to some extent, reducing its outer diameter sufficiently for it to be inserted into lumen 6 of needle 2.

Figure 8C:
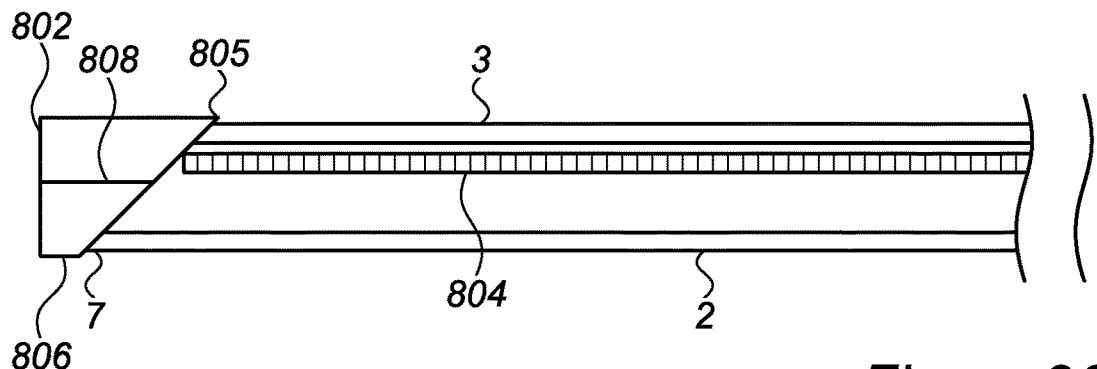

FIG. 8C shows a longitudinal section of blunting element 800 in its deployed state. Blunting element 800 is seen partially protruding out of lumen 6 of needle 2. Once pushed out of lumen 6 by any of a cannulation device or manually, blunting element 800 may pop out to its original outer diameter, which may be identical or close to that of needle 2. Bevel point 7 may be positioned within inferior fit 806, and superior fit 805 sits at the upper end of the needle bevel. In this position, blunting element 800 has a distal end 802 which may be round and blunt, while superior fit 805 and inferior fit 806 prevent it from being pushed back proximally. Thus, a blunt needle end may be created.

Figure 8D:
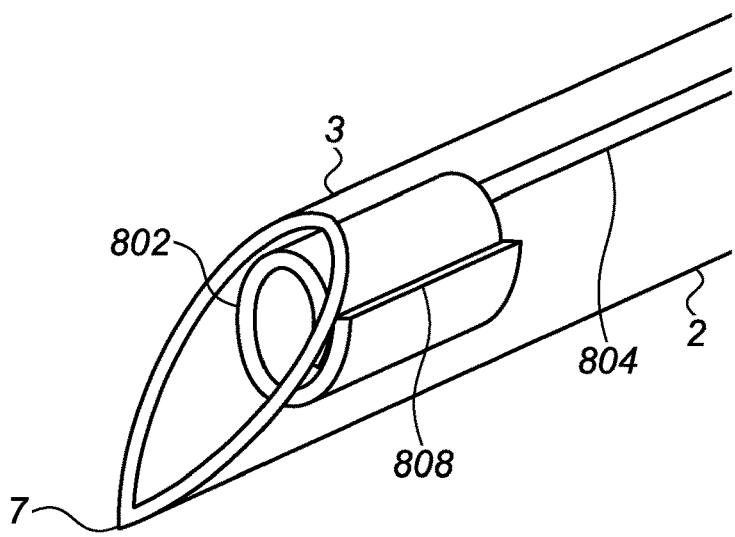
Figure 8E:
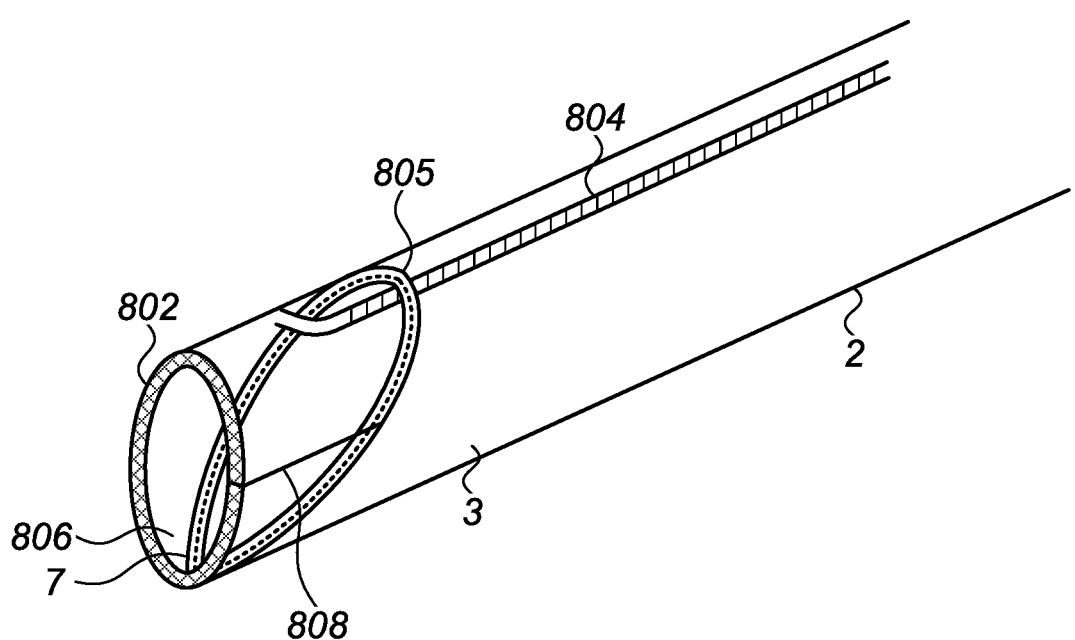

FIGS. 8D and 8E are 3D drawings showing the same as FIGS. 8B and 8C.

FIGS. 9A-9D depict an embodiment of a "internal sheath" blunting element 900, in some embodiments, comprising a thin tube with a blunt, atraumatic tip.

Figure 9A:
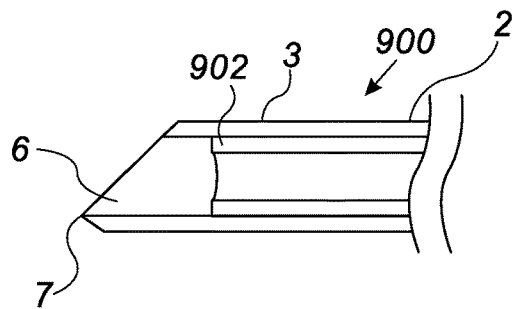
FIGS. 9A-9D show an "internal sheath" blunting element in accordance with an embodiment of the invention.

More particularly, FIG. 9A shows a longitudinal section of blunting element 900 in its crimped state, inside lumen 6 of needle 2. Blunting element 900 is seen slideably positioned within lumen 6 of needle 2, with its distal tip 902 positioned near distal end 3 of needle 2, not protruding out of lumen 6. Although in this drawing blunting element 900 is depicted as a short sheath, it may be a longer sheath with a more rigid proximal part to be positioned at the needle tip when deployed, and a softer distal tip. The change between these areas may be gradual, but may also be in steps. Note also that in this embodiment, bevel point 7 of needle 2 may be preferably shaped such that it is at the inner side of the needle wall, to ensure a smooth taper from blunting element 900.

Figure 9B:
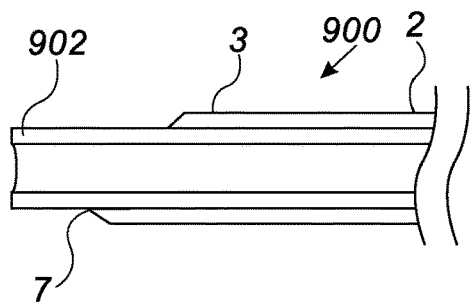

FIG. 9B shows a longitudinal section of blunting element 900 in its deployed state. Blunting element 900 is seen partially protruding out of lumen 6 of needle 2. Once pushed out of lumen 6 by any of a cannulation device or manually, blunting element 900 may extend beyond needle distal end 3, and provides a blunt end at distal tip 902 with a smooth taper to needle 2.

Figure 9C:
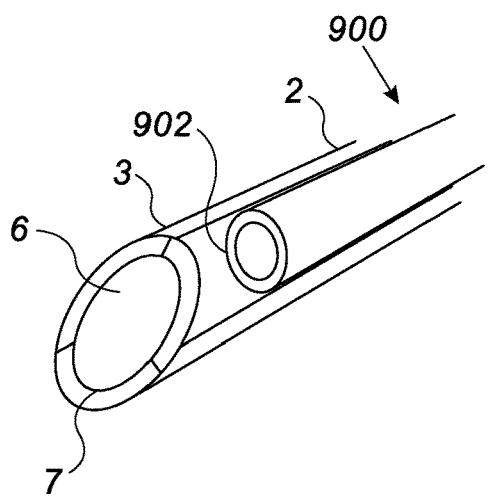
Figure 9D:
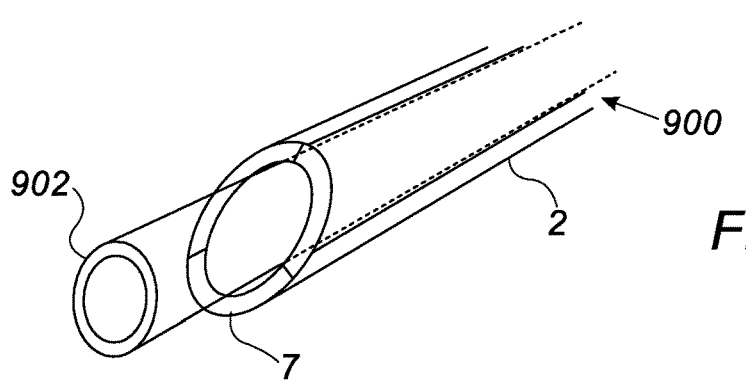

FIGS. 9C and 9D are 3D drawings showing the same as FIGS. 9A and 9B.

FIGS. 10A-10D depict another embodiment of an "internal sheath" blunting element 1100, which is different from the previous one in that it covers the needle bevel point.

Figure 10A:
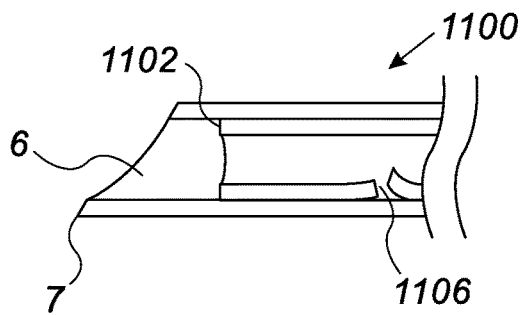
FIGS. 10A-10D show an "internal sheath" blunting element in accordance with an embodiment of the invention.

More particularly, FIG. 10A shows a longitudinal section of blunting element 1100 in its crimped state, inside lumen 6 of needle 2. Blunting element 1100 may be seen slideably positioned within lumen 6 of needle 2, with its distal tip 1102 positioned near distal end 3 of needle 2, not protruding out of lumen 6. Opening 1106 may be a cross slit in the sheath of blunting element 1100. The sheath may be preshaped with a curve towards the side of the bevel point 7, but the sheath may be straightened within the needle lumen in this figure.

Figure 10B:
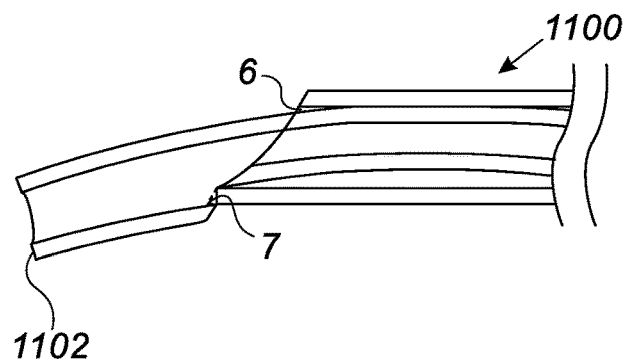

FIG. 10B shows a longitudinal section of blunting element 1100 in its deployed state. Blunting element 1100 is seen partially protruding out of lumen 6 of needle 2. Once pushed out of lumen 6 by any of a cannulation device or manually, blunting element 900 may extend beyond needle distal end 3, and provides a blunt end at distal tip 1102 within the vessel lumen. Additionally, the blunting element 900 may curve towards bevel point 7, and is may be pulled slightly backwards such that bevel point 7 enters into opening 1006, thus rendering the needle tip blunt.

Figure 10C:
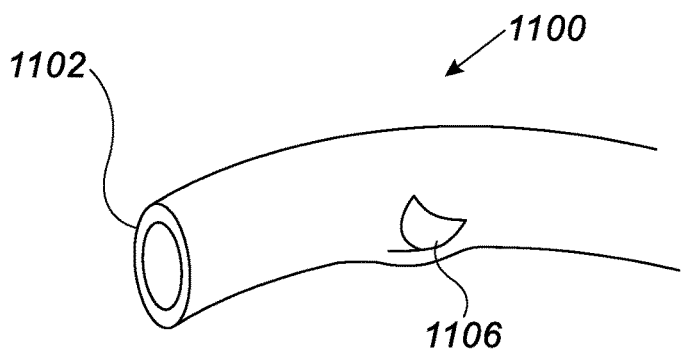

FIG. 10C shows a 3D drawing of deployed blunting element 1100 without the needle.

Figure 10D:
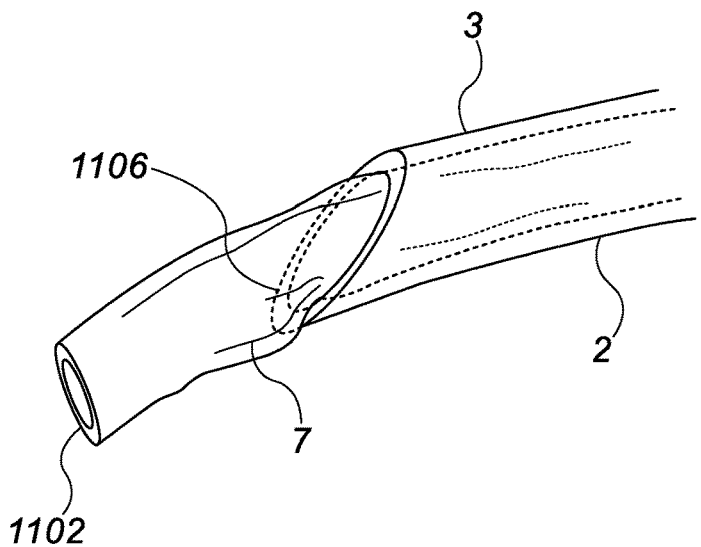

FIG. 10D shows a 3D drawing of deployed blunting element 1100 with the needle.

FIGS. 11A-11D depict an embodiment of a "sandwich sheath" blunting element 1200, may comprise two layers of over-the-needle sheaths.

Figure 11A:
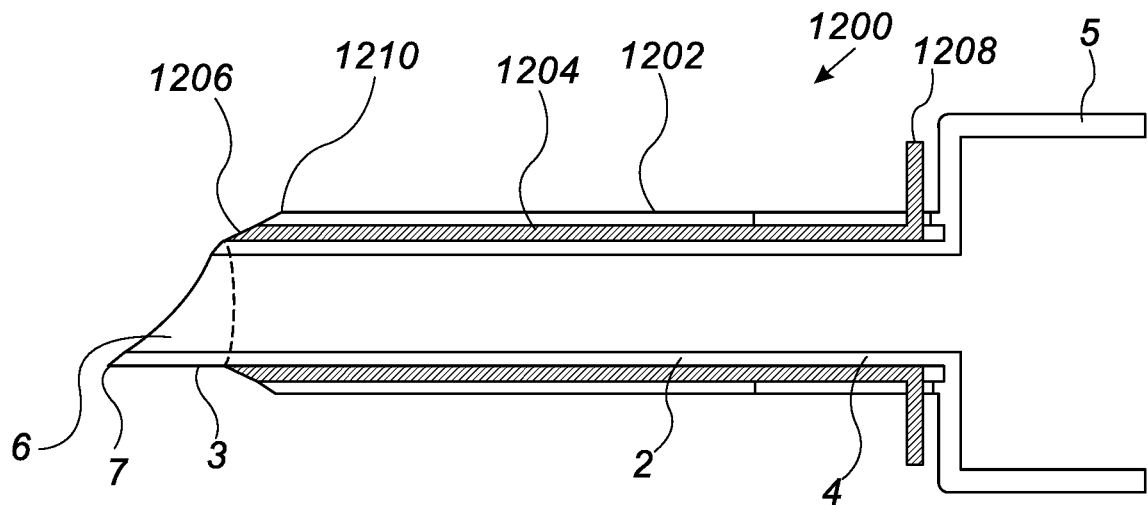
FIGS. 11A and 11B show a "sandwich sheath" blunting element in accordance with an embodiment of the invention.

More particularly, FIG. 11A shows a longitudinal section of blunting element 1200 in its crimped state, positioned over needle 2. Blunting element 1200 may comprise outer sheath 1202 and inner sheath 1204. Inner sheath 1204 may have inner sheath distal tip 1206 and inner sheath protrusions 1208. Outer sheath 1202 may have distal tip 1210. The proximal end of outer sheath 1202 may be connected to needle hub 5, and may have slots through which protrude protrusions 1208. Inner sheath 1204 may be slideably positioned between needle 2 and outer sheath 1202. The distal tips 1206 and 1210 of both inner sheath 1204 and outer sheath 1202 may be proximate to each other and together create a taper towards distal end 3 of needle 2.

Figure 11B:
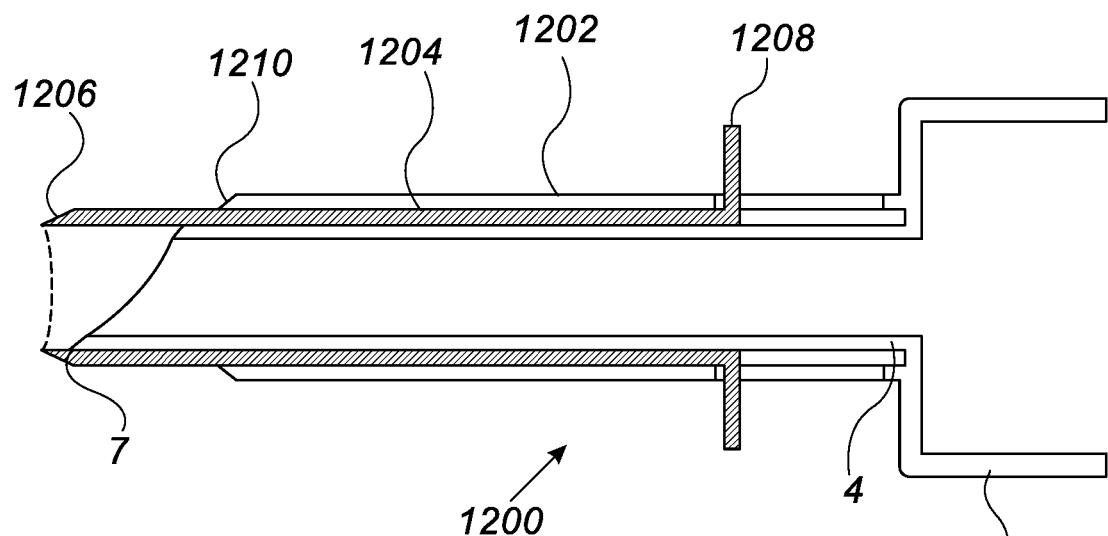

FIG. 11B shows a longitudinal section of blunting element 1200 in its deployed state. Inner sheath 1204 is seen partially protruding beyond distal end 3 of needle 2, providing a blunt end covering bevel point 7 at distal end 3. Although in this drawing inner sheath 1204 is depicted as protruding a short distance, it may protrude to a large distance, in some embodiments, with a more rigid proximal part to be positioned at the needle tip when deployed, and a softer distal tip. The change between these areas may be gradual, but can be in steps.

In use, once the vessel is penetrated by needle 2, inner sheath protrusions 1208 may be pushed forward by a cannulation device or a user. Inner sheath 1204 slides over needle 2 and within outer sheath 1202 at least until it covers distal tip 3. An advantage of this embodiment is that inner sheath 1204 has almost no contact with tissue surrounding the needle, and so can be advanced without pushing the needle out of the vessel, as can commonly happen with sheaths over needles. At the same time it does not compromise the needle inner lumen.

Any of the blunting elements and cannulation devices described herein and in the incorporated applications may be used interchangeably with each other.

Guidance

Various embodiments for guiding the puncture procedure are described below. The descriptions will use device 1000 as example, but may relate to any of devices 2000 or others described above and elsewhere.

Mechanical Guidance

Figure 12A:
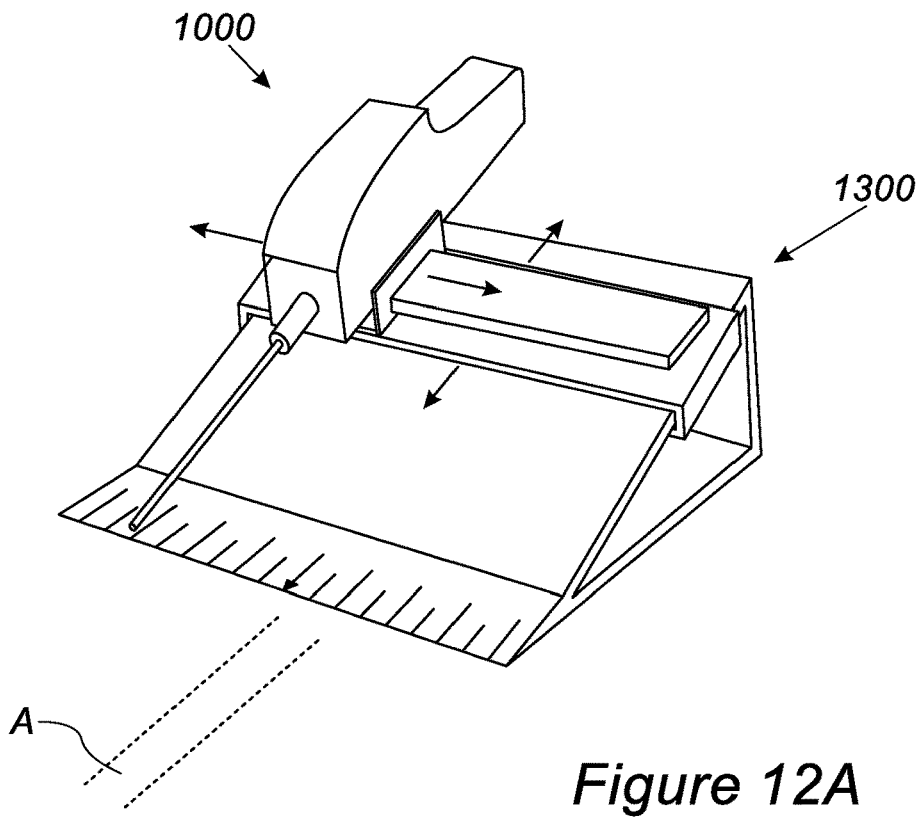
FIG. 12A shows a simple linear mechanical guide used for guiding the cannulation procedure in accordance with an embodiment of the invention.

In an embodiment shown in FIG. 12A, a simple linear mechanical guide 1300 may be used for guiding the cannulation procedure. Mechanical guide 1300 enables sliding any of the above described cannulation devices over a slope of approximately 30-45 degrees, directed at the target vessel (marked "A" in the figure), while remaining substantially parallel to the vessel's longitudinal axis. Optionally, mechanical guide 1300 may be foldable. Markings at its front edge may be used to indicate distance between punctures.

In use, mechanical guide 1300 may be placed on the patient's skin, with its central marking above the estimated location of the target vessel, and pointing in the direction of the vessel's longitudinal axis. The user may begin puncturing the skin at a location approximately 1-2 cm to one side of the center marking, and performs consecutive parallel punctures, each time approximately 2 mm closer to the central marking, and continues beyond it if necessary.

In this manner, all possible space where the target vessel can pass may be covered, and once the vessel is punctured by the needle, the cannulation device may be deployed.

Figure 12B:
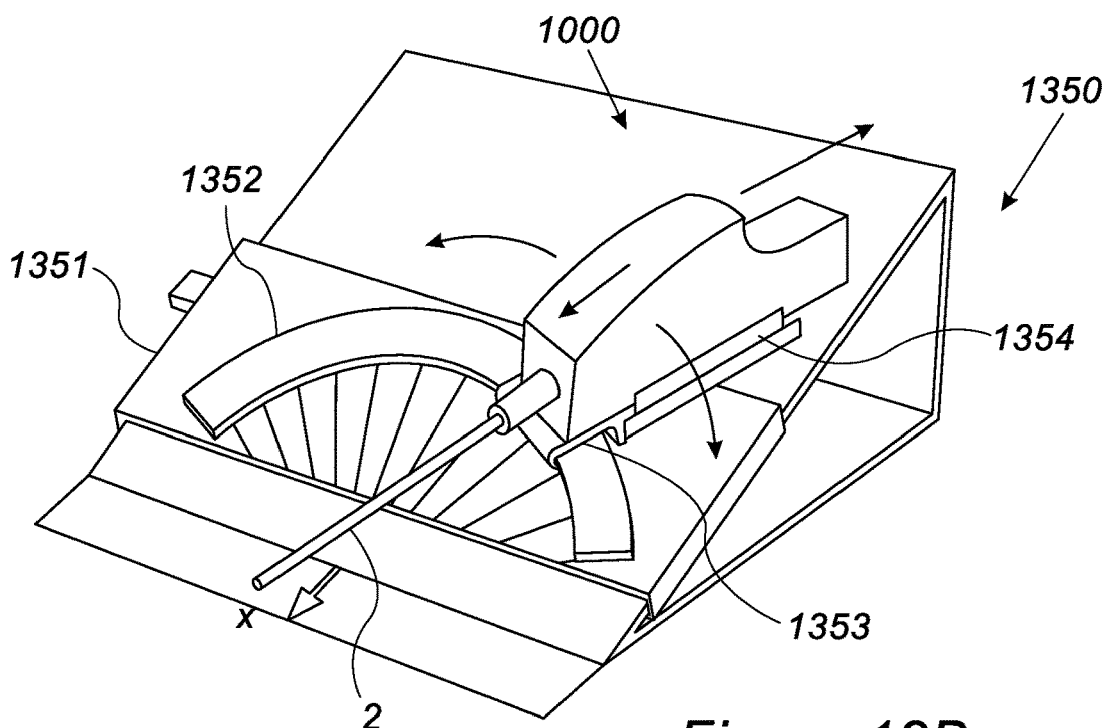
FIG. 12B shows a simple rotary mechanical guide used for guiding the cannulation procedure in accordance with an embodiment of the invention.

In an embodiment shown in FIG. 12B, a simple rotary mechanical guide 1350 is used for guiding the cannulation procedure. Mechanical guide 1350 may enable sliding any of the above described cannulation devices over a slope of approximately 30-45 degrees to the patient's skin, while rotating the needle tip at the same point, in some embodiments, 1-2 mm below the skin surface. Optionally, mechanical guide 1350 may be foldable. Optionally, a surface 1351 may slide up and down the slope and can be locked to it at any point. An arch 1352 may be attached to surface 1351, with its center located beyond the lower edge of surface 1351. Attachment 1353 may slide around arch 1352, while slab 1354 may slide back and forth over attachment 1353. Device 1000 may be attached to slab 1354 such that it can be moved around arch 1352 and back and forth with its needle 2 pointing to the center of arch 1352. Markings along arch 1352 may be used to indicate angles between punctures.

In use, mechanical rotary guide 1350 may be placed on the patient's skin, with its central marking above the estimated location of the target vessel, and pointing in the direction of the vessel's longitudinal axis. Optionally, the user may determine the height of surface 1351 such that the center of arch 1352 is at any depth below the patient's skin surface, in come embodiments, 1-2 mm below the skin. Alternatively, this height may be fixed. The user may begin puncturing the skin at an angle approximately 30-45 degrees to one side of the center marking, and perform consecutive punctures, each time going a few degrees closer to the central marking, and continues beyond it if necessary.

In this manner, most possible space where the target vessel can pass may be covered, and once the vessel is punctured by the needle, the cannulation device will deploy.

Optionally, stops may be placed that limit sliding of slab 1354, limiting the minimum and maximum needle insertion depths, so that the needle is not accidentally pulled out of the skin, and remains inside the skin.

Imaging Based Guidance

In some embodiments, imaging may be used as part of any of the previously described cannulation devices.

Figure 13A:
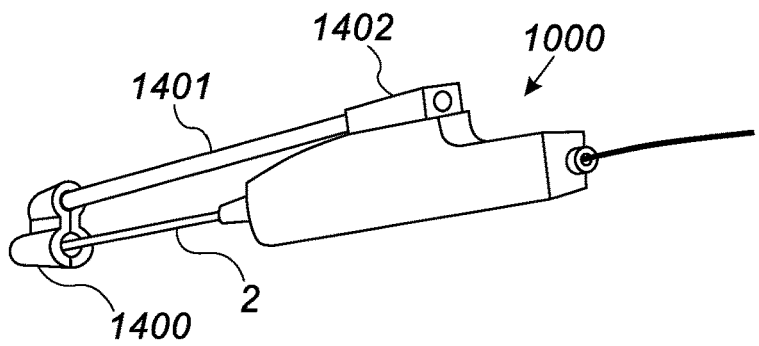
FIGS. 13A-13D show an ultrasonic transducer used as part of a cannulation device in embodiments of the invention.
Figure 13B:
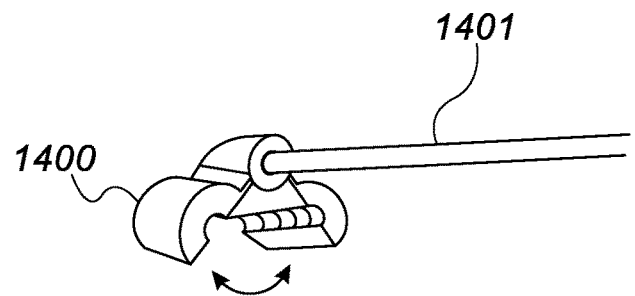
Figure 13C:
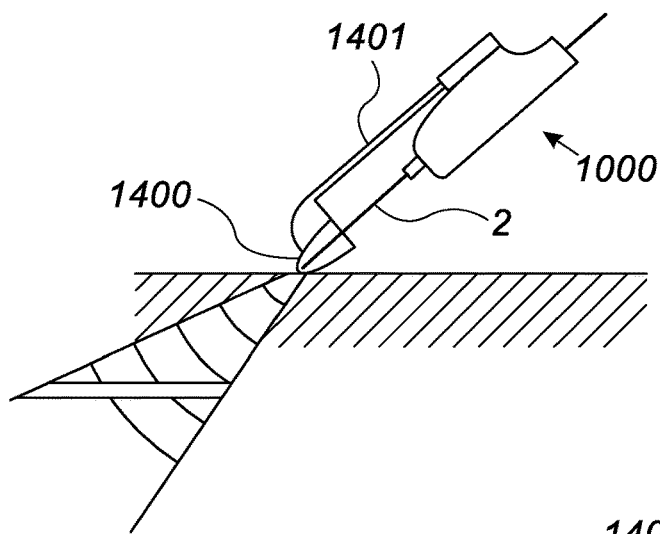
Figure 13D:
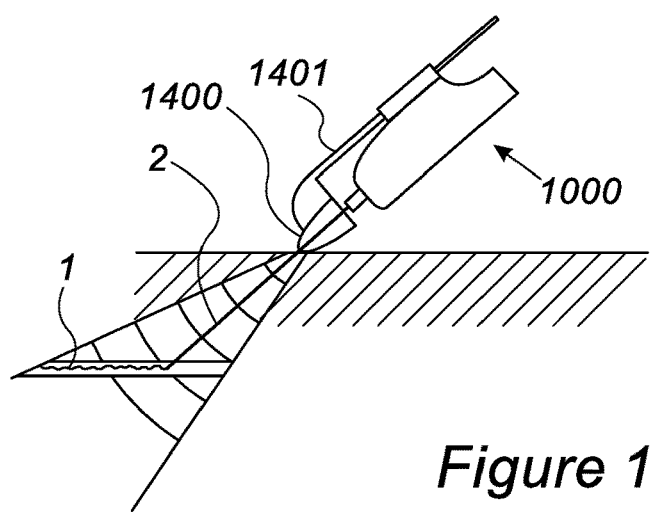

In some embodiments described in FIGS. 13A-13D, an ultrasound transducer 1400 may be slideably located at the tip of needle 2 of device 1000. More particularly, FIG. 13A is a simplified 3D drawing of device 1000 with needle 2, transducer 1400 around the tip of needle 2, arm 1401 connected to transducer 1400, and slideably connected to connector 1402. FIG. 13B shows transducer 1400 made of two parts, which can be separated to remove it off needle 2 or a sheath that may have been placed over the needle. This may allow the needle or the needle/sheath to be removed or replaced. FIGS. 13C and 13D are simplified side views of device 1000 with a longitudinal section of the tissue. FIG. 13C shows device 1000 before skin puncture, and FIG. 13D shows device 1000 with needle tip in the target vessel, and a deployed guidewire in the blood vessel. Although described above as being made of two parts, transducer 1400 may be made of more than two parts, or alternatively of one part further comprising a longitudinal slit, such that it may be positioned with the needle at its center, slid over the needle during puncture, and easily removed following puncture.

In an embodiment, transducer 1400 is a Doppler ultrasound transducer with a narrow beam, which provides an audio or visual indication of the intensity of the sensed Doppler signal. The user may place transducer 1400 at the desired puncture site, and may tilt device 1000 in varying angles until he identifies the angle with the strongest signal, indicating the direction of the target vessel. The user then punctures through the skin until device 1000 deploys.

Figure 14:
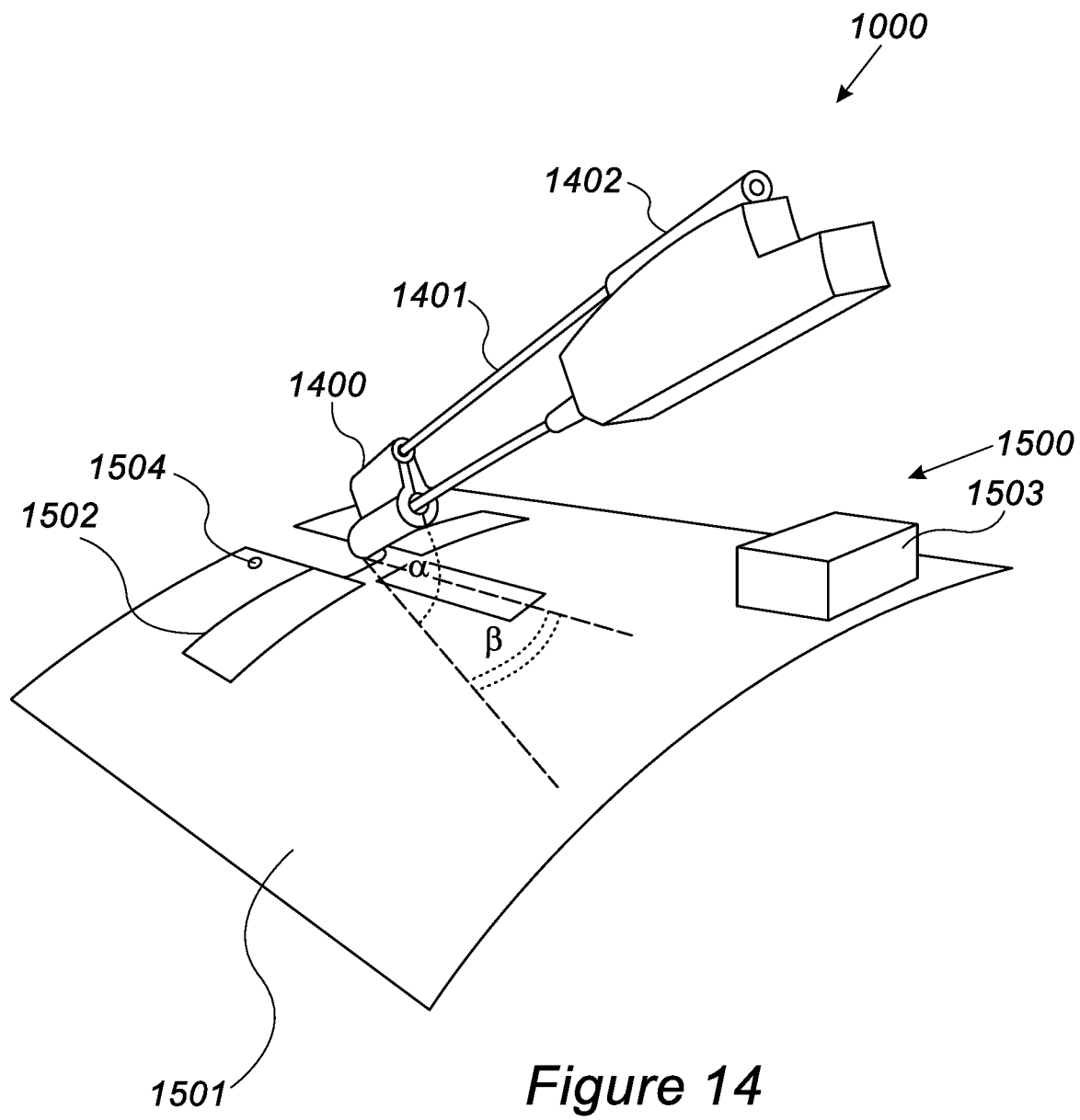
FIG. 14 shows a cannulation device having a guidance system in accordance with embodiments of the invention.

In an embodiment shown in FIG. 14, a guidance system 1500 is provided which includes the device described previously in FIGS. 13A-13D, a surface or mat 1501 on which are mounted one or more position sensors 1502, connected to a processor 1503, which is connected to indicator 1504. Position sensors 1502 may for example measure angles $\alpha$ and $\beta$ of device 1000 in relation to mat 1501. The distal end of transducer 1400 may be connected or secured to mat 1501 at a certain point such that it can pivot but not move in relation to mat 1501.

In use, the user may change the angles $\alpha$ and $\beta$ of device 1000 relative to mat 1501 by moving it from side to side, and forward and backward. During this movement, processor 1503 may register the position of device 1000 together with the corresponding signal measured by transducer 1400 at each position. Processor 1503 may then analyze the data to find the position in which the maximal signal is sensed. Processor 1503 can then either turn the indicator on (light, sound, or vibration) when that position is reached by the user, or it can use two or more indicators to guide the user to the correct position or angle (e.g. by directing him to move right, left, up or down).

In an embodiment, transducer 1400 may be a 3D ultrasound probe. An image of the 3D space imaged by the probe may be displayed on a screen, which may be part of device 1000 or separate from it. This image may be a holographic image, a 2D perspective view of the imaged 3D space, or any combination of cross sectional views derived from the 3D model. The reconstructed screen image may be created as if from the point of view of the user, the needle, or from any other angle.

Figure 15A:
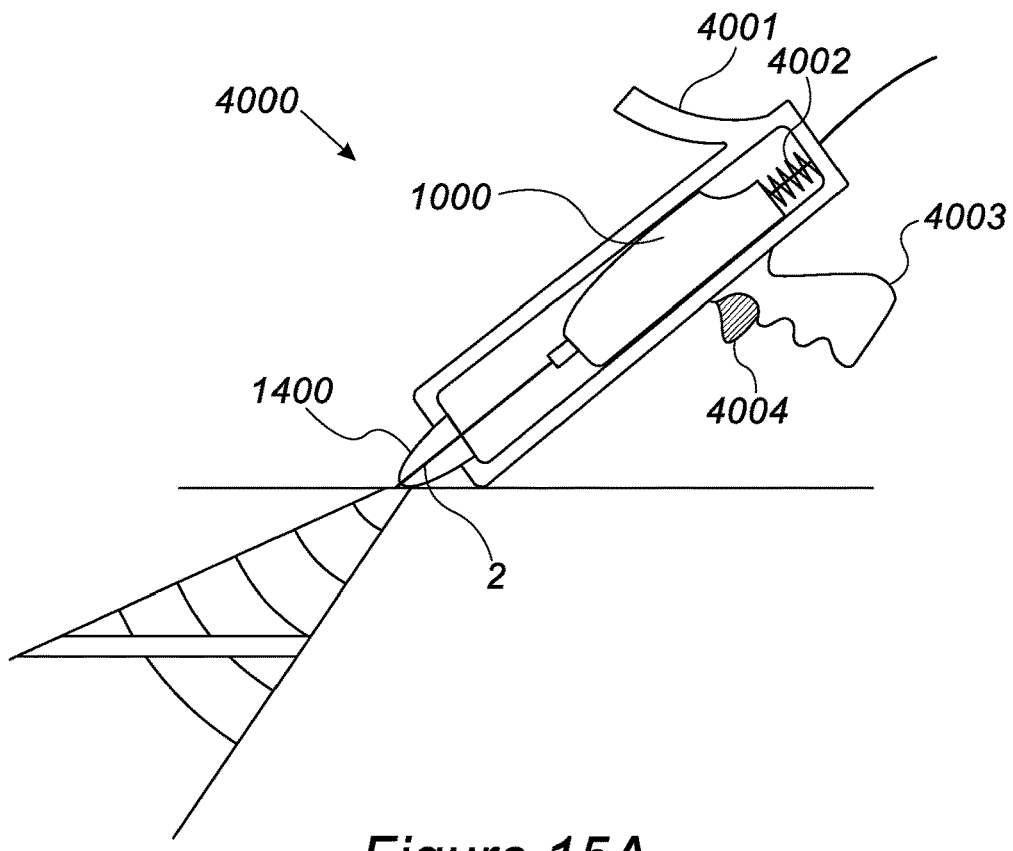
FIG. 15A shows a longitudinal cross section of a cannulation device in accordance with one embodiment of the invention.
Figure 15B:
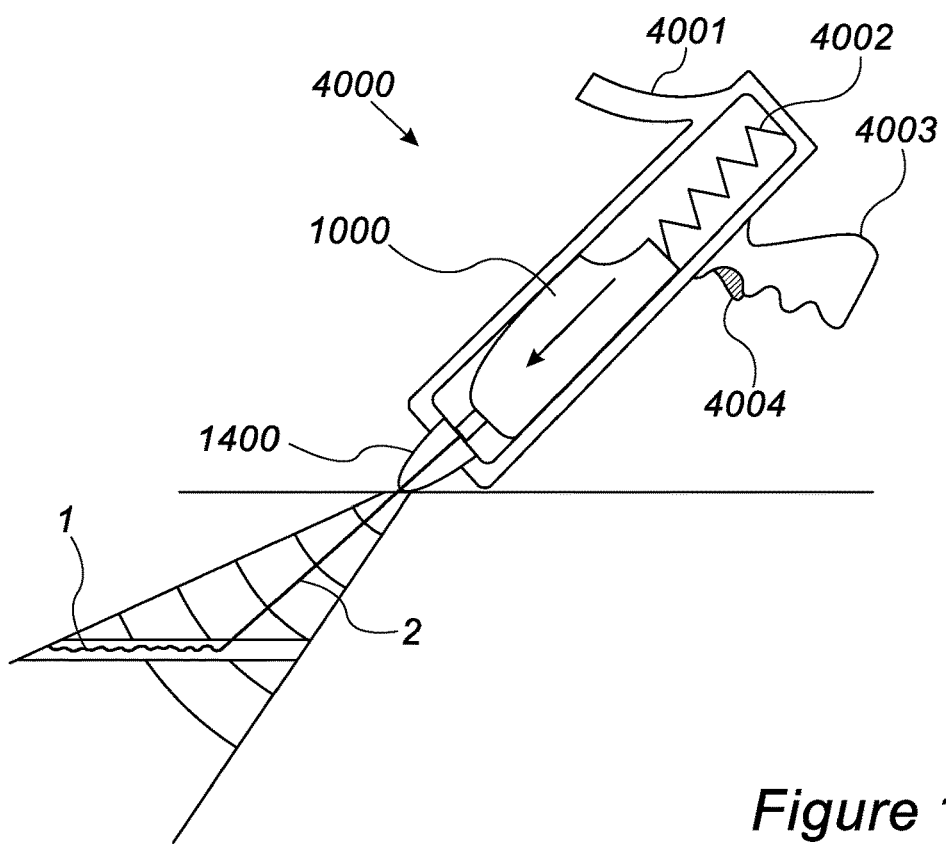
FIG. 15B shows a longitudinal cross section of a cannulation device in accordance with one embodiment of the invention.

In an embodiment described in FIGS. 15A and 15B, a device 4000 may comprise cannulation device 1000, transducer 1400, screen 4001, a spring 4002, a handle 4003, and a trigger 4004. Device 1000 may be slideably positioned within device 4000 with spring 4002 pushing it forward. Spring 4002 may be replaced by any other mechanism to push device 1000 forward, such as a motor or solenoid. Device 1000 can be abruptly advanced upon pulling trigger 4004 by the user.

In this embodiment, the imaging system provides an indication on screen 4001, showing where the needle will reach at the end of its travel.

The user may decide when the indication is correctly positioned within the vessel lumen, and pulls the trigger. Device 1000 may advance and deploy once needle 2 penetrates the blood vessel.

Robotic Systems

Device 1000 may be used in a robotic system to automatically detect the targeted blood vessel and deploy the needle, guidewire, and/or other blunting elements into the targeted blood vessel.

Figure 16:
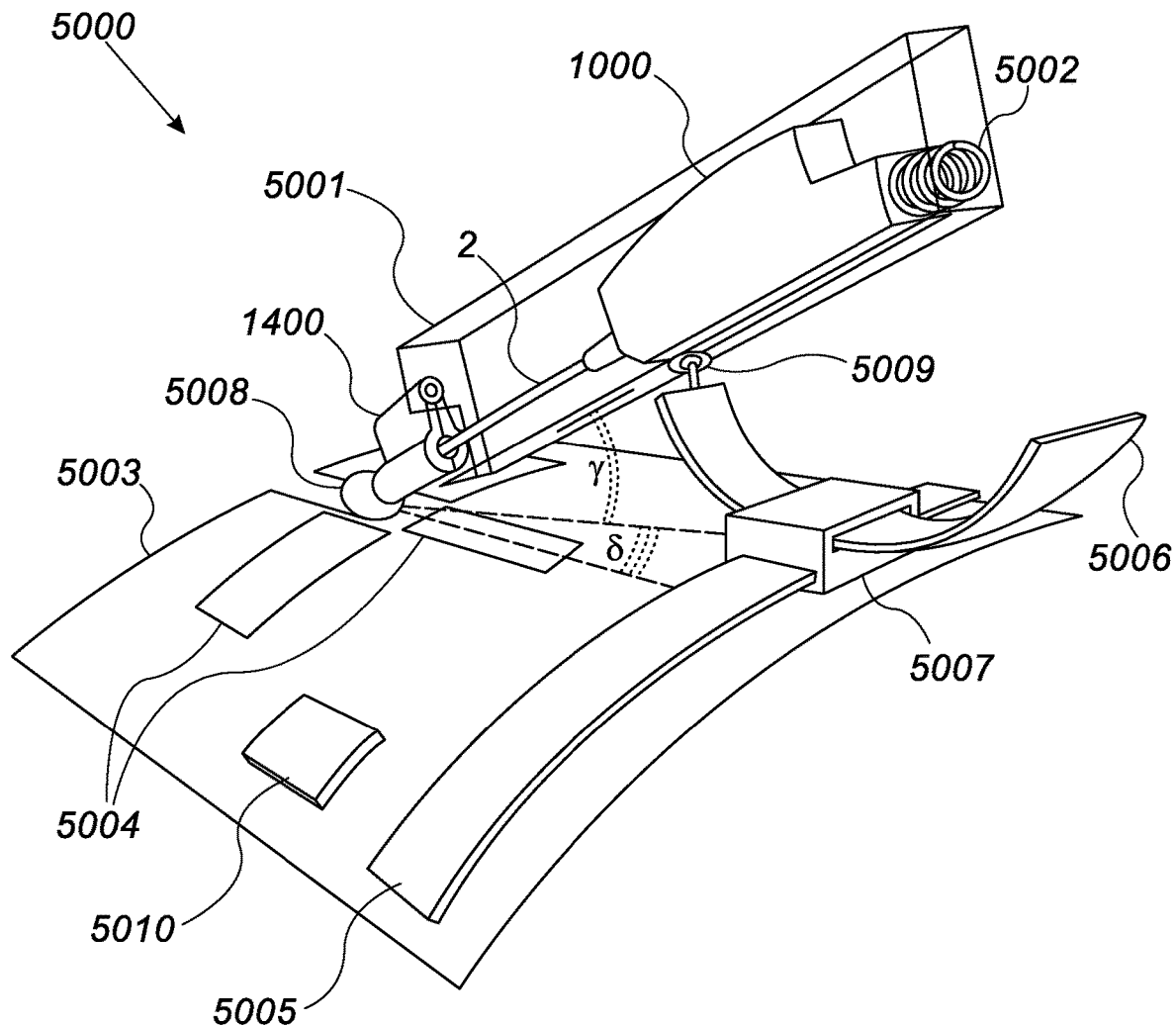
FIG. 16 shows a cannulation device having a robotic system in accordance with embodiments of the invention.

In an embodiment shown in FIG. 16, a system 5000 may include imaging means, as well as means for automatically changing the orientation of device 1000, and for advancing device 1000. More specifically, FIG. 16 is a schematic 3D drawing showing system 5000 comprising device 1000 slideably disposed within case 5001, while being pushed forward by push element 5002, as well as needle 2 and transducer 1400, which is pivotally connected to mat 5003, optionally using pivot element 5008. On mat 5003 are sensors 5004, and strip 5005. A linear motor 5007 may slide over strip 5005, and over another strip 5006 which is pivotally connected to case 5001. A CPU 5010 located on mat 5003, may be connected to sensors 5004, device 1000, transducer 1400, and linear motor 5007. Push element 5002 may be an electrical motor, linear or rotary, a solenoid, or a spring with a "brake" controlling the extent of its advancement.

In use, the system may be placed over a patient's skin, in the vicinity of a target vessel. Initially the system may perform scanning by measuring the Doppler signal returned to transducer 1400 while changing the angle of device 1000 relative to the skin to identify the angle towards the target vessel. This may be done by linear motor 5007 sliding over strip 5005 which may change angle δ, and by sliding strip 5006 through linear motor 5007 which changes angle γ. In some embodiments, angle γ is kept constant while angle may change over its complete range, then angle γ may change slightly, and the scanning may repeat over angle δ, and so on.

The Doppler signal measured by transducer 1400, may be recorded by CPU 5010 for each device position. Once the angle at which the signal is maximal is identified, the system may return case 5001 to that angle, and advance device 1000 straight into the patient's skin, until the device deploys. Device 1000 may send a signal to CPU 5010 indicating that deployment occurred, and CPU 5010 may immediately stop advancement of device 1000.

Alternatively or additionally, the indication of deployment from device 1000 to CPU 5010 may prompt slight elevation of the needle tip and decrease of its angle with the vessel's long axis, thus moving the needle tip away from the distal vessel wall, and bringing the blunt side of the needle bevel closer to the proximal vessel wall.

The system may then cease its operation and let the user continue from there, or alternatively it may automatically advance a sheath into the vessel, or draw blood from the blunted needle.

The system may be able to distinguish between a maximal arterial signal and a maximal venous signal, and choose the maximal signal according to the user's preference of an arterial or venous target vessel.

In an embodiment, a vessel cannulation system may comprise a 3D imaging system, a robotic arm, and device 1000. The imaging system may scan the target area using an ultrasound probe and creates a 3D model of the vessels in it. The vessel cannulation system may choose the target vessel according to the user's preference of arterial vs venous. In contrast with other previously described robotic systems, the cannulation system may then advance the needle abruptly to the exact location of the vessel lumen, at a high acceleration and speed with the aim of puncturing the vessel within 50-200 ms of the beginning of movement towards the vessel, before the vessel has a chance to move, as often happens when the puncture takes a longer time. Optionally, the puncture process is divided into two phases, the first is skin puncture, and the second is vessel puncture, with an optional brief pause in movement between the two phases. In this case, the time mentioned above is measured from the second motion, when movement towards the vessel begins following the pause after the skin was penetrated. Optionally, the advancement mechanism is configured not to exceed a certain force, so that if device 1000 deploys before the estimated distance, the needle will not exert excessive force on the guidewire in the vessel.

Any of the above described devices may optionally additionally comprise means for identifying the authenticity and/or validity of disposable components used with it. Such means may for example include an RFID or barcode reader on the capital equipment unit, and an RFID chip or barcode on the disposable unit. If the disposable is found invalid or expired, the capital equipment unit will be rendered unusable, and will not become usable again until a disposable with an authentic non-expired disposable is presented to the reader.

Expandable Sheath

Expandable sheaths that are known in the art suffer from various shortcomings. For example, some sheaths described in the art have rigid longitudinal beams connected by an elastic material. In such sheaths, the expansion of the sheath may occur between a specific pair of beams instead of homogenously between all beams. In some sheaths, the dilator, or catheter placed to expand the sheath, could exit via the side of the sheath. Also, some such sheaths would buckle and collapse upon removal of the catheter from within their lumen. Manufacturing cost for expandable sheaths having a complex structure may also be high.

The expandable sheaths of embodiments of the present invention may overcome these shortcomings. In particular, the expandable sheath of embodiments of the present invention may provide axial rigidity, resistance to buckling, radial expandability, homogenous expansion around the sheath, improved sealing, and are manufactured in a much lower cost. In some embodiments of the present invention, the expandable sheath may be used in combination with cannulation devices of the invention. In fact, the expandable sheath and cannulation device may complement each other and may be considered a system for vascular access. For example, the expandable sheath may be attached to the distal end of device 1000, covering the needle, which may be attached to luer adapter 11. After puncture of the vessel by the needle, automatic deployment of the guidewire, and insertion of the sheath into the vessel, the needle and guidewire may be removed from within the sheath shaft, leaving the expandable sheath in the vessel. In other embodiments, a rigid large diameter sheath may be used in conjunction with the expandable sheath. For example, the rigid large diameter sheath may be fitted with a mandrel, where the rigid large diameter sheath may be inserted into the expandable sheath to further expand the expandable sheath.

Spiral Connections

Figure 17:
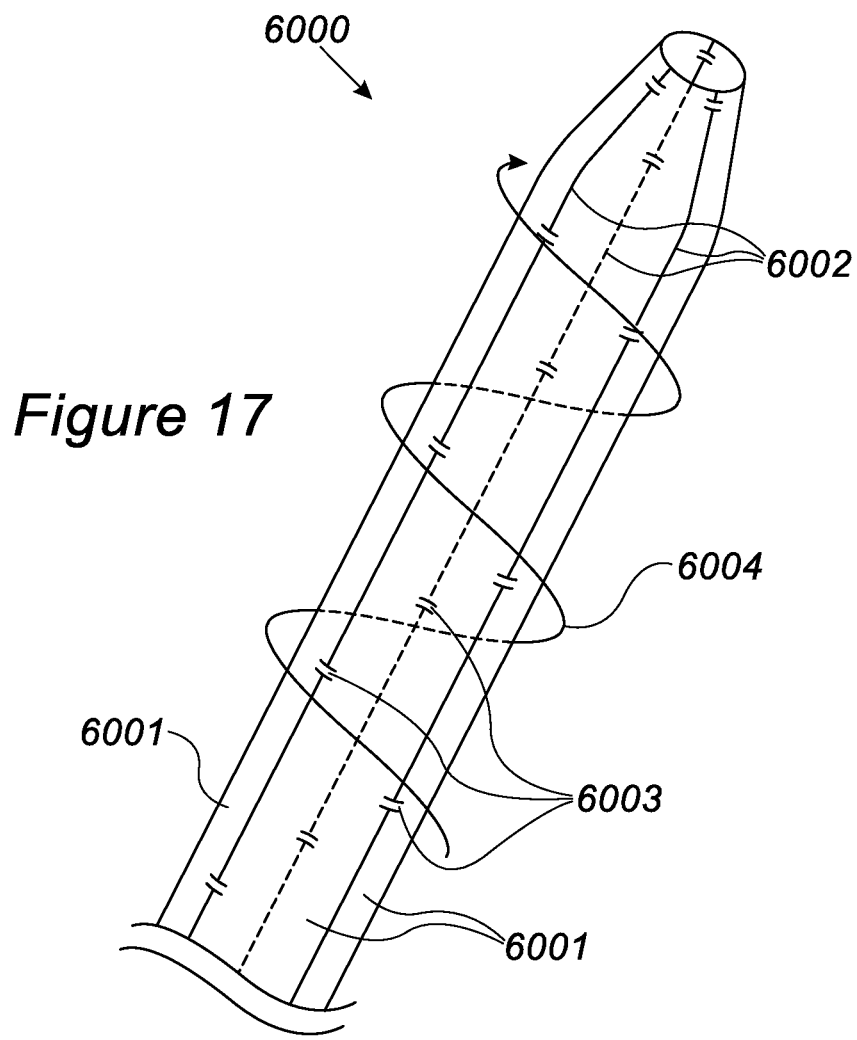
FIG. 17 shows an expandable sheath in accordance with an embodiment of the invention.

FIG. 17 shows an embodiment of expandable sheath 6000 with spiral connections between the beams. More specifically, FIG. 17 is a simplified 3D depiction of the distal part of a single layer of expandable sheath 6000 comprising three beams 6001 separated by slits 6002. Connections 6003 may bridge between beams 6001, and may be arranged in a spiral around sheath 6000 as demonstrated by arrow 6004. In some embodiments, at the tip of the sheath, all beams are connected at the same level. Optionally, also near the sheath hub, at the level of the transition from the hub diameter to the needle diameter, there could be a connection between all beams at the same level.

The layer shown in FIG. 17 can be made of a relatively rigid material such as nylon or PTFE, while an additional, elastic layer, made of silicone, latex, polyurethane or other elastomer may be added to the rigid layer. The elastic layer may be either on the external, the internal or on both sides of the rigid layer. The spiral arrangement may prevent buckling of the sheath during insertion, and at the same time prevents dilation from occurring only between one pair of beams, as may happen when all connections are made at the same levels.

Manufacturing this sheath may be done for example by laser cutting the pattern of slits shown in FIG. 17 into the rigid layer, sparing the connections. This layer can then be post processed for making the taper at the tip and flare at the hub, and then dipped to add the elastic layer. Alternatively this sheath may be manufactured by micro molding.

Outer Support

In an alternative embodiment, the beams are not inter-connected. Instead, external support may be provided during insertion into the tissue, to that part of the sheath which is outside the skin, thus preventing its buckling. This may be done for example by a balloon inflated around the sheath, a highly viscous pad, or a telescopic or peelable element, which may remain outside the body during insertion. In an alternative embodiment, the beams are not inter-connected. Instead, external support may be provided during insertion into the tissue, to that part of the sheath which is outside the skin, thus preventing its buckling. This may be done for example by a balloon inflated around the sheath, a highly viscous pad, or a telescopic or peelable element, which remains outside the body during insertion.

Rigid and Elastic Layers Forces

The force required to expand the rigid layer may be determined by the layer material, thickness, number and width of beams, distance between the connections, and the connections dimensions. This force should optimally be as small as possible, but high enough to prevent beams from disconnecting due to axial load during insertion into tissue.

The force required to expand the elastic layer may be determined by its material and thickness. This force may optimally be high enough to prevent a dilator/catheter from exiting through the side of the sheath.

Inner Sheath

In an embodiment, initial expansion of the sheath may be done by insertion of a rigid inner sheath with an outer diameter equal to the internal diameter of the expanded sheath, and the maximal possible internal diameter.

This internal sheath may be inserted over a rigid dilator, which may then be removed. This internal sheath may additionally have a valve or connector at its proximal end to serve as the valve or connector of the dilated sheath.

Using such an internal sheath may ensure that the expandable sheath does not buckle during removal of catheters or tools from it.

Overlapping Sheath Hub and Needle Hub

Figure 18:
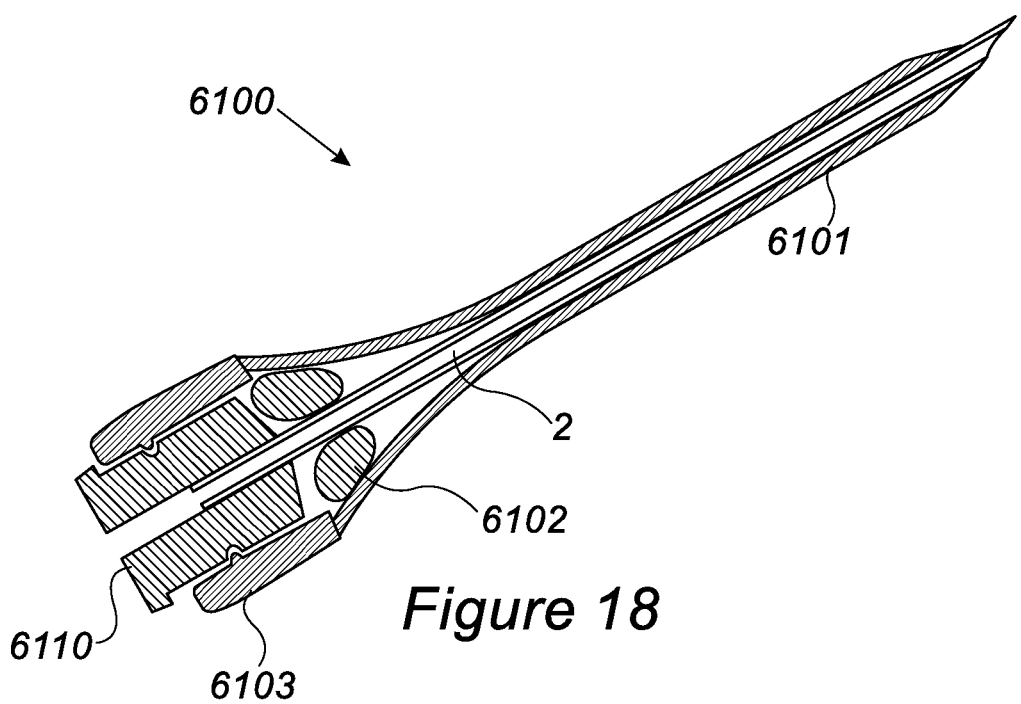
FIG. 18 shows another expandable sheath in accordance with an embodiment of the invention.

In an embodiment shown in FIG. 18, an expandable sheath 6100 is described, in which the sheath hub overlaps with the needle hub. More specifically, FIG. 18 is a schematic longitudinal cross section through sheath 6100 comprising sheath shaft 6101, sheath valve 6102, and sheath hub 6103. Needle 2 is shown having needle hub 6110. Overlapping of the hubs may enable keeping the overall needle 2 length shorter while maximizing the sheath shaft length.

Needle hub 6110 may have a mechanism for locking it to cannulation device 1000, such as a luer lock or a snap connector. Sheath hub 6110 may have the same. Alternatively both hubs may separately lock onto cannulation device 1000, or may have a connection (snap or lock) between them, while only one of them locks to cannulation device 1000.

Sheath Valve

Hemostatic valves in large diameter sheaths usually have a complex structure due to a requirement on the one hand to provide sufficient support that may withstand blood pressure over a large valve surface area, and on the other hand may be able to compress and allow a large bore tool or catheter to pass through them.

In this embodiment, a valve 6102 shaped as a ring, a toroid, or a sphere with a central hole may be used in the expandable sheath. This valve may be placed within the hub 6103 but may be connected such that when pushed by a tool or catheter, it may protrude partially or fully into the expandable area, where there is more space for it, and therefore it does not require a complex structure, and is cheaper to manufacture. The force applied by the valve against the expandable sheath shaft can also aid in the initial expanding of the sheath.

Pull Sheath Design

Figure 19:
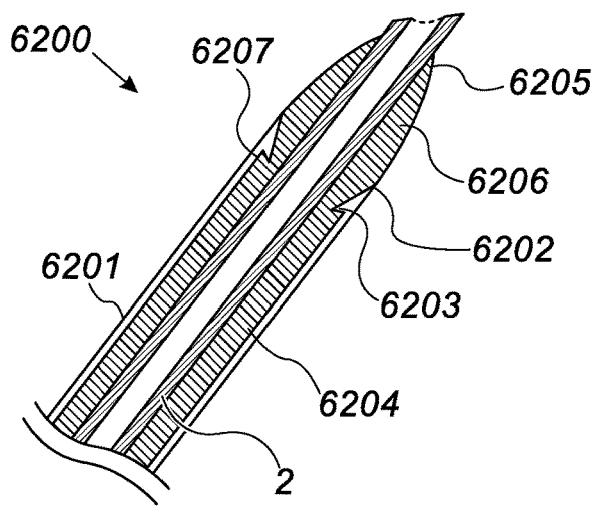
FIG. 19 shows yet another expandable sheath in accordance with an embodiment of the invention.

In yet another embodiment shown in FIG. 19, an expandable sheath 6200 is shown, which is based on pulling instead of pushing during insertion.

More specifically, FIG. 19 is a schematic longitudinal cross section of sheath 6200 comprising outer sheath shaft 6201 having distal tip 6202 and step 6203. Inner sheath 6204 consists of distal tip 6205, bulb 6206, and shoulder 6207. Bulb 6206 is configured to be collapsible, for example by splitting it longitudinally and removing some of its material. Step 6203 of outer sheath 6201 is configured to engage with shoulder 6207 of inner sheath 6204.

Sheath shaft 6201 may be made of at least two layers as described above for the embodiment in FIG. 17, but does not require high axial rigidity and therefore does not require the connections between beams. Although less optimal, it can even be optionally made of just one expandable layer, but must not be longitudinally stretchable.

Inner sheath 6204 may be made of a rigid or semi rigid polymer such as nylon or PTFE, or a metal such as SS. Optionally inner sheath 6204 may be an integral part of needle 2. In some embodiments, needle 2 may have step 6203 as part of the needle itself.

In use, all the above elements may be used as one to penetrate a lumen. Since step 6203 is engaged with shoulder 6207, distal tip 6202 of sheath 6200 may be pulled into the tissue by needle 2 and inner sheath 6204, both rigid structures, instead of sheath 6200 being pushed into the tissue from its proximal end (i.e. from its hub end). Stated differently, in other embodiments, because the sheath is not connected to the distal end of the needle, it must have sufficient axial rigidity to resist friction, and not collapse when inserted into the tissues, such as skin, subcutaneous fat, fasciae, etc., which may be in the way of penetrating a vessel. In an embodiment, step 6203 of outer sheath 6201 is being pulled forward (into the tissue) by shoulder 6207 of inner (rigid) sheath 6204 (or needle 2, if it is integral to the inner sheath as described above), so that the rigid inner structure 6204 or rigid needle shaft takes up all the axial load. Therefore, the sheath 6200 may not buckle when inserted.

Once inside a lumen, needle 2 may be removed, allowing bulb 6206 to collapse towards its center, which makes removal of inner sheath 6204 easy. After removing inner sheath 6204, a dilator or catheter, or a large bore rigid inner sheath may be inserted into expandable sheath 6200 to expand it.

External Sheath

Figure 20:
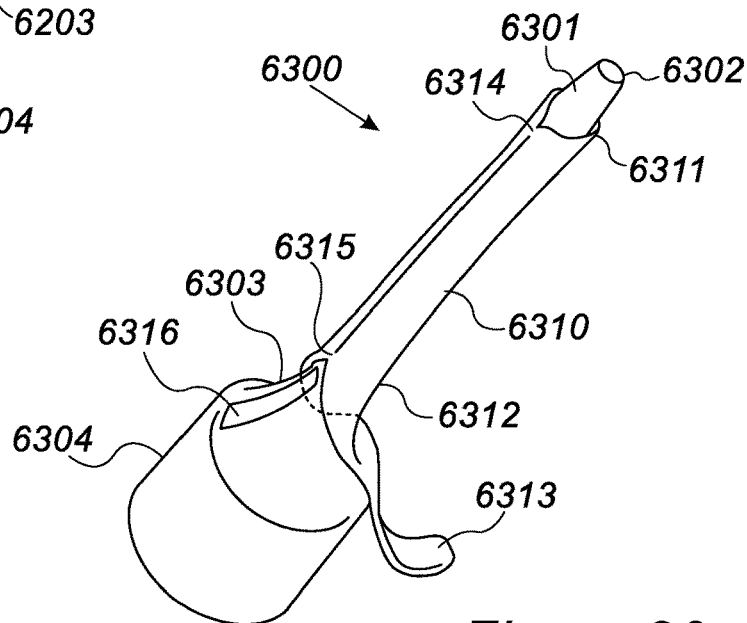
FIG. 20 shows an expandable sheath in accordance with an embodiment of the invention.

In an embodiment shown in FIG. 20, an additional external sheath may be used to provide support to the expandable sheath during insertion into the tissue, in order to prevent it from buckling, without the need for creating connections between the beams.

More particularly, FIG. 20 is a schematic 3D depiction of sheath 6300 consisting of expandable sheath 6301, and external sheath 6310.

Expandable sheath 6301 is similar to expandable sheaths described above, in that it may be made of one or two layers, which may be radially expandable and have a degree of axial rigidity. However expandable sheath 6301 does not need to have a high degree of axial rigidity, and therefore may for example comprise several beams without any connections between them. Expandable sheath 6301 has a tapered distal tip 6302, and a proximal end 6303, which is flared and connects to hub 6304.

External sheath 6310 may have distal tip 6311, proximal end 6312, handle 6313, an optionally distal connection 6314 and proximal connection 6315. An optional support element 6316 may connect proximal end 6312 of external sheath 6310 to hub 6304.

External sheath 6310 may be an elongate sheath with at least one longitudinal slit, which may be bridged by connections 6314 and 6315.

In use, sheath 6300 may be inserted over a needle into the tissue prior to entering into the vessel. Support element 6316 may prevent sheath 6310 from sliding over expandable sheath 6301. Once in a lumen, support element 6316 may be removed by pulling it, and external sheath 6310 may be pulled backwards at handle 6313, tearing at connections 6315 and 6314. The needle may then be removed, and expandable sheath 6301 may be ready to be expanded in the tissue.

Tear-Away Option

Any of the above described sheaths may optionally additionally be tearable, such that after placement of a catheter through such expandable sheath, the sheath may be torn and removed, leaving the catheter in the vessel. In some embodiments, the tearable shafts are made using tubes with a wall thickness between 0.01 mm to 0.3 mm, between 0.05 to 0.2 mm, between 0.1 to 0.15 mm. In some embodiments, the wall is less than 0.15 mm, less than 0.1 mm, less than 0.05 mm, or less than 0.01 mm.

Various additional embodiments for improved expandable sheaths are described in FIGS. 21-24. These embodiments may be made of a single, typically inelastic material, and may provide increased axial strength while keeping total wall thickness low and minimizing manufacturing costs. Such materials may include polytetrafluoroethylene (PTFE), polyether block amid (PEBAX), polyether ether ketone (PEEK), polypropylene, etc. When referring to inelastic, it is meant that any expansion of the sheaths described in FIGS. 21-24 may be achieved by a change in their conformation, or in other words by unfolding, rather than by stretch of their material as was described for embodiments in FIGS. 17-20.

Figure 21A:
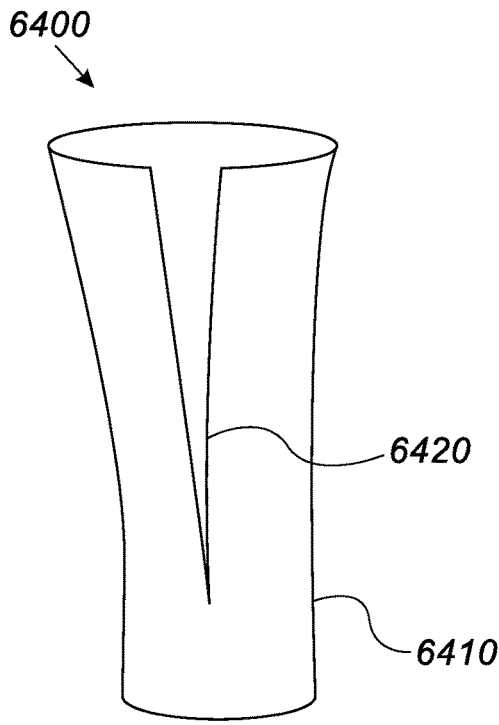
FIG. 21A shows a 3D schematic depiction of a tube in accordance with an embodiment of the present invention.
Figure 21B:
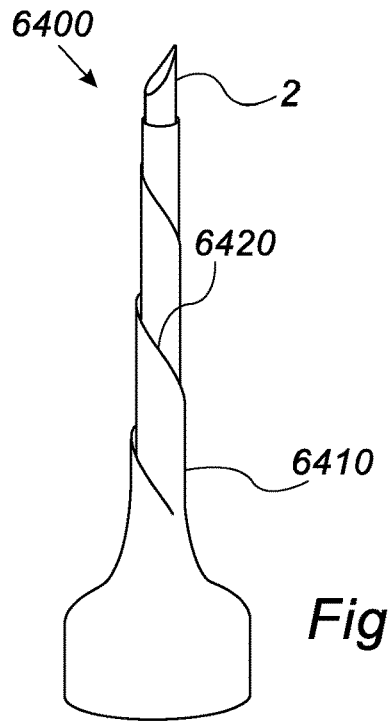
FIG. 21B depicts a spirally folded sheath in accordance with an embodiment of the present invention.

FIGS. 21A-B depict a sheath 6400 made of a longitudinally cut tube 6410 which may be folded spirally along the longitudinal cut.

More particularly, FIG. 21A is a 3D schematic depiction of tube 6410 from which sheath 6400 may be made. Tube 6410 may be made of an inelastic polymer, which also has some shape memory, such as polypropylene. For example, for the purpose of being inserted over an 18G needle and being expandable to 14 fr, an appropriate tube may have an internal diameter of 4.6 mm and a wall thickness of 0.05 mm or less. A longitudinal slit 6420 may be made along the longitudinal axis of tube 6410, sparing the hub region. This longitudinal cut may be pre-cut during manufacturing or a perforated line that may be torn apart by the user prior to being inserted over a needle. Tube 6410 may preferably be an inelastic layer made with inelastic polymers such as polytetrafluoroethylene (PTFE), polyether block amid (PEBAX), polyether ether ketone (PEEK), polypropylene, etc.

FIG. 21B shows external sheath 6400 spirally folded over needle 2 to reach an inner diameter closely fit to the outer diameter of the needle. The two sides of cut 6420 may overlap and each side of slit 6420 to create a spiral around needle 2.

In some embodiments, tube 6410 may be dipped in an elastic material such as polyurethane or silicone to create an elastic outer layer. This may create a smoother outer surface, and enable sheath 6400 to expand while maintaining fluid seal along the sheath. As such, this process may create an expandable sheath. Alternatively, such an elastic outer layer may be manufactured by sliding an elastic tube over tube 6410, shrinking a heat shrinkable tube over it, or by other methods known in the art. When expanded, sheath 6400 may return to its initial diameter as in FIG. 21A. Therefore, in operation, after the insertion of the expandable sheath and needle into a vessel, the needle may be removed, allowing the expandable sheath 6400 to expand and accommodate intravascular devices, such as central catheters, balloon catheters, etc.

In another embodiment, shown in FIGS. 22-24, longitudinal corrugations may be used in the tube to create a sheath with high axial strength.

The corrugations of the present invention may be of various number, size, and shape, from multiple microcorrugations, to a single large corrugation or fold.

FIGS. 22A-22D depict a sheath with multiple microcorrugations in accordance with embodiments of the present invention.

Figure 22A:
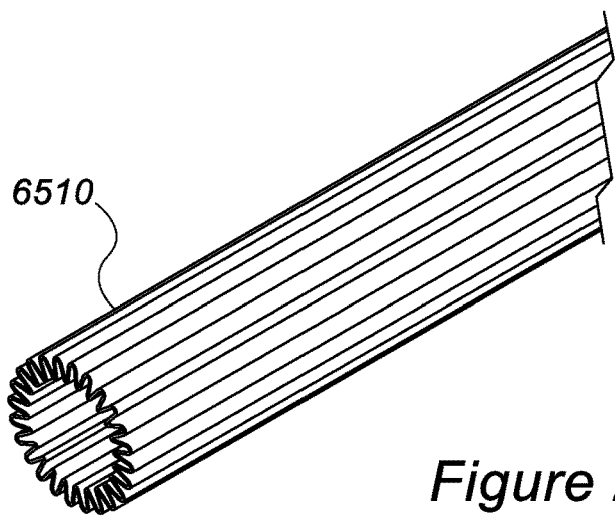
FIGS. 22A-22D show a sheath with multiple micro-corrugations in accordance with an embodiment of the present invention.

More particularly, FIG. 22A is a 3D depiction of tube 6510 from which expandable sheath 6500 (not shown) is made.

Figure 22B:
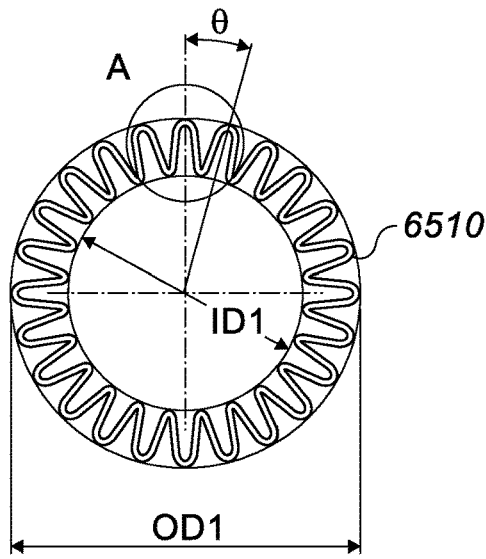

FIG. 22B is a transverse cross section of tube 6510, in which ID1 is the internal diameter of tube 6510 in its crimped state, which in some embodiments may be in a close fit to the outer diameter of the needle. In some embodiments, ID1 of tube 6510 in its crimped state may be between 0.3 mm to 3 mm, preferably between 0.5 mm to 1.5 mm. For example, FIG. 22B shows an ID1 of ~1.3 mm. In some embodiments, the expanded internal diameter of the sheath may be between 1 mm to 7 mm, preferably between 2 mm to 5 mm. For example, FIG. 22B shows a tube capable of expanding to achieve an internal diameter of 4.6 mm. The internal diameter of the tube may vary depending on the gauge of the needle and the application for which it is used.

As shown in FIG. 22B, OD1 is the outer diameter of tube 6510 in its crimped state. In some embodiments, the OD1 of tube 6510 in its crimped state may be between 0.5 mm to 4 mm, preferably between 0.7 mm to 2.0 mm. For example, FIG. 22B shows tube 6510 having an OD1 of ~1.9 mm. In some embodiments, the expanded outer diameter of the sheath may be between 1.2 mm to 7.5 mm, preferably between 2 mm to 5 mm. The expanded diameter of the tube may vary depending on the object (catheter) that may be inserted within it.

Angle θ is the angle around the circumference of tube 6510 occupied by each individual corrugation. In some embodiments, Angle θ is between 5 degrees to 30 degrees, between 12 degrees to 25 degrees, or between 15 degrees to 20 degrees. For example, in the case shown in FIGS. 22A-C Angle θ is 15 degrees, as there are 24 corrugations in total.

Figure 22C:
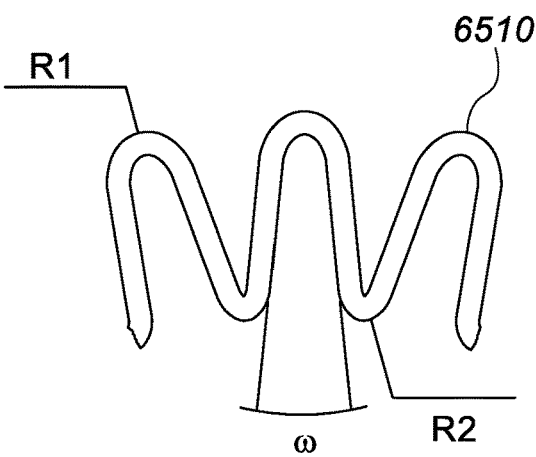

FIG. 22C is an enlarged view of detail A from FIG. 22B, showing angle ω formed between the two strips of tube around a single corrugation. R1 is the radius of this fold, which may be 0.01 mm-0.5 mm. R2 is the radius of the fold between two corrugations, may be 0.01 mm-0.5 mm. R1 and R2 may be equal or different.

Figure 22D:
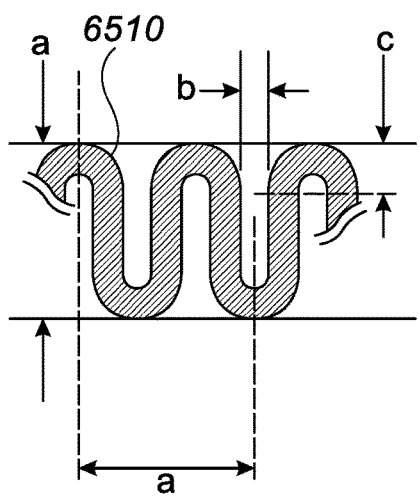

FIG. 22D is a schematic depiction of a segment of a crimped tube 6510, showing total crimped wall thickness "a", gap between two adjacent corrugations "b", and tube 6510 wall thickness "c".

In some embodiments, "a" may be between 0.1 mm and 0.4 mm, "b" may be between 0.01 mm and 0.5 mm, and "c" may be between 0.01 mm and 0.2 mm, preferably 0.02 mm to 0.05 mm.

To attain a desired ratio of sheath expansion "t" while maintaining a defined total wall thickness, each cross sectional segment of the non-expanded sheath may be able to lengthen by the desired ratio of expansion. Therefore each cross sectional segment of the crimped tube, equal to the total crimped wall thickness "a", may contain a length of tube wall equal to "a" times "t", in the expanded state.

In a case shown in FIG. 22D, the expansion ratio may be *3, as the folded sheath has a total thickness "a" of 0.3 mm, and each cross sectional segment 0.3 mm long may contain three folds of sheath, that can open to a total length of ~0.9 mm. This may be based on a tube wall thickness "c" of 0.05 mm, and gaps "b" of the same width between the folds.

Manufacturing of tube 6510 may be by extrusion. The sheath may either be extruded expanded, optionally with larger diameter folds at radii R1 and R2, then crimped or folded. Alternatively, tube 6510 may be extruded in its completely crimped state.

Figure 23A:
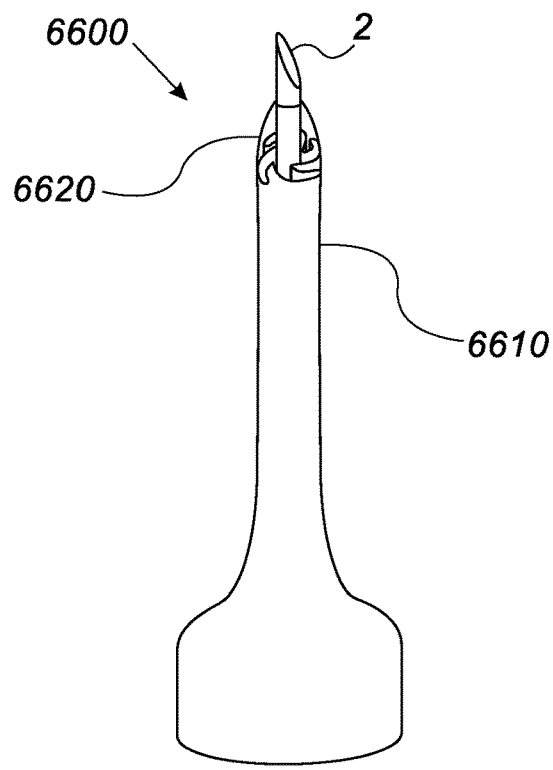
FIGS. 23A-23C show a sheath with larger corrugations in accordance with an embodiment of the present invention.
Figure 23B:
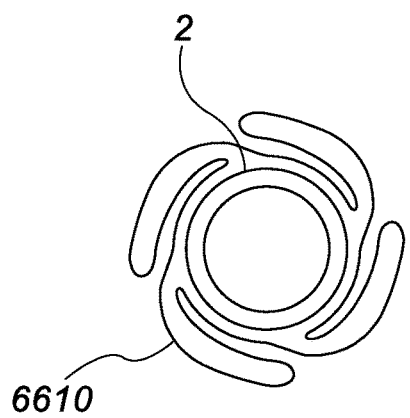
Figure 23C:
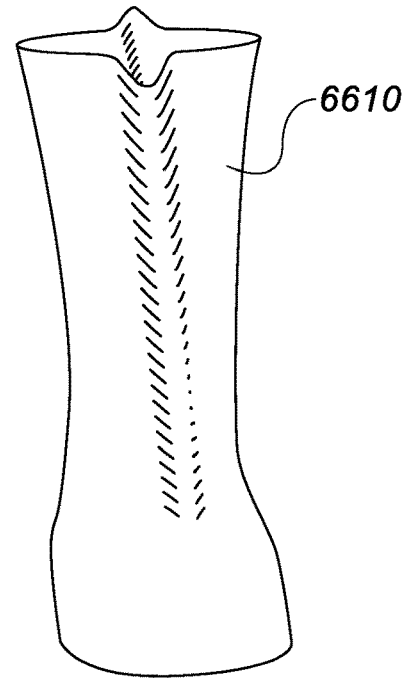

In another embodiment, FIGS. 23A-23C depict sheath 6600, which has larger and different type of corrugations. For example, FIG. 23A shows a folded tube 6610 with 4 corrugations.

More particularly, FIG. 23A is a 3D depiction of sheath 6600, showing needle 2, folded tube 6610, and taper 6620. The folding of tube 6610 creates a large "step" at the distal end of the tube, which necessitates creating a taper. This can be done for example by heat treatment of the distal tip of tube 6610, or by adding an elastic material to the end of the tube.

FIG. 23B is a cross section of crimped tube 6610, around needle 2.

FIG. 23C is a 3D depiction of tube 6610 before being folded into its crimped state. Tube 6610 can be manufactured already having the corrugations, its proximal end can then be flared to fit a hub, and the rest of its length may be crimped based on the extruded folds. As shown in FIG. 23B, the large corrugations are folded around needle 2, to create a low profile structure.

In another embodiment, FIGS. 24A-24G depict sheath 6700, which has a single longitudinal corrugation.

Figure 24A:
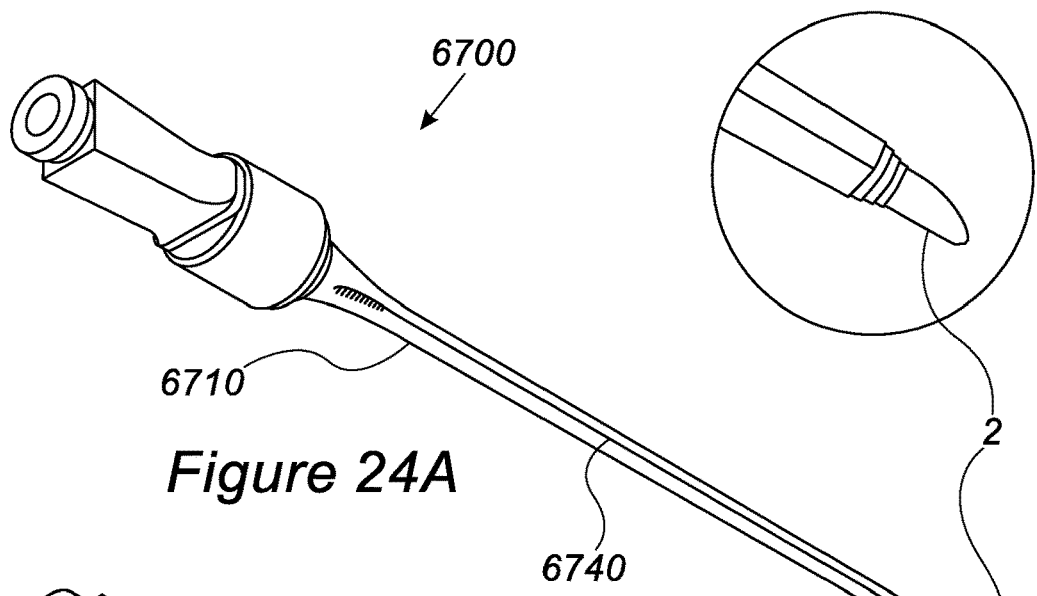
FIGS. 24A-24G show a sheath with a single longitudinal corrugation in accordance with an embodiments of the present invention.

More particularly, FIG. 24A is a 3D depiction of sheath 6700 in its crimped state, over needle 2. The expanded detail in the figure is the sheath's distal tip, in which particular attention is given to creation of a smooth taper, as will be detailed below.

Figure 24B:
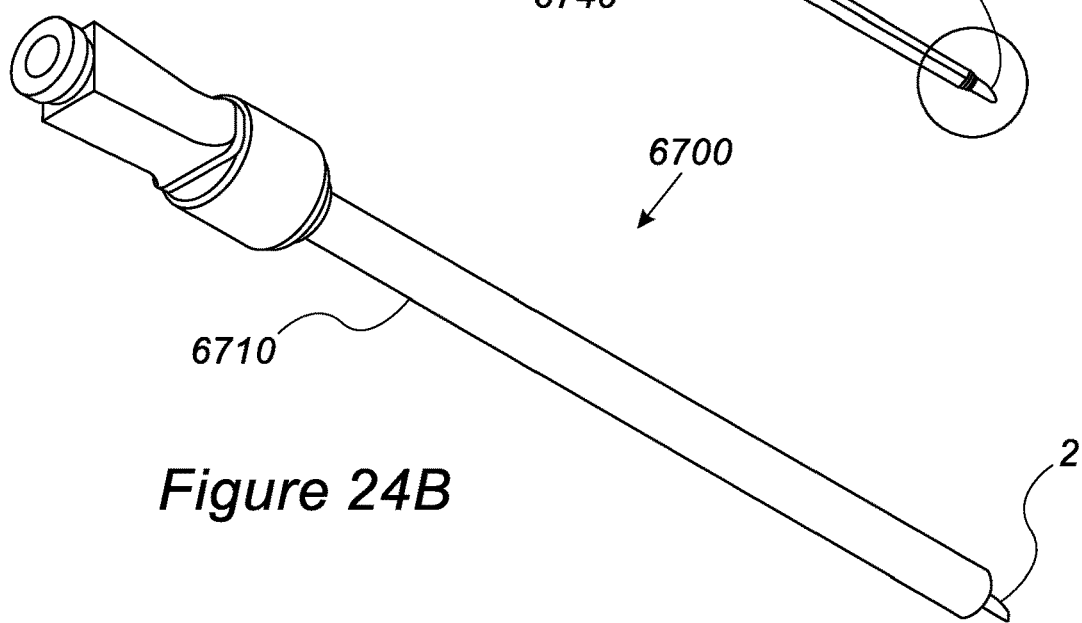

FIG. 24B is a 3D depiction of sheath 6700 in its expanded state. Although in some embodiments, needle 2 will not be inside sheath 6700 at this stage, it is shown as reference so that the change in sheath diameter can be appreciated.

Figures 24C, 24D:
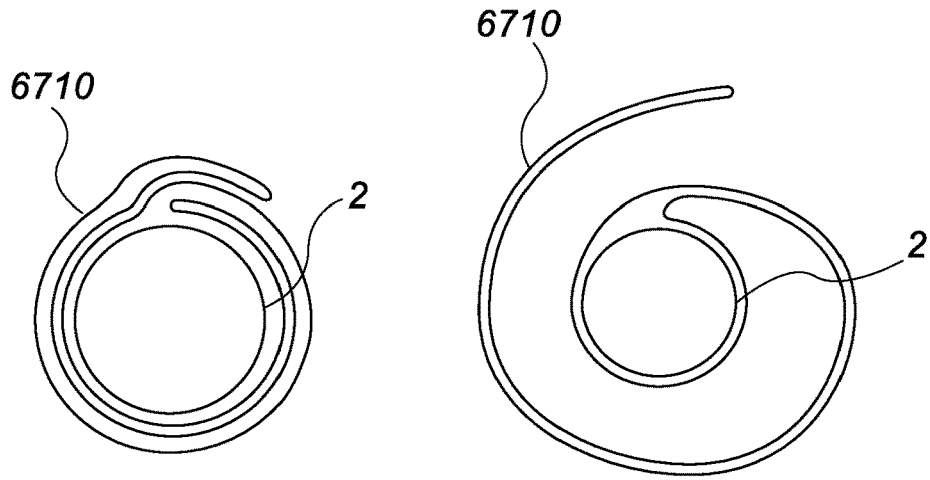

FIG. 24C is a schematic cross sectional view of crimped tube 6710 of sheath 6700 at around mid-distance between the sheath's hub to its tip.

A cross section of needle 2 is seen as a circle, surrounded by tube 6710, which is folded/rolled around needle 2, creating a first single layered loop around needle 2, and then continues twisting around the needle as a double layer. In some embodiments, the double layer may surround the needle for approximately one additional complete turn.

FIG. 24D is another depiction of the embodiment, a schematic drawing of the same cross section, in which tube 6710 is less tightly folded/rolled around needle 2, so that the layers are more clearly seen.

Figure 24E:
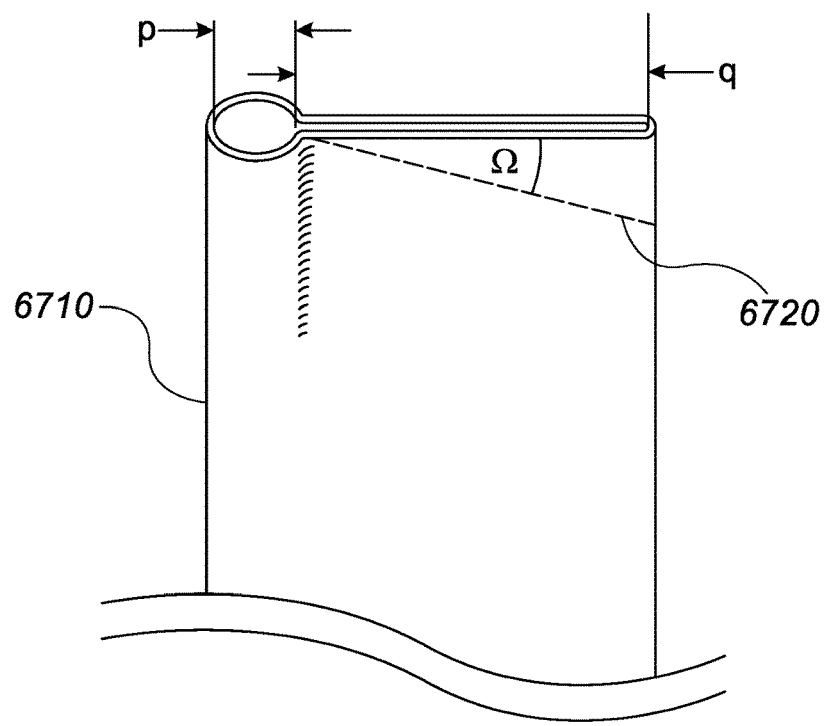
Figure 24F:
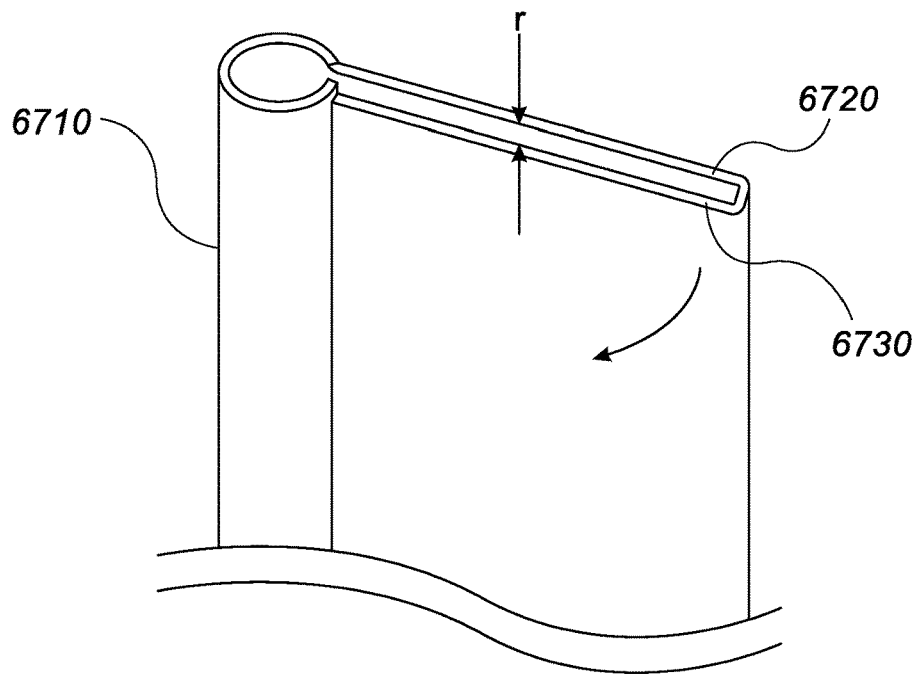

FIGS. 24E and 24F show additional details of the structure of a possible embodiment of sheath 6700.

FIG. 24E is a schematic 3D depiction of tube 6710, with one of its sides folded into a single layered cylinder with an internal diameter p, with a tight fit to needle 2. The remainder of the circumference of tube 6710 is folded so that its two layers are adjacent each other, to a length of q.

A dashed line 6720 denotes an optional trimming line of the end of tube 6710. Angle Ω may be the angle between line 6720 and the straight end of tube 6710.

Angle Ω may be between 0-45 degrees, preferably 5 to 30 degrees.

FIG. 24F shows the same tube 6710, in which the tube end was trimmed at line 6720, and wherein an additional trim was performed to shorten one of the layers of tube 6710 at line 6730, which may be parallel to line 6720, but may be at an angle to it. This additional trim may create a gap at a distance r between the ends of the two layers, so that a smoother taper can be created, as will be shown in FIG. 24G. The double-layered fold of tube 6710 is folded around the needle in the direction of the arrow, so that line 6720 spirals around the previous single layered fold.

Figure 24G:
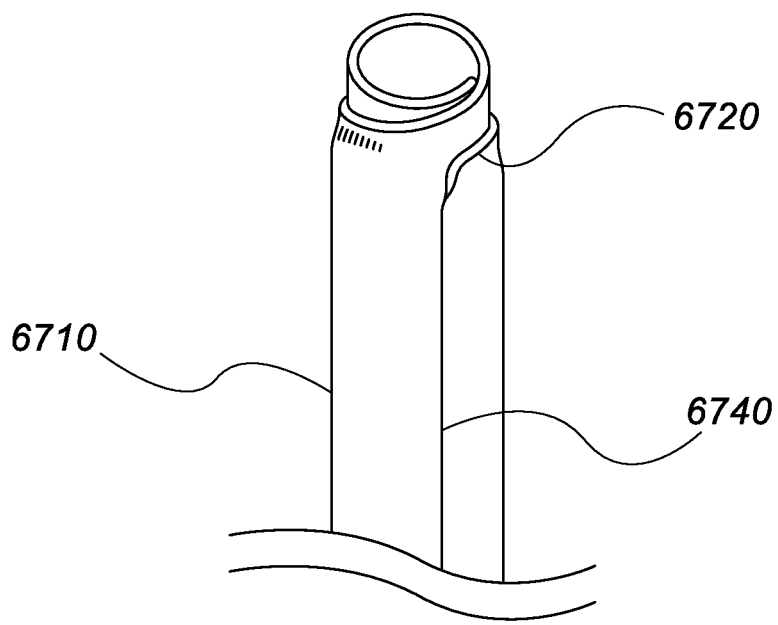

FIG. 24G is a 3D depiction of the distal end of tube 6710 of sheath 6700. The taper created by the trimmed distal end of tube 6710 is seen. Using heat treatment, adhesive, or other method, the ends of the folded tube 6710 may be tightened around the needle. The longer end along line 6720 may cover the shorter end along line 6730, aiding in creation of the taper. The free folded end of tube 6710 is parallel to the long axis of needle 2 and tube 6710, creating line 6740.

As mentioned above, the procedures performed using the devices of the invention may range from placement of central lines of various types (venous or arterial), through placement of smaller, peripherally inserted venous or arterial cannulae, to short term cannulation of a vessel or lumen (without leaving an indwelling catheter) for sampling body fluids, monitoring, or delivering substances.

Following is a description of specific features of embodiments enabling each of these.

Central Catheter Placement (CVC, PICC, Midline etc.)

a. Over Guidewire—Traditional Technique

In an embodiment, the minimal capability of the cannulation device may be utilized. A vessel cannulation device 1000 (or other) may be used for placing a guidewire only in a vessel lumen. A catheter with a dilator may then be inserted over the guidewire.

b. Through Expandable Sheath

In an embodiment, the full capability of the cannulation device may be utilized. A vessel cannulation device 1000 (or other) may be used for placing a guidewire in a vessel lumen. An expandable sheath which has been on the needle may be inserted into the vessel lumen over the needle and guidewire. The expandable sheath may be fitted over the needle prior to both being attached to the vessel cannulation device. After insertion into the vessel lumen, the cannulation device, the needle and the guidewire may be removed, leaving only the expandable sheath in the vessel. A catheter with or without a dilator is then inserted through the expandable sheath. Optionally, the expandable sheath may be torn away and removed if the catheter is to be left in place for a long time period.

c. Rapid Exchange Over Needle

Figure 25:
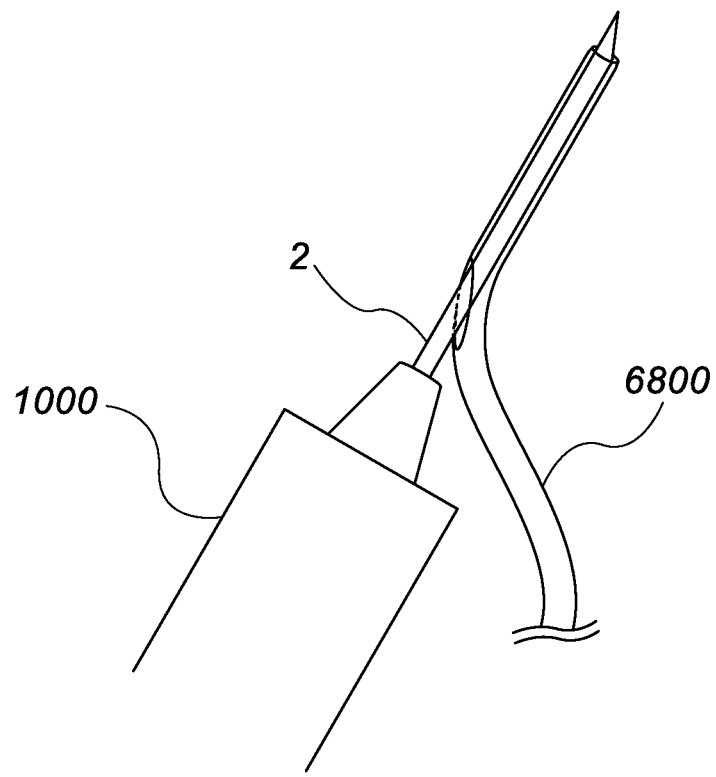
FIG. 25 shows the distal end of a cannulation device in accordance with embodiments of the invention where a catheter is placed over the needle at the distal end of the cannulation device.

In an embodiment, a catheter 6800 having a side opening in a "rapid exchange" fashion is placed over the needle 2 of vessel cannulation device 1000, as shown in FIG. 25. Once the device deploys in the lumen, central catheter 6800 is slid into the vessel lumen over the needle, and the needle and guidewire are removed with the cannulation device. In some embodiments, the sliding of catheter 6800 over the needle may be performed manually. Optionally, catheter 6800 may be inserted automatically by device 1000.

Optionally, a support element (not shown), consisting of a short rod, tube, or any other structure, may temporarily connect between the distal part of catheter 6800, and the proximal end of needle 2, its hub, or device 1000 (similar to support element 6316 of sheath 6300 in FIG. 20). This support element may assist in insertion of the needle and catheter through the tissues, preventing the catheter from being pushed backwards by friction with the tissues. Once catheter 6800 is in the vessel, the support element may be removed.

Peripheral IV Catheter Placement

When inserting a peripheral IV catheter, in some embodiments, the catheter may be pre-mounted over the cannulation device needle. Insertion can follow deployment any of the above described blunting mechanisms. Insertion may be manual, following the deployment, or may at least partially be performed automatically by the vessel cannulation device, as previously described, and may occur after or simultaneously with the automatic blunting element advancement.

Short Term Cannulation/Blood Sampling

In another embodiment, after the needle was blunted by any of the above methods, a port in the needle hub, or a port in the vessel cannulation device (in its needle adapter or in its body), can be used as a point of access to the vascular system, for blood drawing, drug or fluid administration, or monitoring.

Although described herein in the context of vascular cannulation, the devices and methods of the current invention may be used beneficially for cannulating any other body lumen.

Computer System

The term "computer" is intended to have a broad meaning that may be used in computing devices such as, e.g., but not limited to, standalone or client or server devices. The computer system may include, e.g., but is not limited to, a main memory, random access memory (RAM), and a secondary memory, etc. Main memory, random access memory (RAM), and a secondary memory, etc., may be a computer-readable medium (e.g., a non-transitory computer readable storage medium) that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The computer may also include an input device may include any mechanism or combination of mechanisms that may permit information to be input into the computer system from, e.g., a user. The input device may include logic configured to receive information for the computer system from, e.g. a user. Examples of the input device may include, e.g., but not limited to, a mouse, pen-based pointing device, or other pointing device such as a digitizer, a touch sensitive display device, and/or a keyboard or other data entry device (none of which are labeled). Other input devices may include, e.g., but not limited to, a biometric input device, a video source, an audio source, a microphone, a web cam, a video camera, and/or other camera. The input device may communicate with a processor either wired or wirelessly.

The term central processing unit "CPU" is intended to have a broad meaning that includes one or more processors, such as, e.g., but not limited to, that are connected to a communication infrastructure (e.g., but not limited to, a communications bus, cross-over bar, interconnect, or network, etc.). The term CPU may include any type of processor, microprocessor and/or processing logic that may interpret and execute instructions (e.g., for example, a field programmable gate array (FPGA)). The data processor may comprise a single device (e.g., for example, a single core) and/or a group of devices (e.g., multi-core). The CPU may include logic configured to execute computer-executable instructions configured to implement one or more embodiments. The instructions may reside in main memory or secondary memory. The CPU may also include multiple independent cores, such as a dual-core processor or a multi-core processor. The data processors may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible or non-transitory storage media.

Figure 26:
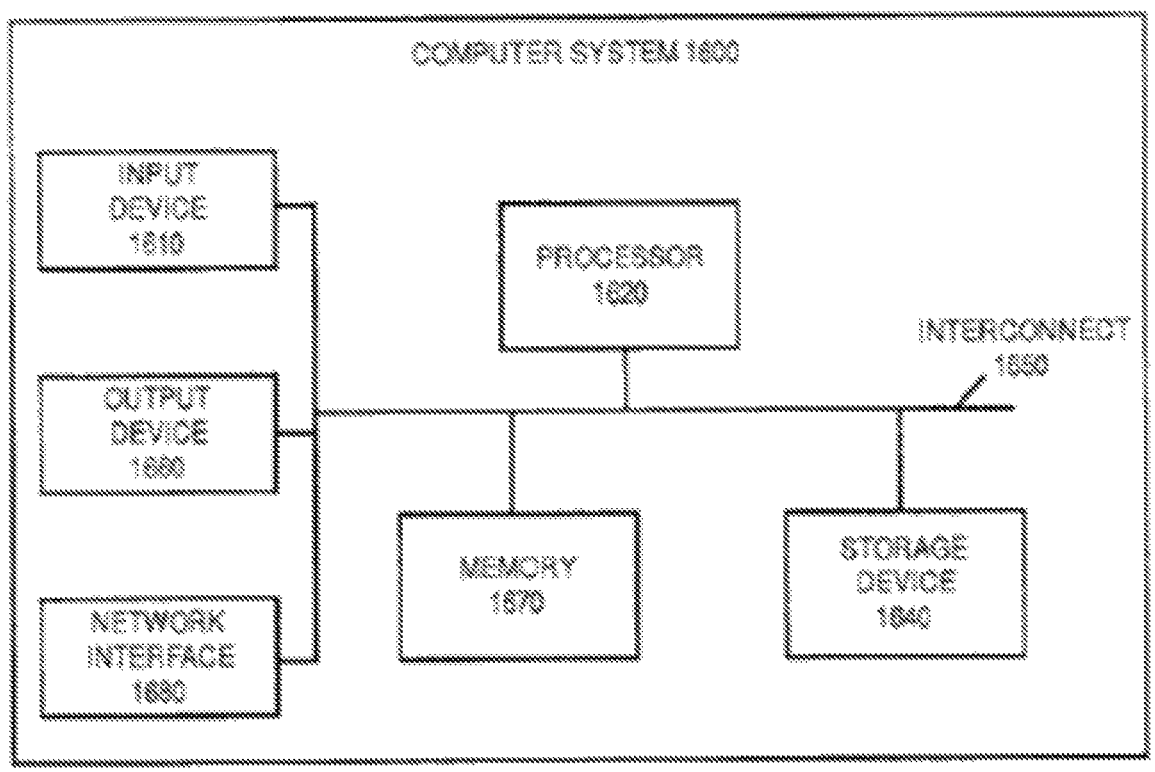
FIG. 26 illustrates an example of a computer system 1600 that may be configured to practice an embodiment of the invention.

FIG. 26 illustrates an example of a computer system 1600 that may be configured to practice an embodiment of the invention. Computer system 1600 may include processor 1620, memory 1670, storage device 1640, input device 1610, output device 1660, and network interface 1680. Processor 1620 may include logic configured to execute computer-executable instructions that implement embodiments of the invention. An example of a processor that may be used with the invention includes the Pentium® processor, Core i7® processor, or Xeon® processor all available from Intel Corporation, Santa Clara, Calif. The instructions may reside in memory 1670 and may include instructions.

Memory 1670 may be a computer-readable medium that may be configured to store instructions configured to implement embodiments of the invention. Memory 1670 may be a primary storage accessible to processor 1620 and can include a random-access memory (RAM) that may include RAM devices, such as, for example, Dynamic RAM (DRAM) devices, flash memory devices, Static RANI (SRAM) devices, etc. Storage device 1640 may include a magnetic disk and/or optical disk and its corresponding drive for storing information and/or instructions.

Interconnect 1650 may include logic that operatively couples components of computer system 1600 together. For example, interconnect 1650 may allow components to communicate with each other, may provide power to components of computer system 1600, etc. In an embodiment of computer system 1600, interconnect 1650 may be implemented as a bus.

Input device 1610 may include logic configured to receive information for computer system 1600 from, e.g., a user. Embodiments of input device 1610 may include keyboards, touch sensitive displays, biometric sensing devices, computer mice, trackballs, pen-based point devices, etc. Output device 1660 may include logic configured to output information from computer system. Embodiments of output device 1660 may include cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc.

Network interface 1680 may include logic configured to interface computer system 1600 with a network, e.g., network 1540, and may enable computer system 1600 to exchange information with other entities connected to the network, such as, for example, service provider 1550, target environment 1560 and cluster 1570. Network interface 1680 may be implemented as a built-in network adapter, network interface card (NIC), Personal Computer Memory Card International Association (PCMCIA) network card, card bus network adapter, wireless network adapter, Universal Serial Bus (USB) network adapter, modem or any other device suitable for interfacing computer system 1600 to any type of network.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated. In addition, the logic flow may be implemented by a hardware element, a software element executed by a processor, or any combination thereof.

It is worthy to note that any reference to "one embodiment" or "an embodiment" means that a particular feature, structure, or characteristic described in connection with the embodiment is included in at least one embodiment. The appearances of the phrase "in one embodiment" in the specification are not necessarily all referring to the same embodiment.

Although some embodiments may be illustrated and described as comprising exemplary functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

EMBODIMENTS

A vessel cannulation device may include a housing having a distal end with a distal tip and a proximal end, a lumen passing through at least the distal tip, a sensor coupled to the lumen, and a blunting device advancing member configured to advance a blunting device, wherein the blunting device is operably coupled to the sensor. The sensor may be configured to sense a physiologic parameter. The blunting device advancing member may be configured to advance the blunting device when the sensor detects that the physiologic parameter within a pre-determined range. The coupling of the sensor to the lumen may be via substantially straight fluid passageways having an internal diameter of 0.5 mm-2.5 mm, and a length no longer than 4 cm.

The vessel cannulation device may also include a trigger mechanism consisting of a sear and a lever, configured to release the blunting device advancing member when the sensor detects that the physiologic parameter within a pre-determined range. The lever has a hinge located at the proximal end of the device. The vessel cannulation device may also include an adjustment mechanism, configured to adjust the pre-determined range of the physiologic parameter. The vessel cannulation device may also include an impact absorbing element for dampening noise and recoil during advancement of the blunting element. The vessel cannulation device may also include a cocking mechanism configured to bring the device to a usable (cocked) state, prior to puncturing the skin. The vessel cannulation device may also include a cover comprising a safety latch slot and a safety latch.

The vessel cannulation device may also include a CPU and actuator. The vessel cannulation device may include a memory that is configured to store computer-executable instructions. The CPU may be configured to execute the computer-executable instructions cause the vessel cannulation device to detect that the needle tip is in a blood vessel. The vessel cannulation device may also include an input means for choosing the target vessel type to determine predetermined values for an artery or a vein. An artery may have predetermined values of Lower Threshold 20 mmHg, Upper Threshold 300 mmHg, and Range of Pressure Change Rate +/−400 mmHg/sec. A vein has predetermined values of Lower Threshold 5 mmHg, Upper Threshold 20 mmHg, and Range of Pressure Change Rate +/−100 mmHg/sec. The computer-executable instructions can incorporate a time window during which the physiologic parameter must be within the predetermined ranges to activate trigger mechanism. The time window for a vein may be between 0.05-0.3 seconds, and for an artery the window may be between 0-0.05 seconds.

The sensor of the vessel cannulation device may be an electronic sensor. The sensor may include multiple sensors, configured to measure physiological parameters at the needle tip.

The device may include a disposable part and of a reusable part. The disposable part may include the sensor, housing, lumen, blunting device, blunting device advancing member, needle, needle adapter, seal, large spring, backplate, and wherein all the rest of the device may be reusable.

When the blunting element is an external sheath, the disposable part may include the sensor, needle, and needle adapter, and the reusable part may include the rest of the device.

When the blunting device is coaxial with the large spring, the disposable part may include the sensor, needle, needle adapter, seal, blunting device advancing member, but not the slider and large spring.

When the blunting device and blunting device advancing member are covered by a sterile cover within the device, the rest of the device may be reusable.

When the blunting device is not coaxial with the large spring, the disposable part may include the sensor, blunting device, gripper, needle, needle adapter, and seal.

The sensor may be reusable when a barrier allowing sensing of pressure is used to keep the sensor sterile.

A blunting device may be configure to be positioned within a needle in its crimped state without substantially blocking the needle's lumen, and to cover the needle's point when in its deployed state. The blunting device may be stent-like. The blunting device may be a guidewire with an uncoiled segment. The blunting device may be a coiling guidewire. The blunting device may be a tip completing element. The blunting device may be an internal sheath. The internal sheath may be configured to cover the needle point. The blunting device may be a "sandwich" sheath.

A vessel cannulation system may include any combination of cannulation devices discussed above and blunting devices discussed above, and a guidance element.

The guidance element may be a linear mechanical guide. The guidance element may be a rotary mechanical guide. The guidance element may include imaging means. The imaging means consists of an ultrasound transducer. The ultrasound transducer may be made of at least two parts such that it is centered around the cannulation device needle tip, and the needle can slide through the transducer, and the transducer can be opened to remove it off the needle shaft. The guidance element may also include a mat with position sensors, a processor, and an indicator. A processor may be configured to gather ultrasound signals received by the transducer simultaneously with the position information from the position sensors; the processor may then activate an indicator to indicate when the cannulation device is pointed at the target vessel.

An autonomic system for vessel cannulation may comprise of a processor, a cannulation device discussed above, slideably positioned within a housing and pivotally connected to a mat with position sensors, strips connected to the mat and to the cannulation device and operated by linear motors, an ultrasound transducer slideably positioned over the tip of the cannulation device needle; the linear motors and strips control the orientation of the cannulation device, and wherein the system scans the tissue in front of the needle by moving the cannulation device, chooses the orientation towards the target vessel, and abruptly advances the device until it deploys within the vessel or until a maximum depth is reached.

An expandable sheath may include at least one layer with longitudinal beams, interconnected in a spiral pattern.

An expandable sheath may include a hub which can overlap with a needle hub.

An expandable sheath includes at least two layers, one with longitudinal beams and a shoulder, and one elastic and radially expandable, slideably positioned over a rigid inner sheath comprising a bulb and a step; the inner sheath is configured to fit over a needle shaft; the inner sheath shoulder is configured to pull the expandable sheath step during insertion into tissue; and after removal of the needle, the bulb is collapsible and the inner sheath can be removed from within the expandable sheath, while leaving the sheath in its position within the body.

An expandable sheath includes at least one layer with longitudinal beams, which are not interconnected, and an external tearable sheath with a handle and a support element connecting said external sheath to the expandable sheath hub. The expandable sheath may also include a rigid large diameter sheath that is configured to be inserted with a mandrel inside it into the expandable sheath, to expand it to its maximal diameter, and maintain it expanded to that diameter.

A central vascular catheter, configured to be inserted over a needle of cannulation devices discussed above, may further include a support element connecting it to the needle hub.

A method of placing a central vascular catheter using cannulation devices discussed above, and sheaths discussed above may include following placement of the expandable sheath in a blood vessel, the central catheter is inserted through the expandable sheath.

A method of placing a central vascular catheter using cannulation devices discussed above, and central catheter discussed above; the central catheter is pre-mounted over the needle of the cannulation device. The method may include following deployment of a blunting device in a blood vessel, the central catheter may be pushed into the blood vessel over the needle and over the blunting device.

A method of placing a peripheral IV catheter using cannulation devices discussed above, the peripheral IV catheter may be pre-mounted over the needle of the cannulation device. The method may include following automatic deployment of a blunting device in a blood vessel, the peripheral IV catheter is inserted into the blood vessel over the needle and blunting device.

A method of blood sampling using cannulation devices discussed above and blunting devices discussed above, may include following automatic deployment of a blunting device in a blood vessel, where blood is drawn through the blunted needle from the needle port or a port in the cannulation device.

An expandable sheath configured for being inserted over a needle may have at least one longitudinal corrugation. The sheath may have multiple micro-corrugations. The sheath may have one corrugation, and the corrugation is folded around the sheath at least once.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

What is claimed is:

1. An automatic vessel cannulation device comprising:
   a housing having a distal end with a distal tip and a proximal end;
   a lumen passing through the distal end and the proximal end;
   a needle at the distal tip of the housing, wherein the needle having a needle tip;
   a sensor operably coupled to the lumen, wherein the sensor being configured to detect a combination of physiologic parameters at the needle tip; and
   a blunting device advancing member configured to advance a blunting device, wherein the blunting device advancing member is operably coupled to the sensor, wherein the blunting device advancing member is configured to automatically advance the blunting device when the sensor detects that the combination of physiologic parameters are within a pre-determined range.

2. The device of claim 1, wherein the sensor is selected from the group consisting of pressure sensors, temperature sensors, conductivity sensors, flow sensors, ultrasound sensors, pH sensors, and optical sensors.

3. The device of claim 1, further comprising a trigger mechanism comprising a sear and a lever, wherein the trigger mechanism is configured to release the blunting device advancing member when the sensor detects that the combination of physiologic parameters are within the pre-determined range.

4. The device of claim 3, wherein the lever comprises a hinge located at the distal end of the device, a lever tooth at the proximal end, and a lever base between the hinge and the lever tooth.

5. The device of claim 4, wherein the sear is located at the proximal end of the lever and engages the lever tooth.

6. The device of claim 3, wherein the lever comprises a hinge at the proximal end of the device, a lever base at the distal end of the device, and a lever tooth between the hinge and the lever base, wherein the lever is operably coupled to and moveable by the sensor.

7. The device of claim 6, wherein the sear is located between the proximal end and the distal end of the lever and engages the lever tooth.

8. The device of claim 6, wherein the distance from the center of the sensor to the hinge is twice the distance from the lever tooth to the hinge.

9. The device of claim 8, wherein the sensor is a membrane.

10. The device of claim 3, further comprising an adjustment mechanism configured to be in contact with the trigger mechanism, wherein the adjustment mechanism adjusts force applied on the lever.

11. The device of claim 3, further comprising a CPU, wherein the CPU is in electrical communication with the sensor and is configured to execute instructions, wherein when executed, the CPU is configured to compare the combination of physiologic parameters from the needle tip with predetermined values to determine whether the needle tip has punctured a blood vessel.

12. The device of claim 11, further comprising a solenoid in communication with the CPU and connected to the trigger mechanism, wherein the solenoid activates the trigger mechanism when it is determined that the combination of physiologic parameters from the needle tip matches a combination of predetermined parameters of the blood vessel.

13. The device of claim 12, wherein the solenoid is configured to activate outside of a predetermined time window, wherein the predetermined time window for a vein is between 0.05-0.3 seconds, and the predetermined time window for an artery the window is between 0-0.05 seconds.

14. The device of claim 11, further comprising input device for choosing a blood vessel type, wherein the blood vessel type is an artery or a vein.

15. The device of claim 14, wherein the artery has a predetermined parameter of lower threshold (LTH) of 20 mmHg, upper threshold (UTH) of 300 mmHg, and range of pressure change rate of +/−400 mmHg/sec.

16. The device of claim 14, wherein the vein has a predetermined parameter of lower threshold (LTH) of 5 mmHg, upper threshold (UTH) of 20 mmHg, and range of pressure change rate of +/−100 mmHg/sec.

17. The device of claim 1, wherein the blunting device advancing member is coaxial with a large spring.

18. The device of claim 1, wherein the blunting device and the blunting device advancing member are covered by a sterile cover within the device.

19. The device of claim 1, further comprises a blunting element configured to expand to cover the needle tip when deployed.

20. The device of claim 19, wherein the blunting element is stent-like.

21. The device of claim 19, wherein the blunting element is selected from the group consisting of an external sheath, an internal sheath, a sandwich sheath, a tip covering sheath, and a tip completing sheath.

22. The device of claim 21, wherein the internal sheath is a guidewire with an uncoiled segment or a coiling guidewire.

23. The device of claim 21, wherein the internal sheath is deployed by pushing the internal sheath towards the needle tip with a cannulation device.

24. The device of claim 21, wherein the internal sheath is configured to be positioned within the needle in its crimped state without substantially blocking a needle lumen.

25. The devices of claim 1, wherein the sensor is an electronic sensor.

26. The device of claim 1, wherein the sensor comprises multiple sensors.

27. The device of claim 1, further comprising a fluid passageway coupling the sensor to the lumen; and wherein the fluid passageway is substantially straight and has an internal diameter of 0.5 mm-2.5 mm, and a length no longer than 4 cm.

28. The device of claim 1, further comprising an impact absorbing element for dampening noise and recoil during advancement of the blunting device.

29. The device of claim 1, further comprising a cocking mechanism configured to bring the device to a cocked state.

30. The device of claim 1, further comprising a cover comprising a safety latch slot and a safety latch.

31. The device of claim 1, wherein the device comprises of a disposable part and of a reusable part.

32. The device of claim 1, further comprising a barrier allowing sensing to be performed while keeping the sensor sterile, and wherein the sensor is reusable.

33. The device of claim 1, further comprising a guidance element.

34. The device of claim 33, wherein the guidance element is selected from a group consisting of a linear mechanical guide or a rotary mechanical guide.

35. The device of claim 33, wherein the guidance element includes imaging means.

36. The device of claim 35, wherein the imaging means consists of an ultrasound transducer.

37. The device of claim 36, wherein the ultrasound transducer is located proximal to the needle tip, and wherein the needle can slide through the transducer.

38. The device of claim 36, wherein the ultrasound transducer allows replacement or removal of the needle.

39. The device of claim 36, further comprising a mat comprising position sensors, a processor, and an indicator;
wherein the processor is configured to gather ultrasound signals received by the ultrasound transducer simultaneously with position information from the position sensors; and
wherein the processor activates the indicator to signal when the cannulation device is pointed at a blood vessel.

40. An automatic system for vessel cannulation comprising:
a mat having position sensors and a sliding strip,
a motor controlling a movement of the sliding strip,
a processor in electronic communication with the mat,
a vessel cannulation device of claim 1, slideably positioned within a housing and pivotally connected to the mat through the sliding strips, wherein the vessel cannulation device comprises a needle; and
an ultrasound transducer slideably positioned over the tip of the needle of the vessel cannulation device,
wherein the motor controls an orientation of the cannulation device through the sliding strip, and wherein the system scans tissue with the tip of the needle by moving the cannulation device through the ultrasound transducer.

41. The automatic system of claim 40, wherein the processor detects a target vessel, advances the vessel cannulation device towards the target vessel, until the vessel cannulation device deploys a guidewire within the vessel or until a maximum depth is reached.

42. A method of using a vessel cannulation system comprising:
calibrating the system by selecting a target vessel type having pre-determined parameters;
penetrating a body with a needle to detect a combination of physiologic parameters, wherein the needle is in electronic communication with the system;
comparing the combination of physiologic parameters with the pre-determined parameters; and
deploying a blunting element into the target vessel if the combination of physiologic parameters are within a range of the pre-determined parameters.

43. The method of claim 42, further comprising pushing forward an inner sheath from an inner lumen of the needle towards a distal tip of the needle.

44. The method of claim 42, wherein the deploying step further comprises activating a solenoid to trigger a trigger mechanism to advance the blunting element.

45. The method of claim 42, wherein the blunting element is configured to be positioned within the needle in its crimped state without substantially blocking an inner lumen, and to cover a distal tip when the blunting element is deployed.

46. The method of claim 42, wherein the blunting element is selected from the group consisting of an external sheath, an internal sheath, a sandwich sheath, a tip covering sheath, and a tip completing sheath.

47. The method of claim 42, further comprising:
placing a mechanical guide on the body with a central marking above an estimated location of the target vessel.

48. The method of claim 47, wherein the mechanical guide is an ultrasound transducer.

49. The method of claim 42, wherein the calibrating step comprises choosing a target vessel type, wherein the target vessel type is an artery or a vein.

50. The method of claim 49, wherein the artery has a pre-determined parameter of lower threshold (LTH) of 20 mmHg, upper threshold (UTH) of 300 mmHg, and range of pressure change rate of +/−400 mmHg/sec.

51. The method of claim 49, wherein the vein has a pre-determined parameter of lower threshold (LTH) of 5 mmHg, upper threshold (UTH) of 20 mmHg, and range of pressure change rate of +/−100 mmHg/sec.

52. The method of claim 42, wherein the penetrating step comprises using sensors to detect the combination of physiologic parameters at a needle tip.

53. The method of claim 42, further comprising inserting a central catheter into the target vessel through the blunting element, wherein the blunting element is an expandable sheath.

54. The method of claim 42, further comprising inserting a peripheral IV catheter into the target vessel through the blunting element, wherein the blunting element is an expandable sheath.

55. The method of claim 42, further comprising drawing blood sampling through the blunting element.

56. The method of claim 42, wherein the blunting element is pulled back following deployment to cover a needle tip.

57. The device of claim 1, wherein the blunting device is configured to advance through the lumen.

58. An automatic vessel cannulation device comprising:
a housing having a distal end with a distal tip and a proximal end;
a lumen passing through the distal end and the proximal end;
a needle at the distal tip of the housing, wherein the needle having a needle tip;
a sensor operably coupled to the lumen, wherein the sensor being configured to detect a physiologic parameter at the needle tip;
a blunting device advancing member configured to advance a blunting device, wherein the blunting device advancing member is operably coupled to the sensor;

a trigger mechanism comprising a sear and a lever, wherein the trigger mechanism is configured to release the blunting device advancing member when the sensor detects that the physiologic parameter is within a pre-determined range; and an adjustment mechanism configured to be in contact with the trigger mechanism, wherein the adjustment mechanism adjusts force applied on the lever, wherein the blunting device advancing member is configured to automatically advance the blunting device when the sensor detects that the physiologic parameter within the pre-determined range.

59. An automatic vessel cannulation device comprising:

a housing having a distal end with a distal tip and a proximal end;

a lumen passing through the distal end and the proximal end;

a needle at the distal tip of the housing, wherein the needle having a needle tip;

a sensor operably coupled to the lumen, wherein the sensor being configured to detect a physiologic parameter at the needle tip; and a blunting device advancing member configured to advance a blunting device, wherein the blunting device advancing member is operably coupled to the sensor, wherein the blunting device advancing member is configured to automatically advance the blunting device when the sensor detects that the physiologic parameter within a pre-determined range, wherein the blunting device and the blunting device advancing member are covered by a sterile cover within the device.

60. An automatic vessel cannulation device comprising:

a housing having a distal end with a distal tip and a proximal end;

a lumen passing through the distal end and the proximal end;

a needle at the distal tip of the housing, wherein the needle having a needle tip;

a sensor operably coupled to the lumen, wherein the sensor being configured to detect a physiologic parameter at the needle tip;

a blunting device advancing member configured to advance a blunting device, wherein the blunting device advancing member is operably coupled to the sensor; and a blunting element configured to expand to cover the needle tip when deployed, wherein the blunting device advancing member is configured to automatically advance the blunting device when the sensor detects that the physiologic parameter within a pre-determined range, wherein the blunting element is selected from the group consisting of an external sheath, an internal sheath, a sandwich sheath, a tip covering sheath, and a tip completing sheath wherein the internal sheath is configured to be positioned within the needle in its crimped state without substantially blocking a needle lumen.

61. An automatic vessel cannulation device comprising:

a housing having a distal end with a distal tip and a proximal end;

a lumen passing through the distal end and the proximal end;

a needle at the distal tip of the housing, wherein the needle having a needle tip;

a sensor operably coupled to the lumen, wherein the sensor being configured to detect a physiologic parameter at the needle tip;

a blunting device advancing member configured to advance a blunting device through the, wherein the blunting device advancing member is operably coupled to the sensor; and an impact absorbing element for dampening noise and recoil during advancement of the blunting device, wherein the blunting device advancing member is configured to automatically advance the blunting device when the sensor detects that the physiologic parameter within a pre-determined range.

62. A method of using a vessel cannulation system comprising:

calibrating the system by selecting a target vessel type having pre-determined parameters;

penetrating a body with a needle to detect a physiologic parameter, wherein the needle is in electronic communication with the system;

comparing the physiologic parameter with the pre-determined parameters; and deploying a blunting element into the target vessel if the physiologic parameter is within a range of the pre-determined parameters, wherein the blunting element is configured to be positioned within the needle in its crimped state without substantially blocking an inner lumen, and to cover a distal tip when the blunting element is deployed.

* * * * *